US012195529B2

(12) United States Patent
Basi

(10) Patent No.: US 12,195,529 B2
(45) Date of Patent: Jan. 14, 2025

(54) HETERODIMERIC BISPECIFIC ANTIBODIES

(71) Applicant: GSBIO, LLC, Palo Alto, CA (US)

(72) Inventor: Guriqbal S. Basi, Palo Alto, CA (US)

(73) Assignee: GSBIO, LLC, Palo Alto, CA (US)

( * ) Notice: Subject to any disclaimer, the term of this patent is extended or adjusted under 35 U.S.C. 154(b) by 718 days.

(21) Appl. No.: 16/625,628

(22) PCT Filed: Jun. 21, 2018

(86) PCT No.: PCT/US2018/038833

§ 371 (c)(1),
(2) Date: Dec. 20, 2019

(87) PCT Pub. No.: WO2018/237192

PCT Pub. Date: Dec. 27, 2018

(65) Prior Publication Data

US 2022/0162297 A1 May 26, 2022

Related U.S. Application Data

(60) Provisional application No. 62/523,220, filed on Jun. 21, 2017.

(51) Int. Cl.

*A61K 39/00* (2006.01)
*C07K 14/725* (2006.01)
*C07K 14/74* (2006.01)
*C07K 16/24* (2006.01)

(52) U.S. Cl.

CPC ........ *C07K 16/241* (2013.01); *C07K 14/7051* (2013.01); *C07K 14/70539* (2013.01); *A61K 39/00* (2013.01); *C07K 2317/31* (2013.01); *C07K 2317/53* (2013.01); *C07K 2317/56* (2013.01); *C07K 2317/64* (2013.01); *C07K 2319/00* (2013.01)

(58) Field of Classification Search

CPC .............. C07K 16/241; C07K 14/7051; C07K 14/70539; C07K 2317/31; C07K 2317/53; C07K 2317/56; C07K 2317/64; C07K 2319/00; A61K 39/00

See application file for complete search history.

(56) References Cited

U.S. PATENT DOCUMENTS

2013/0039913 A1 2/2013 Labrijn et al.
2014/0294823 A1* 10/2014 Moore ................ C07K 16/468 435/254.2
2016/0215047 A1* 7/2016 Pitzalis .................. C07K 16/28

FOREIGN PATENT DOCUMENTS

WO WO 2018/237192 A1 12/2018

OTHER PUBLICATIONS

Gunasekaran et al, The Journal of Biological Chemistry, vol. 285, No. 25, p. 19637-19646, Jun. 18, 2010. (Year: 2010).*
Li et al, Chinese medical Journal, Feb. 20, 2016, vol. 129, Issue 4, p. 448-455. (Year: 2016).*
PCT/US2018/038833 Invitation of Pay Additional Fees mailed Aug. 29, 2018.
PCT/US2018/038833 International Search Report and Written Opinion mailed Oct. 18, 2018.
PCT/US2018/038833 International Preliminary Report on Patentability mailed Dec. 24, 2019.
Wei, et al., "Structural basis of a novel heterodimeric Fc for bispecific antibody production," Oncatarget, vol. 8, (No. 31), pp. 51037-51048, (May 2, 2017).
Gross, et al., "Expression of immunoglobulin-T-cell receptor chimeric molecules as functional receptors with antibody-type specificity," Proc. Natl. Acad. Sci. USA, vol. 86, pp. 10024-10028, (Dec. 1989).

* cited by examiner

*Primary Examiner* — Meera Natarajan
*Assistant Examiner* — Cheom-Gil Cheong
(74) *Attorney, Agent, or Firm* — Alston & Bird LLP

(57) ABSTRACT

The invention provides bispecific heterodimeric antibodies with modified heavy chain IgG constant regions that promote efficient assembly of antibody heavy chain heterodimer pairs, as well as arm specific pairing of heavy and light chains.

10 Claims, 44 Drawing Sheets

Specification includes a Sequence Listing.

Fig. 6A atggacatgagggtccccgctcagctcctggggctcctgctgctctggctcccaggtgccaaatgtGACATCCAGATGACCCAGT
CCCCCTCCTCCCTGTCCGCCTCCGTGGGCGACCGCGTGACCATCACCTGCCGCGCCTCCCAGGGCATCCG
CAACTACCTGGCCTGGTACCAGCAGAAGCCCGGCAAGGCCCCCAAGCTGCTGATCTACGCCGCCTCCAC
CCTGCAGTCCGGCGTGCCCTCCCGCTTCTCCGGCTCCGGCTCCGGCACCGACTTCACCCTGACCATCTCCT
CCCTGCAGCCCGAGGACGTGGCCACCTACTACTGCCAGCGCTACAACCGCGCCCCCTACACCTTCGGCCA
GGGCACCAAGGTGGAGATCAAGCgcaccgtggccgccccctccgtgttcatcttccccccctccgacgagcagctgaagtccg
gcaccgcctccgtggtgtgcctgctgaacaacttctacccccgcgaggccaaggtgcagtggaaggtggacaacgccctgcagtccggc
aactcccaggagtccgtgaccgagcaggactccaaggactccacctactccctgtcctccaccctgaccctgtccaaggccgactacgag
aagcacaaggtgtacgcctgcgaggtgacccaccagggcctgtcctcccccgtgaccaagtccttcaaccgcggcgagtgctag

Fig. 6B mdmrvpaqllgllllwlpgakcDIQMTQSPSSLSASVGDRVTITCRASQGIRNYLAWYQQKPGKAPKLLIYAASTLQ
SGVPSRFSGSGSGTDFTLTISSLQPEDVATYYCQRYNRAPYTFGQGTKVEIKRtvaapsvfifppsdeqlksgtasvvcl
lnnfypreakvqwkvdnalqsgnsqesvteqdskdstyslsstltlskadyekhkvyacevthqglsspvtksfnrgec•

Fig. 7A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaaccacaggtgtacaccctgcccccatcccg
ggatgagctgaccaagaaccaggtcagcctgacctgcctggtcaaaggcttctatcccagcgacatcgccgtggagtgggagagcaatg
ggcagccggagaacaactacaagaccacgcctcccgtgctggactccgacggctccttcttcctctacagcaagctcaccgtggacaag
agcaggtggcagcaggggaacgtcttctcatgctccgtgatgcatgaggctctgcacaaccactacacgcagaagagcctctccctgtct
ccgggtaaatga

Fig. 7B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkve*
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprepqvytlppsrdeltknqvsltclvkgfypsdiavewesngqp
ennykttppvldsdgsfflyskltvdksrwqqgnvfscsvmhealhnhytqkslslspgk•

Fig. 8A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaacca*GAGACGCTGCAGCGCACG*G
ACGCCCCCAAAACGCATATGACTCACCACGCTGTCTCTGACCATGAAGCCACCCTGAGGTGCTGGGCCC
TGAGCTTCTACCCTGCGGAGATCACACTGACCTGGCAGCGGGATGGGGAGGACCAGACCCAGGACAC
GGAGCTCGTGGAGACCAGGCCTGCAGGGGATGGAACCTTCCAGAAGTGGGTGGCTGTGGTGGTGCCT
TCTGGACAGGAGCAGAGATACACCTGCCATGTGCAGCATGAGGGTTTGCCCAAGCCCCTCACCCTGAG
ATGGTGA

Fig. 8B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkv*e
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprep*ETLQRT*DAPKTHMTHHAVSDHEATLRCWALSF
YPAEITLTWQRDGEDQTQDTELVETRPAGDGTFQKWVAVVVPSGQEQRYTCHVQHEGLPKPLTLRW•

Fig 8C

*GAGACGCTGCAGCGCACG*GACGCCCCCAAAACGCATATGACTCACCACGCTGTCTCTGACCATGAAGC
CACCCTGAGGTGCTGGGCCCTGAGCTTCTACCCTGCGGAGATCACACTGACCTGGCAGCGGGATGGG
GAGGACCAGACCCAGGACACGGAGCTCGTGGAGACCAGGCCTGCAGGGGATGGAACCTTCCAGAAG
TGGGTGGCTGTGGTGGTGCCTTCTGGACAGGAGCAGAGATACACCTGCCATGTGCAGCATGAGGGTT
TGCCCAAGCCCCTCACCCTGAGATGGTGA

Fig 8D

*ETLQRT*DAPKTHMTHHAVSDHEATLRCWALSFYPAEITLTWQRDGEDQTQDTELVETRPAGDGTFQKW
VAVVVPSGQEQRYTCHVQHEGLPKPLTLRW•

Fig. 9A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttcccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaaccaATCCAGCGTACTCCAAAGA
TTCAGGTTTACTCACGTCATCCAGCAGAGAATGGAAAGTCAAATTTCCTGAATTGCTATGTGTCTGGGT
TTCATCCATCCGACATTGAAGTTGACTTACTGAAGAATGGAGAGAGAATTGAAAAAGTGGAGCATTC
AGACTTGTCTTTCAGCAAGGACTGGTCTTTCTATCTCTTGTACTACACTGAATTCACCCCCACTGAAAAA
GATGAGTATGCCTGCCGTGTGAACCATGTGACTTTGTCACAGCCCAAGATAGTTAAGTGGGATCGAGA
CATGTAA

Fig. 9B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkv*e
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprepIQRTPKIQVYSRHPAENGKSNFLNCYVSGFHPS
DIEVDLLKNGERIEKVEHSDLSFSKDWSFYLLYYTEFTPTEKDEYACRVNHVTLSQPKIVKWDRDM•

Fig 9C

**ATCCAGCGTACTCCAAAGATTCAGGTTTACTCACGTCATCCAGCAGAGAATGGAAAGTCAAATTTCCT
GAATTGCTATGTGTCTGGGTTTCATCCATCCGACATTGAAGTTGACTTACTGAAGAATGGAGAGAGAA
TTGAAAAAGTGGAGCATTCAGACTTGTCTTTCAGCAAGGACTGGTCTTTCTATCTCTTGTACTACACTG
AATTCACCCCCACTGAAAAAGATGAGTATGCCTGCCGTGTGAACCATGTGACTTTGTCACAGCCCAAG
ATAGTTAAGTGGGATCGAGACATGTAA**

Fig. 9D

**IQRTPKIQVYSRHPAENGKSNFLNCYVSGFHPSDIEVDLLKNGERIEKVEHSDLSFSKDWSFYLLYYTEFTPTE
KDEYACRVNHVTLSQPKIVKWDRDM•**

Fig 10A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaacca*ACTCCGATCACCAAT*GTACC
TCCAGAGGTAACTGTGCTCACAAACAGCCCTGTGGAACTGAGAGAGCCCAACGTCCTCATCTGTTTCAT
AGACAAGTTCACCCCACCAGTGGTCAATGTCACGTGGCTTCGAAATGGAAAACCTGTCACCACAGGAG
TGTCAGAGACAGTCTTCCTGCCCAGGGAAGACCACCTTTTCCGCAAGTTCCACTATCTCCCCTTCCTGCC
CTCAACTGAGGACGTTTACGACTGCAGGGTGGAGCACTGGGGCTTGGATGAGCCTCTTCTCAAGCACT
GGGAGTTTGATGCTCCAAGCCCTCTCCCAGAGACTACAGAGAACTAA

Fig. 10B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkve*
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprep*TPIT*NVPPEVTVLTNSPVELREPNVLICFIDKFTPP
VVNVTWLRNGKPVTTGVSETVFLPREDHLFRKFHYLPFLPSTEDVYDCRVEHWGLDEPLLKHWEFDAPSP
LPETTEN•

Fig. 10C

*ACTCCGATCACCAAT*GTACCTCCAGAGGTAACTGTGCTCACAAACAGCCCTGTGGAACTGAGAGAGCC
CAACGTCCTCATCTGTTTCATAGACAAGTTCACCCCACCAGTGGTCAATGTCACGTGGCTTCGAAATGG
AAAACCTGTCACCACAGGAGTGTCAGAGACAGTCTTCCTGCCCAGGGAAGACCACCTTTTCCGCAAGT
TCCACTATCTCCCCTTCCTGCCCTCAACTGAGGACGTTTACGACTGCAGGGTGGAGCACTGGGGCTTGG
ATGAGCCTCTTCTCAAGCACTGGGAGTTTGATGCTCCAAGCCCTCTCCCAGAGACTACAGAGAACTAA

Fig. 10D

*TPIT*NVPPEVTVLTNSPVELREPNVLICFIDKFTPPVVNVTWLRNGKPVTTGVSETVFLPREDHLFRKFHYLP
FLPSTEDVYDCRVEHWGLDEPLLKHWEFDAPSPLPETTEN•

Fig. 11A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaacca*CGAGTCCAACCT*AAGGTGA
CTGTATATCCTTCAAAGACCCAGCCCCTGCAGCACCACAACCTCCTGGTCTGCTCTGTGAGTGGTTTCTA
TCCAGGCAGCATTGAAGTCAGGTGGTTCCTGAACGGCCAGGAAGAGAAGGCTGGGATGGTGTCCACA
GGCCTGATCCAGAATGGAGACTGGACCTTCCAGACCCTGGTGATGCTGGAAACAGTTCCTCGAAGTG
GAGAGGTTTACACCTGCCAAGTGGAGCACCCAAGCGTGACAAGCCCTCTCACAGTGGAATGGAGAGC
ACGGTCTGAATCTGCACAGAGCAAGATGCTGAGTTGA

Fig. 11B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkv*e
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprep*RVQP*KVTVYPSKTQPLQHHNLLVCSVSGFYPGS
IEVRWFLNGQEEKAGMVSTGLIQNGDWTFQTLVMLETVPRSGEVYTCQVEHPSVTSPLTVEWRARSESA
QSKMLS•

Fig. 11C

*CGAGTCCAACCT*AAGGTGACTGTATATCCTTCAAAGACCCAGCCCCTGCAGCACCACAACCTCCTGGTC
TGCTCTGTGAGTGGTTTCTATCCAGGCAGCATTGAAGTCAGGTGGTTCCTGAACGGCCAGGAAGAGA
AGGCTGGGATGGTGTCCACAGGCCTGATCCAGAATGGAGACTGGACCTTCCAGACCCTGGTGATGCT
GGAAACAGTTCCTCGAAGTGGAGAGGTTTACACCTGCCAAGTGGAGCACCCAAGCGTGACAAGCCCT
CTCACAGTGGAATGGAGAGCACGGTCTGAATCTGCACAGAGCAAGATGCTGAGTTGA

Fig. 11D

*RVQP*KVTVYPSKTQPLQHHNLLVCSVSGFYPGSIEVRWFLNGQEEKAGMVSTGLIQNGDWTFQTLVMLE
TVPRSGEVYTCQVEHPSVTSPLTVEWRARSESAQSKMLS•

Fig. 12A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaacca*AATATCCAGAACCCTGACCC*
*T*GCCGTGTACCAGCTGAGAGACTCTAAATCCAGTGACAAGTCTGTCTGCCTATTCACCGATTTTGATTC
TCAAACAAATGTGTCACAAAGTAAGGATTCTGATGTGTATATCACAGACAAAACTGTGCTAGACATGA
GGTCTATGGACTTCAAGAGCAACAGTGCTGTGGCCTGGAGCAACAAATCTGACTTTGCATGTGCAAAC
GCCTTCAACAACAGCATTATTCCAGAAGACACCTTCTTCCCCAGCCCAGAAAGTTCCTGTGATGTCAAGC
TGGTCGAGAAAAGCTTTGAAACAGATACGTGA

Fig. 12B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkve*
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprep*NIQNPDP*AVYQLRDSKSSDKSVCLFTDFDSQTN
VSQSKDSDVYITDKTVLDMRSMDFKSNSAVAWSNKSDFACANAFNNSIIPEDTFFPSPESSCDVKLVEKSF
ETDT•

Fig. 12C

*AATATCCAGAACCCTGACCCT*GCCGTGTACCAGCTGAGAGACTCTAAATCCAGTGACAAGTCTGTCTGC
CTATTCACCGATTTTGATTCTCAAACAAATGTGTCACAAAGTAAGGATTCTGATGTGTATATCACAGAC
AAAACTGTGCTAGACATGAGGTCTATGGACTTCAAGAGCAACAGTGCTGTGGCCTGGAGCAACAAAT
CTGACTTTGCATGTGCAAACGCCTTCAACAACAGCATTATTCCAGAAGACACCTTCTTCCCCAGCCCAG
AAAGTTCCTGTGATGTCAAGCTGGTCGAGAAAAGCTTTGAAACAGATACGTGA

Fig. 12D

*NIQNPDP*AVYQLRDSKSSDKSVCLFTDFDSQTNVSQSKDSDVYITDKTVLDMRSMDFKSNSAVAWSNKS
DFACANAFNNSIIPEDTFFPSPESSCDVKLVEKSFETDT•

Fig. 13A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaacca*CTCGAGGACCTGAAAAACG*
*TGTTC*CCACCCGAGGTCGCTGTGTTTGAGCCATCAGAAGCAGAGATCTCCCACACCCAAAAGGCCACA
CTGGTGTGCCTGGCCACAGGCTTCTACCCCGACCACGTGGAGCTGAGCTGGTGGGTGAATGGGAAGG
AGGTGCACAGTGGGGTCAGCACAGACCCGCAGCCCCTCAAGGAGCAGCCCGCCCTCAATGACTCCAG
ATACTGCCTGAGCAGCCGCCTGAGGGTCTCGGCCACCTTCTGGCAGAACCCCCGCAACCACTTCCGCTG
TCAAGTCCAGTTCTACGGGCTCTCGGAGAATGACGAGTGGACCCAGGATAGGGCCAAACCTGTCACCC
AGATCGTCAGCGCCGAGGCCTGGGGTAGAGCAGACTAG

Fig. 13B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkv*e
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprep*LEDLKNVF*PPEVAVFEPSEAEISHTQKATLVCLAT
GFYPDHVELSWWVNGKEVHSGVSTDPQPLKEQPALNDSRYCLSSRLRVSATFWQNPRNHFRCQVQFYG
LSENDEWTQDRAKPVTQIVSAEAWGRAD•

Fig. 13C

*CTCGAGGACCTGAAAAACGTGTTC*CCACCCGAGGTCGCTGTGTTTGAGCCATCAGAAGCAGAGATCTCC
CACACCCAAAAGGCCACACTGGTGTGCCTGGCCACAGGCTTCTACCCCGACCACGTGGAGCTGAGCTG
GTGGGTGAATGGGAAGGAGGTGCACAGTGGGGTCAGCACAGACCCGCAGCCCCTCAAGGAGCAGCC
CGCCCTCAATGACTCCAGATACTGCCTGAGCAGCCGCCTGAGGGTCTCGGCCACCTTCTGGCAGAACCC
CCGCAACCACTTCCGCTGTCAAGTCCAGTTCTACGGGCTCTCGGAGAATGACGAGTGGACCCAGGATA
GGGCCAAACCTGTCACCCAGATCGTCAGCGCCGAGGCCTGGGGTAGAGCAGACTAG

Fig. 13D

*LEDLKNVF*PPEVAVFEPSEAEISHTQKATLVCLATGFYPDHVELSWWVNGKEVHSGVSTDPQPLKEQPAL
NDSRYCLSSRLRVSATFWQNPRNHFRCQVQFYGLSENDEWTQDRAKPVTQIVSAEAWGRAD•

Fig. 14A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaag*ttgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaacca*ACAGATAAACAACTTGATGC*
*AGATGTTTCC*CCCAAGCCCACTATTTTTCTTCCTTCAATTGCTGAAACAAAGCTCCAGAAGGCTGGAAC
ATACCTTTGTCTTCTTGAGAAATTTTTCCCTGATGTTATTAAGATACATTGGGAAGAAAAGAAGAGCAA
CACGATTCTGGGATCCCAGGAGGGGAACACCATGAAGACTAATGACACATACATGAAATTTAGCTGG
TTAACGGTGCCAGAAAAGTCACTGGACAAAGAACACAGATGTATCGTCAGACATGAGAATAATAAAA
ACGGAGTTGATCAAGAAATTATCTTTCCTCCAATAAAGACAGATGTCATCACAATGGATCCCAAAGACA
ATTGTTCAAAAGATGCAAATGATACACTACTGCTGCAGCTCACAAACTAA

Fig. 14B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkv*e
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprep*TDKQLDADVS*PKPTIFLPSIAETKLQKAGTYLCLL
EKFFPDVIKIHWEEKKSNTILGSQEGNTMKTNDTYMKFSWLTVPEKSLDKEHRCIVRHENNKNGVDQEIIF
PPIKTDVITMDPKDNCSKDANDTLLLQLTN•

Fig. 14C

*ACAGATAAACAACTTGATGCAGATGTTTCC*CCCAAGCCCACTATTTTTCTTCCTTCAATTGCTGAAACAA
AGCTCCAGAAGGCTGGAACATACCTTTGTCTTCTTGAGAAATTTTTCCCTGATGTTATTAAGATACATT
GGGAAGAAAAGAAGAGCAACACGATTCTGGGATCCCAGGAGGGGAACACCATGAAGACTAATGACA
CATACATGAAATTTAGCTGGTTAACGGTGCCAGAAAAGTCACTGGACAAAGAACACAGATGTATCGT
CAGACATGAGAATAATAAAAACGGAGTTGATCAAGAAATTATCTTTCCTCCAATAAAGACAGATGTCA
TCACAATGGATCCCAAAGACAATTGTTCAAAAGATGCAAATGATACACTACTGCTGCAGCTCACAAACTA
A

Fig. 14D

*TDKQLDADVS*PKPTIFLPSIAETKLQKAGTYLCLLEKFFPDVIKIHWEEKKSNTILGSQEGNTMKTNDTYMKF
SWLTVPEKSLDKEHRCIVRHENNKNGVDQEIIFPPIKTDVITMDPKDNCSKDANDTLLLQLTN•

Fig. 15A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaacca*AGAAGTCAGCCTCATACCAA*
*ACCA*TCCGTTTTTGTCATGAAAAATGGAACAAATGTCGCTTGTCTGGTGAAGGAATTCTACCCCAAGG
ATATAAGAATAAATCTCGTGTCATCCAAGAAGATAACAGAGTTTGATCCTGCTATTGTCATCTCTCCCA
GTGGGAAGTACAATGCTGTCAAGCTTGGTAAATATGAAGATTCAAATTCAGTGACATGTTCAGTTCAA
CACGACAATAAAACTGTGCACTCCACTGACTTTGAAGTGAAGACAGATTCTACAGATCACGTAAAACCA
AAGGAAACTGAAAACACAAAGCAACCTTCAAAGAGCTGCCATAAACCCAAAGCCATAGTTCATACCGAG
AAGGTGAACATGTAA

Fig. 15B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkve*
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprep*RSQPHTKP*SVFVMKNGTNVACLVKEFYPKDIRI
NLVSSKKITEFDPAIVISPSGKYNAVKLGKYEDSNSVTCSVQHDNKTVHSTDFEVKTDSTDHVKPKETENTK
QPSKSCHKPKAIVHTEKVNM•

Fig. 15C

*AGAAGTCAGCCTCATACCAAACCA*TCCGTTTTTGTCATGAAAAATGGAACAAATGTCGCTTGTCTGGTG AAGGAATTCTACCCCAAGGATATAAGAATAAATCTCGTGTCATCCAAGAAGATAACAGAGTTTGATCC TGCTATTGTCATCTCTCCCAGTGGGAAGTACAATGCTGTCAAGCTTGGTAAATATGAAGATTCAAATTC AGTGACATGTTCAGTTCAACACGACAATAAAACTGTGCACTCCACTGACTTTGAAGTGAAGACAGATT CTACAGATCACGTAAAACCAAAGGAAACTGAAAACACAAAGCAACCTTCAAAGAGCTGCCATAAACCCA AAGCCATAGTTCATACCGAGAAGGTGAACATGTAA

Fig. 15D

*RSQPHTKP*SVFVMKNGTNVACLVKEFYPKDIRINLVSSKKITEFDPAIVISPSGKYNAVKLGKYEDSNSVTCS VQHDNKTVHSTDFEVKTDSTDHVKPKETENTKQPSKSCHKPKAIVHTEKVNM•

Fig. 16A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaacca*GATGGTAATGAAGAAATGG*
*GTGGTATTACA*CAGACACCATATAAAGTCTCCATCTCTGGAACCACAGTAATATTGACATGCCCTCAGT
ATCCTGGATCTGAAATACTATGGCAACACAATGATAAAAACATAGGCGGTGATGAGGATGATAAAAA
CATAGGCAGTGATGAGGATCACCTGTCACTGAAGGAATTTTCAGAATTGGAGCAAAGTGGTTATTAT
GTCTGCTACCCCAGAGGAAGCAAACCAGAAGATGCGAACTTTTATCTCTACCTGAGGGCAAGAGTGTG
TGAGAACTGCATGGAGATGGATTGA

Fig. 16B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkve*
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprep*DGNEEMGGIT*QTPYKVSISGTTVILTCPQYPGSE
ILWQHNDKNIGGDEDDKNIGSDEDHLSLKEFSELEQSGYYVCYPRGSKPEDANFYLYLRARVCENCMEMD
•

Fig. 16C

*GATGGTAATGAAGAAATGGGTGGTATTACA*CAGACACCATATAAAGTCTCCATCTCTGGAACCACAGT
AATATTGACATGCCCTCAGTATCCTGGATCTGAAATACTATGGCAACACAATGATAAAAACATAGGCG
GTGATGAGGATGATAAAAACATAGGCAGTGATGAGGATCACCTGTCACTGAAGGAATTTTCAGAATT
GGAGCAAAGTGGTTATTATGTCTGCTACCCCAGAGGAAGCAAACCAGAAGATGCGAACTTTTATCTCT
ACCTGAGGGCAAGAGTGTGTGAGAACTGCATGGAGATGGATTGA

Fig. 16D

*DGNEEMGGIT*QTPYKVSISGTTVILTCPQYPGSEILWQHNDKNIGGDEDDKNIGSDEDHLSLKEFSELEQSG
YYVCYPRGSKPEDANFYLYLRARVCENCMEMD•

Fig. 17A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaagt*tgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaaccaCAGTCAATCAAAGGAAACC
ACTTGGTTAAGGTGTATGACTATCAAGAAGATGGTTCGGTACTTCTGACTTGTGATGCAGAAGCCAAA
AATATCACATGGTTTAAAGATGGGAAGATGATCGGCTTCCTAACTGAAGATAAAAAAAAATGGAATC
TGGGAAGTAATGCCAAGGACCCTCGAGGGATGTATCAGTGTAAAGGATCACAGAACAAGTCAAAACC
ACTCCAAGTGTATTACAGAATGTGTCAGAACTGCATTGAACTAAATGCAGCCACCATATCTTGA

Fig. 17B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkve*
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprepQSIKGNHLVKVYDYQEDGSVLLTCDAEAKNITW
FKDGKMIGFLTEDKKKWNLGSNAKDPRGMYQCKGSQNKSKPLQVYYRMCQNCIELNAATIS•

Fig. 17C

**CAGTCAATCAAAGGAAACCACTTGGTTAAGGTGTATGACTATCAAGAAGATGGTTCGGTACTTCTGAC
TTGTGATGCAGAAGCCAAAAATATCACATGGTTTAAAGATGGGAAGATGATCGGCTTCCTAACTGAA
GATAAAAAAAAATGGAATCTGGGAAGTAATGCCAAGGACCCTCGAGGGATGTATCAGTGTAAAGGA
TCACAGAACAAGTCAAAACCACTCCAAGTGTATTACAGAATG**TGTCAGAACTGCATTGAACTAAATGC
AGCCACCATATCTTGA

Fig. 17D

**QSIKGNHLVKVYDYQEDGSVLLTCDAEAKNITWFKDGKMIGFLTEDKKKWNLGSNAKDPRGMYQCKGS
QNKSKPLQVYYRM**CQNCIELNAATIS•

Fig. 18A atggagttgggactgagctggattttccttttggctattttaaaaggtgtccagtgtGAAGTCCAGCTTGTAGAATCAGGGGG
GGGCCTTGTTCAACCCGGCAGATCACTCAGGCTTTCTTGTGCCGCCTCTGGGTTCACCTTCGATGACTAC
GCTATGCACTGGGTCAGACAAGCGCCGGGCAAGGGCCTTGAGTGGGTTTCTGCTATCACATGGAATTCT
GGACACATCGACTACGCCGATTCCGTTGAGGGTAGGTTTACTATTAGTCGGGATAACGCGAAGAACAGC
CTCTACCTTCAAATGAATTCATTGAGGGCGGAGGACACTGCGGTTTACTATTGCGCAAAAGTAAGTTACT
TGAGCACCGCATCTTCACTGGATTACTGGGGCCAGGGAACATTGGTGACAGTATCCTCA*gcctccaccaagg*
*gcccatcggtcttccccctggcaccctcctccaagagcacctctgggggcacagcggccctgggctgcctggtcaaggactacttccc*
*cgaaccggtgacggtgtcgtggaactcaggcgccctgaccagcggcgtgcacaccttcccggctgtcctacagtcctcaggactcta*
*ctccctcagcagcgtggtgaccgtgccctccagcagcttgggcacccagacctacatctgcaacgtgaatcacaagcccagcaaca*
*ccaaggtggacaagaaag*ttgagcccaaatcttgtgacaaaactcacacatgcccaccgtgcccagcacctgaactcctggggggac
cgtcagtcttcctcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggaggagcagtac
aacagcacgtaccgggtggtcagcgtcctcaccgtcctgcaccaggactggctgaatggcaaggagtacaagtgcaaggtctccaaca
aagccctcccagcccccatcgagaaaaccatctccaaagccaaagggcagccccgagaaccaAAGATACCTATAGAGGAAC
TTGAGGACAGAGTGTTTGTGAATTGCAATACCAGCATCACATGGGTAGAGGGAACGGTGGGAACACT
GCTCTCAGACATTACAAGACTGGACCTGGGAAAACGCATCCTGGACCCACGAGGAATATATAGGTGT
AATGGGACAGATATATACAAGGACAAAGAATCTACCGTGCAAGTTCATTATCGAATGTGCCAGAGCT
GTGTGGAGCTGGATTGA

Fig. 18B melglswifllailkgvqcEVQLVESGGGLVQPGRSLRLSCAASGFTFDDYAMHWVRQAPGKGLEWVSAITWNS
GHIDYADSVEGRFTISRDNAKNSLYLQMNSLRAEDTAVYYCAKVSYLSTASSLDYWGQGTLVTVSS*astkgpsv*
*fplapsskstsggtaalgclvkdyfpepvtvswnsgaltsgvhtfpavlqssglyslssvvtvpssslgtqtyicnvnhkpsntkvdkkve*
pkscdkthtcppcpapellggpsvflfppkpkdtlmisrtpevtcvvvdvshedpevkfnwyvdgvevhnaktkpreeqynsty
rvvsvltvlhqdwlngkeykckvsnkalpapiektiskakgqprepKIPIEELEDRVFVNCNTSITWVEGTVGTLLSDITR
LDLGKRILDPRGIYRCNGTDIYKDKESTVQVHYRMCQSCVELD•

Fig. 18C

**AAGATACCTATAGAGGAACTTGAGGACAGAGTGTTTGTGAATTGCAATACCAGCATCACATGGGTAG
AGGGAACGGTGGGAACACTGCTCTCAGACATTACAAGACTGGACCTGGGAAAACGCATCCTGGACCC
ACGAGGAATATATAGGTGTAATGGGACAGATATATACAAGGACAAAGAATCTACCGTGCAAGTTCAT
TATCGAATGTGCCAG**AGCTGTGTGGAGCTGGATTGA

Fig. 18D

KIPIEELEDRVFVNCNTSITWVEGTVGTLLSDITRLDLGKRILDPRGIYRCNGTDIYKDKESTVQVHYRMCQS
CVELD•

Gel 3
Marker
Lane 1: N1
Lane 2: N1
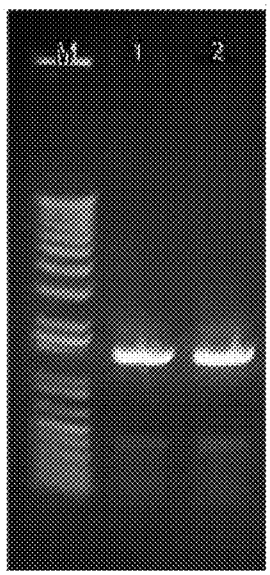
Gel 4
Lane 1: N2
Lane 2: N2
Lane 3: N3
Lane 4: N3
Lane 5: N4
Lane 6: N4
Lane 7: N5
Marker
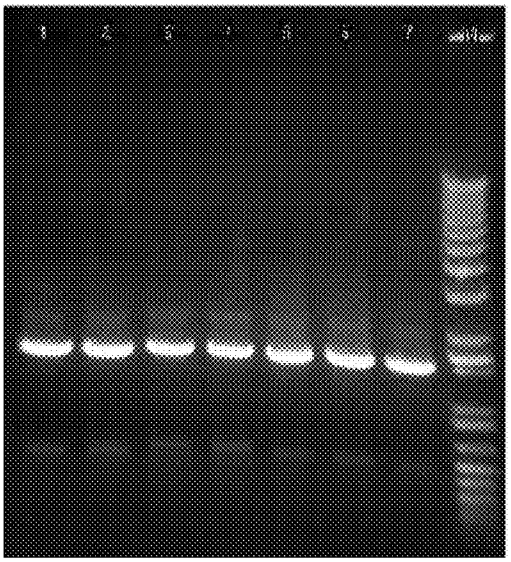
Gel 5
Marker
Lane 1: N5
Lane 2: N6
Lane 3: N6
Lane 4: N7
Lane 5: N7
Lane 6: N8
Lane 7:N8
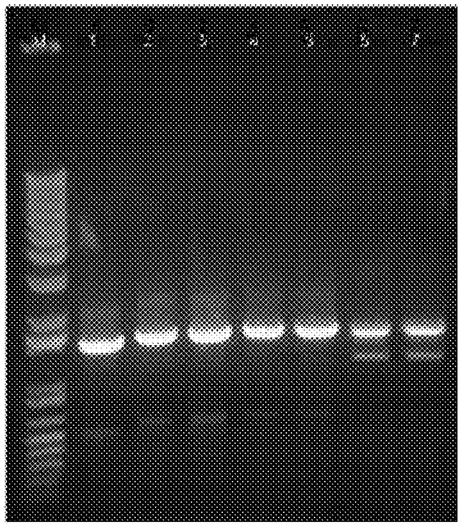
Gel 6
Lane 1: N9
Lane 2: N9
Lane 3: N10
Lane 4: N10
Lane 5: N11
Lane 6: N11
Lane 7:
Marker
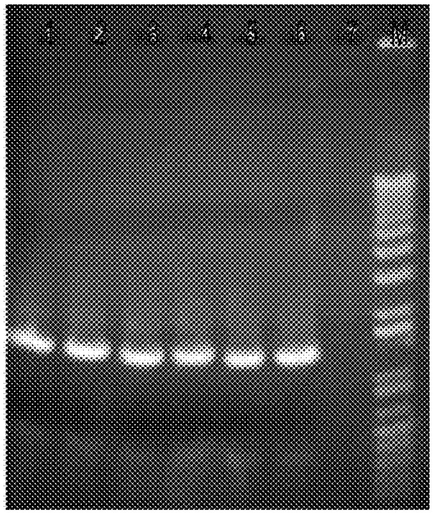
Fig. 22

SEQUENCE LISTING

<160> NUMBER OF SEQ ID NOS: 106

<210> SEQ ID NO 1
<211> LENGTH: 711
<212> TYPE: DNA
<213> ORGANISM: Artificial sequence
<220> FEATURE:
<223> OTHER INFORMATION: Synthesized

<400> SEQUENCE: 1

```
atggacatga gggtccccgc tcagctcctg gggctcctgc tgctctggct cccaggtgcc      60

aaatgtgaca tccagatgac ccagtccccc tcctccctgt ccgcctccgt gggcgaccgc     120

gtgaccatca cctgccgcgc ctcccagggc atccgcaact acctggcctg gtaccagcag     180

aagcccggca aggcccccaa gctgctgatc tacgccgcct ccaccctgca gtccggcgtg     240

ccctcccgct tctccggctc cggctccggc accgacttca ccctgaccat ctcctccctg     300

cagcccgagg acgtggccac ctactactgc cagcgctaca accgcgcccc ctacaccttc     360

ggccagggca ccaaggtgga gatcaagcgc accgtggccg ccccctccgt gttcatcttc     420

ccccctccg acgagcagct gaagtccggc accgcctccg tggtgtgcct gctgaacaac     480

ttctaccccc gcgaggccaa ggtgcagtgg aaggtggaca acgccctgca gtccggcaac     540

tcccaggagt ccgtgaccga gcaggactcc aaggactcca cctactccct gtcctccacc     600

ctgaccctgt ccaaggccga ctacgagaag cacaaggtgt acgcctgcga ggtgacccac     660

cagggcctgt cctcccccgt gaccaagtcc ttcaaccgcg gcgagtgcta g              711
```

<210> SEQ ID NO 2
<211> LENGTH: 236
<212> TYPE: PRT
<213> ORGANISM: Artificial sequence
<220> FEATURE:
<223> OTHER INFORMATION: Synthesized

<400> SEQUENCE: 2

```
Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Tyr Leu Ala Trp Tyr Gln Gln Lys Pro Gly Lys
    50                  55                  60

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Val Ala Thr Tyr Tyr Cys Gln Arg
            100                 105                 110

Tyr Asn Arg Ala Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

```
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 3
<211> LENGTH: 1413
<212> TYPE: DNA
<213> ORGANISM: Artificial Sequence
<220> FEATURE:
<223> OTHER INFORMATION: Synthesized

<400> SEQUENCE: 3

atggagttgg gactgagctg gattttcctt ttggctattt taaaaggtgt ccagtgtgaa     60

gtccagcttg tagaatcagg ggggggcctt gttcaacccg gcagatcact caggctttct    120

tgtgccgcct ctgggttcac cttcgatgac tacgctatgc actgggtcag acaagcgccg    180

ggcaagggcc ttgagtgggt ttctgctatc acatggaatt ctggacacat cgactacgcc    240

gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccacag gtgtacaccc tgcccccatc ccgggatgag   1140

ctgaccaaga accaggtcag cctgacctgc ctggtcaaag gcttctatcc cagcgacatc   1200

gccgtggagt gggagagcaa tgggcagccg gagaacaact acaagaccac gcctcccgtg   1260

ctggactccg acggctcctt cttcctctac agcaagctca ccgtggacaa gagcaggtgg   1320

cagcagggga acgtcttctc atgctccgtg atgcatgagg ctctgcacaa ccactacacg   1380

cagaagagcc tctccctgtc tccgggtaaa tga                                1413


<210> SEQ ID NO 4
<211> LENGTH: 470
<212> TYPE: PRT
<213> ORGANISM: Artificial Sequence
<220> FEATURE:
<223> OTHER INFORMATION: Synthesized

<400> SEQUENCE: 4
```

-continued

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

-continued

```
Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 5
<211> LENGTH: 1404
<212> TYPE: DNA
<213> ORGANISM: Artificial Sequence
<220> FEATURE:
<223> OTHER INFORMATION: Synthesized

<400> SEQUENCE: 5

```
atggagttgg gactgagctg gattttcctt ttggctattt taaaaggtgt ccagtgtgaa     60

gtccagcttg tagaatcagg ggggggcctt gttcaacccg gcagatcact caggcttttct   120

tgtgccgcct ctgggttcac cttcgatgac tacgctatgc actgggtcag acaagcgccg    180

ggcaagggcc ttgagtgggt ttctgctatc acatggaatt ctggacacat cgactacgcc    240

gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccagag acgctgcagc gcacggacgc ccccaaaacg   1140

catatgactc accacgctgt ctctgaccat gaagccaccc tgaggtgctg ggccctgagc   1200

ttctaccctg cggagatcac actgacctgg cagcgggatg gggaggacca gacccaggac   1260

acggagctcg tggagaccag gcctgcaggg gatggaacct tccagaagtg ggtggctgtg   1320

gtggtgcctt ctggacagga gcagagatac acctgccatg tgcagcatga gggtttgccc   1380

aagcccctca ccctgagatg gtga                                          1404
```

<210> SEQ ID NO 6
<211> LENGTH: 467
<212> TYPE: PRT
<213> ORGANISM: Artificial Sequence
<220> FEATURE:
<223> OTHER INFORMATION: Synthesized

<400> SEQUENCE: 6

-continued

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Glu Thr Leu Gln Arg Thr Asp Ala Pro Lys Thr His Met Thr His
    370                 375                 380

His Ala Val Ser Asp His Glu Ala Thr Leu Arg Cys Trp Ala Leu Ser
385                 390                 395                 400

Phe Tyr Pro Ala Glu Ile Thr Leu Thr Trp Gln Arg Asp Gly Glu Asp
                405                 410                 415
```

Gln Thr Gln Asp Thr Glu Leu Val Glu Thr Arg Pro Ala Gly Asp Gly
            420                 425                 430

Thr Phe Gln Lys Trp Val Ala Val Val Val Pro Ser Gly Gln Glu Gln
        435                 440                 445

Arg Tyr Thr Cys His Val Gln His Glu Gly Leu Pro Lys Pro Leu Thr
    450                 455                 460

Leu Arg Trp
465

<210> SEQ ID NO 7
<211> LENGTH: 297
<212> TYPE: DNA
<213> ORGANISM: Artificial Sequence
<220> FEATURE:
<223> OTHER INFORMATION: Synthesized

<400> SEQUENCE: 7
gagacgctgc agcgcacgga cgcccccaaa acgcatatga ctcaccacgc tgtctctgac 60
catgaagcca ccctgaggtg ctgggccctg agcttctacc ctgcggagat cacactgacc 120
tggcagcggg atggggagga ccagacccag gacacggagc tcgtggagac caggcctgca 180
ggggatggaa ccttccagaa gtgggtggct gtggtggtgc cttctggaca ggagcagaga 240
tacacctgcc atgtgcagca tgagggtttg cccaagcccc tcaccctgag atggtga 297

<210> SEQ ID NO 8
<211> LENGTH: 98
<212> TYPE: PRT
<213> ORGANISM: Artificial Sequence
<220> FEATURE:
<223> OTHER INFORMATION: Synthesized

<400> SEQUENCE: 8

Glu Thr Leu Gln Arg Thr Asp Ala Pro Lys Thr His Met Thr His His
1               5                   10                  15

Ala Val Ser Asp His Glu Ala Thr Leu Arg Cys Trp Ala Leu Ser Phe
            20                  25                  30

Tyr Pro Ala Glu Ile Thr Leu Thr Trp Gln Arg Asp Gly Glu Asp Gln
        35                  40                  45

Thr Gln Asp Thr Glu Leu Val Glu Thr Arg Pro Ala Gly Asp Gly Thr
    50                  55                  60

Phe Gln Lys Trp Val Ala Val Val Val Pro Ser Gly Gln Glu Gln Arg
65                  70                  75                  80

Tyr Thr Cys His Val Gln His Glu Gly Leu Pro Lys Pro Leu Thr Leu
                85                  90                  95

Arg Trp

<210> SEQ ID NO 9
<211> LENGTH: 1407
<212> TYPE: DNA
<213> ORGANISM: Artificial Sequence
<220> FEATURE:
<223> OTHER INFORMATION: Synthesized

<400> SEQUENCE: 9
atggagttgg gactgagctg gattttcctt ttggctattt taaaaggtgt ccagtgtgaa 60
gtccagcttg tagaatcagg ggggggcctt gttcaacccg gcagatcact caggctttct 120
tgtgccgcct ctgggttcac cttcgatgac tacgctatgc actgggtcag acaagcgccg 180
ggcaagggcc ttgagtgggt ttctgctatc acatggaatt ctggacacat cgactacgcc 240

-continued

```
gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccaatc cagcgtactc caaagattca ggtttactca   1140

cgtcatccag cagagaatgg aaagtcaaat ttcctgaatt gctatgtgtc tgggtttcat   1200

ccatccgaca ttgaagttga cttactgaag aatggagaga gaattgaaaa agtggagcat   1260

tcagacttgt ctttcagcaa ggactggtct ttctatctct tgtactacac tgaattcacc   1320

cccactgaaa aagatgagta tgcctgccgt gtgaaccatg tgactttgtc acagcccaag   1380

atagttaagt gggatcgaga catgtaa                                       1407
```

<210> SEQ ID NO 10
<211> LENGTH: 468
<212> TYPE: PRT
<213> ORGANISM: Artificial Sequence
<220> FEATURE:
<223> OTHER INFORMATION: Synthesized

<400> SEQUENCE: 10

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
```

-continued

```
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Ile Gln Arg Thr Pro Lys Ile Gln Val Tyr Ser Arg His Pro Ala
    370                 375                 380

Glu Asn Gly Lys Ser Asn Phe Leu Asn Cys Tyr Val Ser Gly Phe His
385                 390                 395                 400

Pro Ser Asp Ile Glu Val Asp Leu Leu Lys Asn Gly Glu Arg Ile Glu
                405                 410                 415

Lys Val Glu His Ser Asp Leu Ser Phe Ser Lys Asp Trp Ser Phe Tyr
            420                 425                 430

Leu Leu Tyr Tyr Thr Glu Phe Thr Pro Thr Glu Lys Asp Glu Tyr Ala
        435                 440                 445

Cys Arg Val Asn His Val Thr Leu Ser Gln Pro Lys Ile Val Lys Trp
    450                 455                 460

Asp Arg Asp Met
465
```

<210> SEQ ID NO 11
<211> LENGTH: 300
<212> TYPE: DNA
<213> ORGANISM: Artificial Sequence
<220> FEATURE:
<223> OTHER INFORMATION: Synthesized

<400> SEQUENCE: 11

```
atccagcgta ctccaaagat tcaggtttac tcacgtcatc cagcagagaa tggaaagtca     60

aatttcctga attgctatgt gtctgggttt catccatccg acattgaagt tgacttactg    120

aagaatggag agagaattga aaaagtggag cattcagact tgtctttcag caaggactgg    180

tctttctatc tcttgtacta cactgaattc acccccactg aaaaagatga gtatgcctgc    240
```

cgtgtgaacc atgtgacttt gtcacagccc aagatagtta agtgggatcg agacatgtaa 300

<210> SEQ ID NO 12
<211> LENGTH: 99
<212> TYPE: PRT
<213> ORGANISM: Artificial Sequence
<220> FEATURE:
<223> OTHER INFORMATION: Synthesized

<400> SEQUENCE: 12

Ile Gln Arg Thr Pro Lys Ile Gln Val Tyr Ser Arg His Pro Ala Glu
1 5 10 15

Asn Gly Lys Ser Asn Phe Leu Asn Cys Tyr Val Ser Gly Phe His Pro
20 25 30

Ser Asp Ile Glu Val Asp Leu Leu Lys Asn Gly Glu Arg Ile Glu Lys
35 40 45

Val Glu His Ser Asp Leu Ser Phe Ser Lys Asp Trp Ser Phe Tyr Leu
50 55 60

Leu Tyr Tyr Thr Glu Phe Thr Pro Thr Glu Lys Asp Glu Tyr Ala Cys
65 70 75 80

Arg Val Asn His Val Thr Leu Ser Gln Pro Lys Ile Val Lys Trp Asp
85 90 95

Arg Asp Met

<210> SEQ ID NO 13
<211> LENGTH: 1449
<212> TYPE: DNA
<213> ORGANISM: Artificial Sequence
<220> FEATURE:
<223> OTHER INFORMATION: Synthesized

<400> SEQUENCE: 13
atggagttgg gactgagctg gattttcctt ttggctattt taaaaggtgt ccagtgtgaa 60
gtccagcttg tagaatcagg ggggggcctt gttcaacccg gcagatcact caggctttct 120
tgtgccgcct ctgggttcac cttcgatgac tacgctatgc actgggtcag acaagcgccg 180
ggcaagggcc ttgagtgggt ttctgctatc acatggaatt ctggacacat cgactacgcc 240
gattccgttg agggtaggtt tactattagt cgggataacg cgaagaacag cctctacctt 300
caaatgaatt cattgagggc ggaggacact gcggtttact attgcgcaaa agtaagttac 360
ttgagcaccg catcttcact ggattactgg ggccagggaa cattggtgac agtatcctca 420
gcctccacca agggcccatc ggtcttcccc ctggcaccct cctccaagag cacctctggg 480
ggcacagcgg ccctgggctg cctggtcaag gactacttcc ccgaaccggt gacggtgtcg 540
tggaactcag gcgccctgac cagcggcgtg cacaccttcc cggctgtcct acagtcctca 600
ggactctact ccctcagcag cgtggtgacc gtgccctcca gcagcttggg cacccagacc 660
tacatctgca acgtgaatca caagcccagc aacaccaagg tggacaagaa agttgagccc 720
aaatcttgtg acaaaactca cacatgccca ccgtgcccag cacctgaact cctgggggga 780
ccgtcagtct tcctcttccc cccaaaaccc aaggacaccc tcatgatctc ccggacccct 840
gaggtcacat gcgtggtggt ggacgtgagc cacgaagacc ctgaggtcaa gttcaactgg 900
tacgtggacg gcgtggaggt gcataatgcc aagacaaagc cgcgggagga gcagtacaac 960
agcacgtacc gggtggtcag cgtcctcacc gtcctgcacc aggactggct gaatggcaag 1020
gagtacaagt gcaaggtctc caacaaagcc ctcccagccc ccatcgagaa aaccatctcc 1080

-continued

```
aaagccaaag ggcagccccg agaaccaact ccgatcacca atgtacctcc agaggtaact   1140

gtgctcacaa acagccctgt ggaactgaga gagcccaacg tcctcatctg tttcatagac   1200

aagttcaccc caccagtggt caatgtcacg tggcttcgaa atggaaaacc tgtcaccaca   1260

ggagtgtcag agacagtctt cctgcccagg gaagaccacc ttttccgcaa gttccactat   1320

ctccccttcc tgccctcaac tgaggacgtt tacgactgca gggtggagca ctggggcttg   1380

gatgagcctc ttctcaagca ctgggagttt gatgctccaa gccctctccc agagactaca   1440

gagaactaa                                                           1449


<210> SEQ ID NO 14
<211> LENGTH: 482
<212> TYPE: PRT
<213> ORGANISM: Artificial Sequence
<220> FEATURE:
<223> OTHER INFORMATION: Synthesized

<400> SEQUENCE: 14

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
```

```
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Thr Pro Ile Thr Asn Val Pro Pro Glu Val Thr Val Leu Thr Asn
    370                 375                 380

Ser Pro Val Glu Leu Arg Glu Pro Asn Val Leu Ile Cys Phe Ile Asp
385                 390                 395                 400

Lys Phe Thr Pro Pro Val Val Asn Val Thr Trp Leu Arg Asn Gly Lys
                405                 410                 415

Pro Val Thr Thr Gly Val Ser Glu Thr Val Phe Leu Pro Arg Glu Asp
            420                 425                 430

His Leu Phe Arg Lys Phe His Tyr Leu Pro Phe Leu Pro Ser Thr Glu
        435                 440                 445

Asp Val Tyr Asp Cys Arg Val Glu His Trp Gly Leu Asp Glu Pro Leu
    450                 455                 460

Leu Lys His Trp Glu Phe Asp Ala Pro Ser Pro Leu Pro Glu Thr Thr
465                 470                 475                 480

Glu Asn


<210> SEQ ID NO 15
<211> LENGTH: 342
<212> TYPE: DNA
<213> ORGANISM: Artificial Sequence
<220> FEATURE:
<223> OTHER INFORMATION: Synthesized

<400> SEQUENCE: 15

actccgatca ccaatgtacc tccagaggta actgtgctca caaacagccc tgtggaactg      60

agagagccca acgtcctcat ctgtttcata gacaagttca ccccaccagt ggtcaatgtc     120

acgtggcttc gaaatggaaa acctgtcacc acaggagtgt cagagacagt cttcctgccc     180

agggaagacc accttttccg caagttccac tatctcccct tcctgccctc aactgaggac     240

gtttacgact gcagggtgga gcactggggc ttggatgagc ctcttctcaa gcactgggag     300

tttgatgctc caagccctct cccagagact acagagaact aa                        342


<210> SEQ ID NO 16
<211> LENGTH: 113
<212> TYPE: PRT
<213> ORGANISM: Artificial Sequence
<220> FEATURE:
<223> OTHER INFORMATION: Synthesized

<400> SEQUENCE: 16

Thr Pro Ile Thr Asn Val Pro Pro Glu Val Thr Val Leu Thr Asn Ser
1               5                   10                  15

Pro Val Glu Leu Arg Glu Pro Asn Val Leu Ile Cys Phe Ile Asp Lys
            20                  25                  30

Phe Thr Pro Pro Val Val Asn Val Thr Trp Leu Arg Asn Gly Lys Pro
        35                  40                  45

Val Thr Thr Gly Val Ser Glu Thr Val Phe Leu Pro Arg Glu Asp His
```

```
    50                  55                  60

Leu Phe Arg Lys Phe His Tyr Leu Pro Phe Leu Pro Ser Thr Glu Asp
65                  70                  75                  80

Val Tyr Asp Cys Arg Val Glu His Trp Gly Leu Asp Glu Pro Leu Leu
                85                  90                  95

Lys His Trp Glu Phe Asp Ala Pro Ser Pro Leu Pro Glu Thr Thr Glu
            100                 105                 110

Asn
```

<210> SEQ ID NO 17
<211> LENGTH: 1434
<212> TYPE: DNA
<213> ORGANISM: Artificial Sequence
<220> FEATURE:
<223> OTHER INFORMATION: Synthesized

<400> SEQUENCE: 17

```
atggagttgg gactgagctg gattttcctt ttggctattt taaaaggtgt ccagtgtgaa     60

gtccagcttg tagaatcagg ggggggcctt gttcaacccg gcagatcact caggctttct    120

tgtgccgcct ctgggttcac cttcgatgac tacgctatgc actgggtcag acaagcgccg    180

ggcaagggcc ttgagtgggt ttctgctatc acatggaatt ctggacacat cgactacgcc    240

gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccacga gtccaaccta aggtgactgt atatccttca   1140

aagacccagc ccctgcagca ccacaacctc ctggtctgct ctgtgagtgg tttctatcca   1200

ggcagcattg aagtcaggtg gttcctgaac ggccaggaag agaaggctgg gatggtgtcc   1260

acaggcctga tccagaatgg agactggacc ttccagaccc tggtgatgct ggaaacagtt   1320

cctcgaagtg gagaggttta cacctgccaa gtggagcacc caagcgtgac aagccctctc   1380

acagtggaat ggagagcacg gtctgaatct gcacagagca agatgctgag ttga          1434
```

<210> SEQ ID NO 18
<211> LENGTH: 477
<212> TYPE: PRT
<213> ORGANISM: Artificial Sequence
<220> FEATURE:
<223> OTHER INFORMATION: Synthesized

<400> SEQUENCE: 18

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Arg Val Gln Pro Lys Val Thr Val Tyr Pro Ser Lys Thr Gln Pro
    370                 375                 380

Leu Gln His His Asn Leu Leu Val Cys Ser Val Ser Gly Phe Tyr Pro
385                 390                 395                 400

Gly Ser Ile Glu Val Arg Trp Phe Leu Asn Gly Gln Glu Glu Lys Ala
                405                 410                 415
```

Gly Met Val Ser Thr Gly Leu Ile Gln Asn Gly Asp Trp Thr Phe Gln
420 425 430

Thr Leu Val Met Leu Glu Thr Val Pro Arg Ser Gly Glu Val Tyr Thr
435 440 445

Cys Gln Val Glu His Pro Ser Val Thr Ser Pro Leu Thr Val Glu Trp
450 455 460

Arg Ala Arg Ser Glu Ser Ala Gln Ser Lys Met Leu Ser
465 470 475

<210> SEQ ID NO 19
<211> LENGTH: 327
<212> TYPE: DNA
<213> ORGANISM: Artificial Sequence
<220> FEATURE:
<223> OTHER INFORMATION: Synthesized

<400> SEQUENCE: 19
cgagtccaac ctaaggtgac tgtatatcct tcaaagaccc agcccctgca gcaccacaac 60
ctcctggtct gctctgtgag tggtttctat ccaggcagca ttgaagtcag gtggttcctg 120
aacggccagg aagagaaggc tgggatggtg tccacaggcc tgatccagaa tggagactgg 180
accttccaga ccctggtgat gctggaaaca gttcctcgaa gtggagaggt ttacacctgc 240
caagtggagc acccaagcgt gacaagccct ctcacagtgg aatggagagc acggtctgaa 300
tctgcacaga gcaagatgct gagttga 327

<210> SEQ ID NO 20
<211> LENGTH: 108
<212> TYPE: PRT
<213> ORGANISM: Artificial Sequence
<220> FEATURE:
<223> OTHER INFORMATION: Synthesized

<400> SEQUENCE: 20

Arg Val Gln Pro Lys Val Thr Val Tyr Pro Ser Lys Thr Gln Pro Leu
1 5 10 15

Gln His His Asn Leu Leu Val Cys Ser Val Ser Gly Phe Tyr Pro Gly
20 25 30

Ser Ile Glu Val Arg Trp Phe Leu Asn Gly Gln Glu Glu Lys Ala Gly
35 40 45

Met Val Ser Thr Gly Leu Ile Gln Asn Gly Asp Trp Thr Phe Gln Thr
50 55 60

Leu Val Met Leu Glu Thr Val Pro Arg Ser Gly Glu Val Tyr Thr Cys
65 70 75 80

Gln Val Glu His Pro Ser Val Thr Ser Pro Leu Thr Val Glu Trp Arg
85 90 95

Ala Arg Ser Glu Ser Ala Gln Ser Lys Met Leu Ser
100 105

<210> SEQ ID NO 21
<211> LENGTH: 1434
<212> TYPE: DNA
<213> ORGANISM: Artificial Sequence
<220> FEATURE:
<223> OTHER INFORMATION: Synthesized

<400> SEQUENCE: 21
atggagttgg gactgagctg gattttcctt ttggctattt taaaaggtgt ccagtgtgaa 60
gtccagcttg tagaatcagg ggggggcctt gttcaacccg gcagatcact caggctttct 120

-continued

```
tgtgccgcct ctgggttcac cttcgatgac tacgctatgc actgggtcag acaagcgccg    180

ggcaagggcc ttgagtgggt ttctgctatc acatggaatt ctggacacat cgactacgcc    240

gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccaaat atccagaacc ctgaccctgc cgtgtaccag   1140

ctgagagact ctaaatccag tgacaagtct gtctgcctat tcaccgattt tgattctcaa   1200

acaaatgtgt cacaaagtaa ggattctgat gtgtatatca cagacaaaac tgtgctagac   1260

atgaggtcta tggacttcaa gagcaacagt gctgtggcct ggagcaacaa atctgacttt   1320

gcatgtgcaa acgccttcaa caacagcatt attccagaag acaccttctt ccccagccca   1380

gaaagttcct gtgatgtcaa gctggtcgag aaaagctttg aaacagatac gtga         1434
```

```
<210> SEQ ID NO 22
<211> LENGTH: 477
<212> TYPE: PRT
<213> ORGANISM: Artificial Sequence
<220> FEATURE:
<223> OTHER INFORMATION: Synthesized

<400> SEQUENCE: 22

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125
```

-continued

```
Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Asn Ile Gln Asn Pro Asp Pro Ala Val Tyr Gln Leu Arg Asp Ser
    370                 375                 380

Lys Ser Ser Asp Lys Ser Val Cys Leu Phe Thr Asp Phe Asp Ser Gln
385                 390                 395                 400

Thr Asn Val Ser Gln Ser Lys Asp Ser Asp Val Tyr Ile Thr Asp Lys
                405                 410                 415

Thr Val Leu Asp Met Arg Ser Met Asp Phe Lys Ser Asn Ser Ala Val
            420                 425                 430

Ala Trp Ser Asn Lys Ser Asp Phe Ala Cys Ala Asn Ala Phe Asn Asn
        435                 440                 445

Ser Ile Ile Pro Glu Asp Thr Phe Phe Pro Ser Pro Glu Ser Ser Cys
    450                 455                 460

Asp Val Lys Leu Val Glu Lys Ser Phe Glu Thr Asp Thr
465                 470                 475


<210> SEQ ID NO 23
<211> LENGTH: 327
<212> TYPE: DNA
<213> ORGANISM: Artificial Sequence
<220> FEATURE:
<223> OTHER INFORMATION: Synthesized

<400> SEQUENCE: 23

aatatccaga accctgaccc tgccgtgtac cagctgagag actctaaatc cagtgacaag      60

tctgtctgcc tattcaccga ttttgattct caaacaaatg tgtcacaaag taaggattct     120
```

```
gatgtgtata tcacagacaa aactgtgcta gacatgaggt ctatggactt caagagcaac    180

agtgctgtgg cctggagcaa caaatctgac tttgcatgtg caaacgcctt caacaacagc    240

attattccag aagacacctt cttccccagc ccagaaagtt cctgtgatgt caagctggtc    300

gagaaaagct ttgaaacaga tacgtga                                        327
```

<210> SEQ ID NO 24
<211> LENGTH: 108
<212> TYPE: PRT
<213> ORGANISM: Artificial Sequence
<220> FEATURE:
<223> OTHER INFORMATION: Synthesized

<400> SEQUENCE: 24

```
Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr
            100                 105
```

<210> SEQ ID NO 25
<211> LENGTH: 1503
<212> TYPE: DNA
<213> ORGANISM: Artificial Sequence
<220> FEATURE:
<223> OTHER INFORMATION: Synthesized

<400> SEQUENCE: 25

```
atggagttgg gactgagctg gattttcctt ttggctattt taaaaggtgt ccagtgtgaa     60

gtccagcttg tagaatcagg ggggggcctt gttcaacccg gcagatcact caggcttttct   120

tgtgccgcct ctgggttcac cttcgatgac tacgctatgc actgggtcag acaagcgccg    180

ggcaagggcc ttgagtgggt ttctgctatc acatggaatt ctggacacat cgactacgcc    240

gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900
```

```
tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccactc gaggacctga aaaacgtgtt cccacccgag   1140

gtcgctgtgt ttgagccatc agaagcagag atctcccaca cccaaaaggc cacactggtg   1200

tgcctggcca caggcttcta ccccgaccac gtggagctga gctggtgggt gaatgggaag   1260

gaggtgcaca gtggggtcag cacagacccg cagcccctca aggagcagcc cgccctcaat   1320

gactccagat actgcctgag cagccgcctg agggtctcgg ccaccttctg gcagaacccc   1380

cgcaaccact tccgctgtca agtccagttc tacgggctct cggagaatga cgagtggacc   1440

caggataggg ccaaacctgt cacccagatc gtcagcgccg aggcctgggg tagagcagac   1500

tag                                                                  1503
```

<210> SEQ ID NO 26
<211> LENGTH: 500
<212> TYPE: PRT
<213> ORGANISM: Artificial Sequence
<220> FEATURE:
<223> OTHER INFORMATION: Synthesized

<400> SEQUENCE: 26

```
Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
```

```
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Leu Glu Asp Leu Lys Asn Val Phe Pro Pro Glu Val Ala Val Phe
    370                 375                 380

Glu Pro Ser Glu Ala Glu Ile Ser His Thr Gln Lys Ala Thr Leu Val
385                 390                 395                 400

Cys Leu Ala Thr Gly Phe Tyr Pro Asp His Val Glu Leu Ser Trp Trp
                405                 410                 415

Val Asn Gly Lys Glu Val His Ser Gly Val Ser Thr Asp Pro Gln Pro
            420                 425                 430

Leu Lys Glu Gln Pro Ala Leu Asn Asp Ser Arg Tyr Cys Leu Ser Ser
        435                 440                 445

Arg Leu Arg Val Ser Ala Thr Phe Trp Gln Asn Pro Arg Asn His Phe
    450                 455                 460

Arg Cys Gln Val Gln Phe Tyr Gly Leu Ser Glu Asn Asp Glu Trp Thr
465                 470                 475                 480

Gln Asp Arg Ala Lys Pro Val Thr Gln Ile Val Ser Ala Glu Ala Trp
                485                 490                 495

Gly Arg Ala Asp
            500


<210> SEQ ID NO 27
<211> LENGTH: 396
<212> TYPE: DNA
<213> ORGANISM: Artificial Sequence
<220> FEATURE:
<223> OTHER INFORMATION: Synthesized

<400> SEQUENCE: 27

ctcgaggacc tgaaaaacgt gttcccaccc gaggtcgctg tgtttgagcc atcagaagca      60

gagatctccc acacccaaaa ggccacactg gtgtgcctgg ccacaggctt ctaccccgac     120

cacgtggagc tgagctggtg ggtgaatggg aaggaggtgc acagtggggt cagcacagac     180

ccgcagcccc tcaaggagca gcccgccctc aatgactcca gatactgcct gagcagccgc     240

ctgagggtct cggccacctt ctggcagaac ccccgcaacc acttccgctg tcaagtccag     300

ttctacgggc tctcggagaa tgacgagtgg acccaggata gggccaaacc tgtcacccag     360

atcgtcagcg ccgaggcctg ggtagagca gactag                                396


<210> SEQ ID NO 28
<211> LENGTH: 131
<212> TYPE: PRT
<213> ORGANISM: Artificial Sequence
```

<220> FEATURE:
<223> OTHER INFORMATION: Synthesized

<400> SEQUENCE: 28

Leu Glu Asp Leu Lys Asn Val Phe Pro Pro Glu Val Ala Val Phe Glu
1               5                   10                  15

Pro Ser Glu Ala Glu Ile Ser His Thr Gln Lys Ala Thr Leu Val Cys
            20                  25                  30

Leu Ala Thr Gly Phe Tyr Pro Asp His Val Glu Leu Ser Trp Trp Val
        35                  40                  45

Asn Gly Lys Glu Val His Ser Gly Val Ser Thr Asp Pro Gln Pro Leu
    50                  55                  60

Lys Glu Gln Pro Ala Leu Asn Asp Ser Arg Tyr Cys Leu Ser Ser Arg
65                  70                  75                  80

Leu Arg Val Ser Ala Thr Phe Trp Gln Asn Pro Arg Asn His Phe Arg
                85                  90                  95

Cys Gln Val Gln Phe Tyr Gly Leu Ser Glu Asn Asp Glu Trp Thr Gln
            100                 105                 110

Asp Arg Ala Lys Pro Val Thr Gln Ile Val Ser Ala Glu Ala Trp Gly
        115                 120                 125

Arg Ala Asp
    130

<210> SEQ ID NO 29
<211> LENGTH: 1518
<212> TYPE: DNA
<213> ORGANISM: Artificial Sequence
<220> FEATURE:
<223> OTHER INFORMATION: Synthesized

<400> SEQUENCE: 29
atggagttgg gactgagctg gattttcctt ttggctattt taaaaggtgt ccagtgtgaa 60
gtccagcttg tagaatcagg ggggggcctt gttcaacccg gcagatcact caggctttct 120
tgtgccgcct ctgggttcac cttcgatgac tacgctatgc actgggtcag acaagcgccg 180
ggcaagggcc ttgagtgggt ttctgctatc acatggaatt ctggacacat cgactacgcc 240
gattccgttg agggtaggtt tactattagt cgggataacg cgaagaacag cctctacctt 300
caaatgaatt cattgagggc ggaggacact gcggtttact attgcgcaaa agtaagttac 360
ttgagcaccg catcttcact ggattactgg ggccagggaa cattggtgac agtatcctca 420
gcctccacca agggcccatc ggtcttcccc ctggcaccct cctccaagag cacctctggg 480
ggcacagcgg ccctgggctg cctggtcaag gactacttcc ccgaaccggt gacggtgtcg 540
tggaactcag gcgccctgac cagcggcgtg cacaccttcc cggctgtcct acagtcctca 600
ggactctact ccctcagcag cgtggtgacc gtgccctcca gcagcttggg cacccagacc 660
tacatctgca acgtgaatca caagcccagc aacaccaagg tggacaagaa agttgagccc 720
aaatcttgtg acaaaactca cacatgccca ccgtgcccag cacctgaact cctgggggga 780
ccgtcagtct tcctcttccc cccaaaaccc aaggacaccc tcatgatctc ccggacccct 840
gaggtcacat gcgtggtggt ggacgtgagc cacgaagacc ctgaggtcaa gttcaactgg 900
tacgtggacg gcgtggaggt gcataatgcc aagacaaagc cgcgggagga gcagtacaac 960
agcacgtacc gggtggtcag cgtcctcacc gtcctgcacc aggactggct gaatggcaag 1020
gagtacaagt gcaaggtctc caacaaagcc ctcccagccc ccatcgagaa aaccatctcc 1080
aaagccaaag ggcagccccg agaaccaaca gataaacaac ttgatgcaga tgtttccccc 1140

```
aagcccacta tttttcttcc ttcaattgct gaaacaaagc tccagaaggc tggaacatac   1200

ctttgtcttc ttgagaaatt tttccctgat gttattaaga tacattggga agaaaagaag   1260

agcaacacga ttctgggatc ccaggagggg aacaccatga agactaatga cacatacatg   1320

aaatttagct ggttaacggt gccagaaaag tcactggaca aagaacacag atgtatcgtc   1380

agacatgaga ataataaaaa cggagttgat caagaaatta tctttcctcc aataaagaca   1440

gatgtcatca caatggatcc caaagacaat tgttcaaaag atgcaaatga tacactactg   1500

ctgcagctca caaactaa                                                   1518
```

```
<210> SEQ ID NO 30
<211> LENGTH: 505
<212> TYPE: PRT
<213> ORGANISM: Artificial Sequence
<220> FEATURE:
<223> OTHER INFORMATION: Synthesized

<400> SEQUENCE: 30

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285
```

-continued

```
Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Thr Asp Lys Gln Leu Asp Ala Asp Val Ser Pro Lys Pro Thr Ile
    370                 375                 380

Phe Leu Pro Ser Ile Ala Glu Thr Lys Leu Gln Lys Ala Gly Thr Tyr
385                 390                 395                 400

Leu Cys Leu Leu Glu Lys Phe Phe Pro Asp Val Ile Lys Ile His Trp
                405                 410                 415

Glu Glu Lys Lys Ser Asn Thr Ile Leu Gly Ser Gln Glu Gly Asn Thr
            420                 425                 430

Met Lys Thr Asn Asp Thr Tyr Met Lys Phe Ser Trp Leu Thr Val Pro
        435                 440                 445

Glu Lys Ser Leu Asp Lys Glu His Arg Cys Ile Val Arg His Glu Asn
    450                 455                 460

Asn Lys Asn Gly Val Asp Gln Glu Ile Ile Phe Pro Pro Ile Lys Thr
465                 470                 475                 480

Asp Val Ile Thr Met Asp Pro Lys Asp Asn Cys Ser Lys Asp Ala Asn
                485                 490                 495

Asp Thr Leu Leu Leu Gln Leu Thr Asn
            500                 505


<210> SEQ ID NO 31
<211> LENGTH: 411
<212> TYPE: DNA
<213> ORGANISM: Artificial Sequence
<220> FEATURE:
<223> OTHER INFORMATION: Synthesized

<400> SEQUENCE: 31

acagataaac aacttgatgc agatgtttcc cccaagccca ctatttttct tccttcaatt      60

gctgaaacaa agctccagaa ggctggaaca tacctttgtc ttcttgagaa atttttccct     120

gatgttatta agatacattg ggaagaaaag aagagcaaca cgattctggg atcccaggag     180

gggaacacca tgaagactaa tgacacatac atgaaattta gctggttaac ggtgccagaa     240

aagtcactgg acaaagaaca cagatgtatc gtcagacatg agaataataa aaacggagtt     300

gatcaagaaa ttatctttcc tccaataaag acagatgtca tcacaatgga tcccaaagac     360

aattgttcaa aagatgcaaa tgatacacta ctgctgcagc tcacaaacta a              411


<210> SEQ ID NO 32
<211> LENGTH: 136
<212> TYPE: PRT
<213> ORGANISM: Artificial Sequence
<220> FEATURE:
<223> OTHER INFORMATION: Synthesized

<400> SEQUENCE: 32

Thr Asp Lys Gln Leu Asp Ala Asp Val Ser Pro Lys Pro Thr Ile Phe
1               5                   10                  15
```

```
Leu Pro Ser Ile Ala Glu Thr Lys Leu Gln Lys Ala Gly Thr Tyr Leu
            20                  25                  30

Cys Leu Leu Glu Lys Phe Phe Pro Asp Val Ile Lys Ile His Trp Glu
        35                  40                  45

Glu Lys Lys Ser Asn Thr Ile Leu Gly Ser Gln Glu Gly Asn Thr Met
    50                  55                  60

Lys Thr Asn Asp Thr Tyr Met Lys Phe Ser Trp Leu Thr Val Pro Glu
65                  70                  75                  80

Lys Ser Leu Asp Lys Glu His Arg Cys Ile Val Arg His Glu Asn Asn
                85                  90                  95

Lys Asn Gly Val Asp Gln Glu Ile Ile Phe Pro Pro Ile Lys Thr Asp
            100                 105                 110

Val Ile Thr Met Asp Pro Lys Asp Asn Cys Ser Lys Asp Ala Asn Asp
        115                 120                 125

Thr Leu Leu Leu Gln Leu Thr Asn
    130                 135
```

<210> SEQ ID NO 33
<211> LENGTH: 1485
<212> TYPE: DNA
<213> ORGANISM: Artificial Sequence
<220> FEATURE:
<223> OTHER INFORMATION: Synthesized

<400> SEQUENCE: 33

```
atggagttgg gactgagctg gattttcctt ttggctattt taaaaggtgt ccagtgtgaa     60

gtccagcttg tagaatcagg ggggggcctt gttcaacccg gcagatcact caggctttct    120

tgtgccgcct ctgggttcac cttcgatgac tacgctatgc actgggtcag acaagcgccg    180

ggcaagggcc ttgagtgggt ttctgctatc acatggaatt ctggacacat cgactacgcc    240

gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccaaga agtcagcctc ataccaaacc atccgttttt   1140

gtcatgaaaa atggaacaaa tgtcgcttgt ctggtgaagg aattctaccc caaggatata   1200

agaataaatc tcgtgtcatc caagaagata acagagtttg atcctgctat tgtcatctct   1260

cccagtggga agtacaatgc tgtcaagctt ggtaaatatg aagattcaaa ttcagtgaca   1320

tgttcagttc aacacgacaa taaaactgtg cactccactg actttgaagt gaagacagat   1380
```

tctacagatc acgtaaaacc aaaggaaact gaaaacacaa agcaaccttc aaagagctgc 1440
cataaaccca aagccatagt tcataccgag aaggtgaaca tgtaa 1485

<210> SEQ ID NO 34
<211> LENGTH: 494
<212> TYPE: PRT
<213> ORGANISM: Artificial Sequence
<220> FEATURE:
<223> OTHER INFORMATION: Synthesized

<400> SEQUENCE: 34

Met Glu Leu Gly Leu Ser Trp Ile Phe Leu Leu Ala Ile Leu Lys Gly
1 5 10 15

Val Gln Cys Glu Val Gln Leu Val Glu Ser Gly Gly Gly Leu Val Gln
20 25 30

Pro Gly Arg Ser Leu Arg Leu Ser Cys Ala Ala Ser Gly Phe Thr Phe
35 40 45

Asp Asp Tyr Ala Met His Trp Val Arg Gln Ala Pro Gly Lys Gly Leu
50 55 60

Glu Trp Val Ser Ala Ile Thr Trp Asn Ser Gly His Ile Asp Tyr Ala
65 70 75 80

Asp Ser Val Glu Gly Arg Phe Thr Ile Ser Arg Asp Asn Ala Lys Asn
85 90 95

Ser Leu Tyr Leu Gln Met Asn Ser Leu Arg Ala Glu Asp Thr Ala Val
100 105 110

Tyr Tyr Cys Ala Lys Val Ser Tyr Leu Ser Thr Ala Ser Ser Leu Asp
115 120 125

Tyr Trp Gly Gln Gly Thr Leu Val Thr Val Ser Ser Ala Ser Thr Lys
130 135 140

Gly Pro Ser Val Phe Pro Leu Ala Pro Ser Ser Lys Ser Thr Ser Gly
145 150 155 160

Gly Thr Ala Ala Leu Gly Cys Leu Val Lys Asp Tyr Phe Pro Glu Pro
165 170 175

Val Thr Val Ser Trp Asn Ser Gly Ala Leu Thr Ser Gly Val His Thr
180 185 190

Phe Pro Ala Val Leu Gln Ser Ser Gly Leu Tyr Ser Leu Ser Ser Val
195 200 205

Val Thr Val Pro Ser Ser Ser Leu Gly Thr Gln Thr Tyr Ile Cys Asn
210 215 220

Val Asn His Lys Pro Ser Asn Thr Lys Val Asp Lys Lys Val Glu Pro
225 230 235 240

Lys Ser Cys Asp Lys Thr His Thr Cys Pro Pro Cys Pro Ala Pro Glu
245 250 255

Leu Leu Gly Gly Pro Ser Val Phe Leu Phe Pro Pro Lys Pro Lys Asp
260 265 270

Thr Leu Met Ile Ser Arg Thr Pro Glu Val Thr Cys Val Val Val Asp
275 280 285

Val Ser His Glu Asp Pro Glu Val Lys Phe Asn Trp Tyr Val Asp Gly
290 295 300

Val Glu Val His Asn Ala Lys Thr Lys Pro Arg Glu Glu Gln Tyr Asn
305 310 315 320

Ser Thr Tyr Arg Val Val Ser Val Leu Thr Val Leu His Gln Asp Trp
325 330 335

Leu Asn Gly Lys Glu Tyr Lys Cys Lys Val Ser Asn Lys Ala Leu Pro

```
            340                 345                 350

Ala Pro Ile Glu Lys Thr Ile Ser Lys Ala Lys Gly Gln Pro Arg Glu
        355                 360                 365

Pro Arg Ser Gln Pro His Thr Lys Pro Ser Val Phe Val Met Lys Asn
    370                 375                 380

Gly Thr Asn Val Ala Cys Leu Val Lys Glu Phe Tyr Pro Lys Asp Ile
385                 390                 395                 400

Arg Ile Asn Leu Val Ser Ser Lys Lys Ile Thr Glu Phe Asp Pro Ala
                405                 410                 415

Ile Val Ile Ser Pro Ser Gly Lys Tyr Asn Ala Val Lys Leu Gly Lys
            420                 425                 430

Tyr Glu Asp Ser Asn Ser Val Thr Cys Ser Val Gln His Asp Asn Lys
        435                 440                 445

Thr Val His Ser Thr Asp Phe Glu Val Lys Thr Asp Ser Thr Asp His
    450                 455                 460

Val Lys Pro Lys Glu Thr Glu Asn Thr Lys Gln Pro Ser Lys Ser Cys
465                 470                 475                 480

His Lys Pro Lys Ala Ile Val His Thr Glu Lys Val Asn Met
                485                 490


<210> SEQ ID NO 35
<211> LENGTH: 378
<212> TYPE: DNA
<213> ORGANISM: Artificial Sequence
<220> FEATURE:
<223> OTHER INFORMATION: Synthesized

<400> SEQUENCE: 35

agaagtcagc ctcataccaa accatccgtt tttgtcatga aaaatggaac aaatgtcgct      60

tgtctggtga aggaattcta ccccaaggat ataagaataa atctcgtgtc atccaagaag     120

ataacagagt ttgatcctgc tattgtcatc tctcccagtg ggaagtacaa tgctgtcaag     180

cttggtaaat atgaagattc aaattcagtg acatgttcag ttcaacacga caataaaact     240

gtgcactcca ctgactttga agtgaagaca gattctacag atcacgtaaa accaaaggaa     300

actgaaaaca caaagcaacc ttcaaagagc tgccataaac ccaaagccat agttcatacc     360

gagaaggtga acatgtaa                                                   378


<210> SEQ ID NO 36
<211> LENGTH: 125
<212> TYPE: PRT
<213> ORGANISM: Artificial Sequence
<220> FEATURE:
<223> OTHER INFORMATION: Synthesized

<400> SEQUENCE: 36

Arg Ser Gln Pro His Thr Lys Pro Ser Val Phe Val Met Lys Asn Gly
1               5                   10                  15

Thr Asn Val Ala Cys Leu Val Lys Glu Phe Tyr Pro Lys Asp Ile Arg
            20                  25                  30

Ile Asn Leu Val Ser Ser Lys Lys Ile Thr Glu Phe Asp Pro Ala Ile
        35                  40                  45

Val Ile Ser Pro Ser Gly Lys Tyr Asn Ala Val Lys Leu Gly Lys Tyr
    50                  55                  60

Glu Asp Ser Asn Ser Val Thr Cys Ser Val Gln His Asp Asn Lys Thr
65                  70                  75                  80

Val His Ser Thr Asp Phe Glu Val Lys Thr Asp Ser Thr Asp His Val
```

```
                85                  90                  95

Lys Pro Lys Glu Thr Glu Asn Thr Lys Gln Pro Ser Lys Ser Cys His
            100                 105                 110

Lys Pro Lys Ala Ile Val His Thr Glu Lys Val Asn Met
        115                 120                 125
```

<210> SEQ ID NO 37
<211> LENGTH: 1422
<212> TYPE: DNA
<213> ORGANISM: Artificial Sequence
<220> FEATURE:
<223> OTHER INFORMATION: Synthesized

<400> SEQUENCE: 37

```
atggagttgg gactgagctg gattttcctt ttggctattt taaaaggtgt ccagtgtgaa     60

gtccagcttg tagaatcagg ggggggcctt gttcaacccg gcagatcact caggctttct    120

tgtgccgcct ctgggttcac cttcgatgac tacgctatgc actgggtcag acaagcgccg    180

ggcaagggcc ttgagtgggt ttctgctatc acatggaatt ctggacacat cgactacgcc    240

gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccagat ggtaatgaag aaatgggtgg tattacacag   1140

acaccatata aagtctccat ctctggaacc acagtaatat tgacatgccc tcagtatcct   1200

ggatctgaaa tactatggca acacaatgat aaaaacatag gcggtgatga ggatgataaa   1260

aacataggca gtgatgagga tcacctgtca ctgaaggaat tttcagaatt ggagcaaagt   1320

ggttattatg tctgctaccc cagaggaagc aaaccagaag atgcgaactt ttatctctac   1380

ctgagggcaa gagtgtgtga gaactgcatg gagatggatt ga                      1422
```

<210> SEQ ID NO 38
<211> LENGTH: 473
<212> TYPE: PRT
<213> ORGANISM: Artificial Sequence
<220> FEATURE:
<223> OTHER INFORMATION: Synthesized

<400> SEQUENCE: 38

```
Met Glu Leu Gly Leu Ser Trp Ile Phe Leu Leu Ala Ile Leu Lys Gly
1               5                   10                  15
```

-continued

```
Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Asp Gly Asn Glu Glu Met Gly Gly Ile Thr Gln Thr Pro Tyr Lys
    370                 375                 380

Val Ser Ile Ser Gly Thr Thr Val Ile Leu Thr Cys Pro Gln Tyr Pro
385                 390                 395                 400

Gly Ser Glu Ile Leu Trp Gln His Asn Asp Lys Asn Ile Gly Gly Asp
                405                 410                 415

Glu Asp Asp Lys Asn Ile Gly Ser Asp Glu Asp His Leu Ser Leu Lys
            420                 425                 430

Glu Phe Ser Glu Leu Glu Gln Ser Gly Tyr Tyr Val Cys Tyr Pro Arg
```

```
        435                 440                 445

Gly Ser Lys Pro Glu Asp Ala Asn Phe Tyr Leu Tyr Leu Arg Ala Arg
    450                 455                 460

Val Cys Glu Asn Cys Met Glu Met Asp
465                 470


<210> SEQ ID NO 39
<211> LENGTH: 315
<212> TYPE: DNA
<213> ORGANISM: Artificial Sequence
<220> FEATURE:
<223> OTHER INFORMATION: Synthesized

<400> SEQUENCE: 39

gatggtaatg aagaaatggg tggtattaca cagacaccat ataaagtctc catctctgga      60

accacagtaa tattgacatg ccctcagtat cctggatctg aaatactatg gcaacacaat     120

gataaaaaca taggcggtga tgaggatgat aaaaacatag gcagtgatga ggatcacctg     180

tcactgaagg aattttcaga attggagcaa agtggttatt atgtctgcta ccccagagga     240

agcaaaccag aagatgcgaa cttttatctc tacctgaggg caagagtgtg tgagaactgc     300

atggagatgg attga                                                      315


<210> SEQ ID NO 40
<211> LENGTH: 104
<212> TYPE: PRT
<213> ORGANISM: Artificial Sequence
<220> FEATURE:
<223> OTHER INFORMATION: Synthesized

<400> SEQUENCE: 40

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
            100


<210> SEQ ID NO 41
<211> LENGTH: 1392
<212> TYPE: DNA
<213> ORGANISM: Artificial Sequence
<220> FEATURE:
<223> OTHER INFORMATION: Synthesized

<400> SEQUENCE: 41

atggagttgg gactgagctg gattttcctt ttggctattt taaaaggtgt ccagtgtgaa      60

gtccagcttg tagaatcagg ggggggcctt gttcaacccg gcagatcact caggctttct     120

tgtgccgcct ctgggttcac cttcgatgac tacgctatgc actgggtcag acaagcgccg     180

ggcaagggcc ttgagtgggt ttctgctatc acatggaatt ctggacacat cgactacgcc     240
```

gattccgttg agggtaggtt tactattagt cgggataacg cgaagaacag cctctacctt 300
caaatgaatt cattgagggc ggaggacact gcggtttact attgcgcaaa agtaagttac 360
ttgagcaccg catcttcact ggattactgg ggccagggaa cattggtgac agtatcctca 420
gcctccacca agggcccatc ggtcttcccc ctggcaccct cctccaagag cacctctggg 480
ggcacagcgg ccctgggctg cctggtcaag gactacttcc ccgaaccggt gacggtgtcg 540
tggaactcag gcgccctgac cagcggcgtg cacaccttcc cggctgtcct acagtcctca 600
ggactctact ccctcagcag cgtggtgacc gtgccctcca gcagcttggg cacccagacc 660
tacatctgca acgtgaatca caagcccagc aacaccaagg tggacaagaa agttgagccc 720
aaatcttgtg acaaaactca cacatgccca ccgtgcccag cacctgaact cctgggggga 780
ccgtcagtct tcctcttccc cccaaaaccc aaggacaccc tcatgatctc ccggacccct 840
gaggtcacat gcgtggtggt ggacgtgagc cacgaagacc ctgaggtcaa gttcaactgg 900
tacgtggacg gcgtggaggt gcataatgcc aagacaaagc cgcgggagga gcagtacaac 960
agcacgtacc gggtggtcag cgtcctcacc gtcctgcacc aggactggct gaatggcaag 1020
gagtacaagt gcaaggtctc caacaaagcc ctcccagccc ccatcgagaa aaccatctcc 1080
aaagccaaag ggcagccccg agaaccacag tcaatcaaag gaaaccactt ggttaaggtg 1140
tatgactatc aagaagatgg ttcggtactt ctgacttgtg atgcagaagc caaaaatatc 1200
acatggttta aagatgggaa gatgatcggc ttcctaactg aagataaaaa aaaatggaat 1260
ctgggaagta atgccaagga ccctcgaggg atgtatcagt gtaaaggatc acagaacaag 1320
tcaaaaccac tccaagtgta ttacagaatg tgtcagaact gcattgaact aaatgcagcc 1380
accatatctt ga 1392

<210> SEQ ID NO 42
<211> LENGTH: 463
<212> TYPE: PRT
<213> ORGANISM: Artificial Sequence
<220> FEATURE:
<223> OTHER INFORMATION: Synthesized

<400> SEQUENCE: 42

Met Glu Leu Gly Leu Ser Trp Ile Phe Leu Leu Ala Ile Leu Lys Gly
1 5 10 15

Val Gln Cys Glu Val Gln Leu Val Glu Ser Gly Gly Gly Leu Val Gln
20 25 30

Pro Gly Arg Ser Leu Arg Leu Ser Cys Ala Ala Ser Gly Phe Thr Phe
35 40 45

Asp Asp Tyr Ala Met His Trp Val Arg Gln Ala Pro Gly Lys Gly Leu
50 55 60

Glu Trp Val Ser Ala Ile Thr Trp Asn Ser Gly His Ile Asp Tyr Ala
65 70 75 80

Asp Ser Val Glu Gly Arg Phe Thr Ile Ser Arg Asp Asn Ala Lys Asn
85 90 95

Ser Leu Tyr Leu Gln Met Asn Ser Leu Arg Ala Glu Asp Thr Ala Val
100 105 110

Tyr Tyr Cys Ala Lys Val Ser Tyr Leu Ser Thr Ala Ser Ser Leu Asp
115 120 125

Tyr Trp Gly Gln Gly Thr Leu Val Thr Val Ser Ser Ala Ser Thr Lys
130 135 140

Gly Pro Ser Val Phe Pro Leu Ala Pro Ser Ser Lys Ser Thr Ser Gly
145 150 155 160

```
Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Ser Ile Lys Gly Asn His Leu Val Lys Val Tyr Asp Tyr Gln
    370                 375                 380

Glu Asp Gly Ser Val Leu Leu Thr Cys Asp Ala Glu Ala Lys Asn Ile
385                 390                 395                 400

Thr Trp Phe Lys Asp Gly Lys Met Ile Gly Phe Leu Thr Glu Asp Lys
                405                 410                 415

Lys Lys Trp Asn Leu Gly Ser Asn Ala Lys Asp Pro Arg Gly Met Tyr
            420                 425                 430

Gln Cys Lys Gly Ser Gln Asn Lys Ser Lys Pro Leu Gln Val Tyr Tyr
        435                 440                 445

Arg Met Cys Gln Asn Cys Ile Glu Leu Asn Ala Ala Thr Ile Ser
    450                 455                 460
```

<210> SEQ ID NO 43
<211> LENGTH: 285
<212> TYPE: DNA
<213> ORGANISM: Artificial Sequence
<220> FEATURE:
<223> OTHER INFORMATION: Synthesized

<400> SEQUENCE: 43

```
cagtcaatca aaggaaacca cttggttaag gtgtatgact atcaagaaga tggttcggta     60

cttctgactt gtgatgcaga agccaaaaat atcacatggt ttaaagatgg gaagatgatc    120

ggcttcctaa ctgaagataa aaaaaaatgg aatctgggaa gtaatgccaa ggaccctcga    180

gggatgtatc agtgtaaagg atcacagaac aagtcaaaac cactccaagt gtattacaga    240

atgtgtcaga actgcattga actaaatgca gccaccatat cttga                    285
```

<210> SEQ ID NO 44
<211> LENGTH: 94
<212> TYPE: PRT
<213> ORGANISM: Artificial Sequence
<220> FEATURE:
<223> OTHER INFORMATION: Synthesized

<400> SEQUENCE: 44

```
Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg
65                  70                  75                  80

Met Cys Gln Asn Cys Ile Glu Leu Asn Ala Ala Thr Ile Ser
                85                  90
```

<210> SEQ ID NO 45
<211> LENGTH: 1344
<212> TYPE: DNA
<213> ORGANISM: Artificial Sequence
<220> FEATURE:
<223> OTHER INFORMATION: Synthesized

<400> SEQUENCE: 45

```
atggagttgg gactgagctg gattttcctt ttggctattt taaaaggtgt ccagtgtgaa     60

gtccagcttg tagaatcagg ggggggcctt gttcaacccg gcagatcact caggctttct    120

tgtgccgcct ctgggttcac cttcgatgac tacgctatgc actgggtcag acaagcgccg    180

ggcaagggcc ttgagtgggt ttctgctatc acatggaatt ctggacacat cgactacgcc    240

gattccgttg agggtaggtt tactattagt cgggataacg cgaagaacag cctctacctt    300

caaatgaatt cattgagggc ggaggacact gcggtttact attgcgcaaa agtaagttac    360

ttgagcaccg catcttcact ggattactgg ggccagggaa cattggtgac agtatcctca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccaaag atacctatag aggaacttga ggacagagtg   1140

tttgtgaatt gcaataccag catcacatgg gtagagggaa cggtgggaac actgctctca   1200

gacattacaa gactggacct gggaaaacgc atcctggacc cacgaggaat atataggtgt   1260
```

```
aatgggacag atatatacaa ggacaaagaa tctaccgtgc aagttcatta tcgaatgtgc   1320

cagagctgtg tggagctgga ttga                                          1344


<210> SEQ ID NO 46
<211> LENGTH: 447
<212> TYPE: PRT
<213> ORGANISM: Artificial Sequence
<220> FEATURE:
<223> OTHER INFORMATION: Synthesized

<400> SEQUENCE: 46

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350
```

Ala Pro Ile Glu Lys Thr Ile Ser Lys Ala Lys Gly Gln Pro Arg Glu
355 360 365

Pro Lys Ile Pro Ile Glu Glu Leu Glu Asp Arg Val Phe Val Asn Cys
370 375 380

Asn Thr Ser Ile Thr Trp Val Glu Gly Thr Val Gly Thr Leu Leu Ser
385 390 395 400

Asp Ile Thr Arg Leu Asp Leu Gly Lys Arg Ile Leu Asp Pro Arg Gly
405 410 415

Ile Tyr Arg Cys Asn Gly Thr Asp Ile Tyr Lys Asp Lys Glu Ser Thr
420 425 430

Val Gln Val His Tyr Arg Met Cys Gln Ser Cys Val Glu Leu Asp
435 440 445

<210> SEQ ID NO 47
<211> LENGTH: 237
<212> TYPE: DNA
<213> ORGANISM: Artificial Sequence
<220> FEATURE:
<223> OTHER INFORMATION: Synthesized

<400> SEQUENCE: 47
aagataccta tagaggaact tgaggacaga gtgtttgtga attgcaatac cagcatcaca 60
tgggtagagg gaacggtggg aacactgctc tcagacatta caagactgga cctgggaaaa 120
cgcatcctgg acccacgagg aatatatagg tgtaatggga cagatatata caaggacaaa 180
gaatctaccg tgcaagttca ttatcgaatg tgccagagct gtgtggagct ggattga 237

<210> SEQ ID NO 48
<211> LENGTH: 78
<212> TYPE: PRT
<213> ORGANISM: Artificial Sequence
<220> FEATURE:
<223> OTHER INFORMATION: Synthesized

<400> SEQUENCE: 48

Lys Ile Pro Ile Glu Glu Leu Glu Asp Arg Val Phe Val Asn Cys Asn
1 5 10 15

Thr Ser Ile Thr Trp Val Glu Gly Thr Val Gly Thr Leu Leu Ser Asp
20 25 30

Ile Thr Arg Leu Asp Leu Gly Lys Arg Ile Leu Asp Pro Arg Gly Ile
35 40 45

Tyr Arg Cys Asn Gly Thr Asp Ile Tyr Lys Asp Lys Glu Ser Thr Val
50 55 60

Gln Val His Tyr Arg Met Cys Gln Ser Cys Val Glu Leu Asp
65 70 75

<210> SEQ ID NO 49
<211> LENGTH: 293
<212> TYPE: DNA
<213> ORGANISM: Artificial Sequence
<220> FEATURE:
<223> OTHER INFORMATION: Synthesized

<400> SEQUENCE: 49
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agt 293

<210> SEQ ID NO 50
<211> LENGTH: 98
<212> TYPE: PRT
<213> ORGANISM: Artificial Sequence
<220> FEATURE:
<223> OTHER INFORMATION: Synthesized

<400> SEQUENCE: 50

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 51
<211> LENGTH: 45
<212> TYPE: DNA
<213> ORGANISM: Artificial Sequence
<220> FEATURE:
<223> OTHER INFORMATION: Synthesized

<400> SEQUENCE: 51
tgagcccaaa tcttgtgaca aaactcacac atgcccaccg tgccc 45

<210> SEQ ID NO 52
<211> LENGTH: 15
<212> TYPE: PRT
<213> ORGANISM: Artificial Sequence
<220> FEATURE:
<223> OTHER INFORMATION: Synthesized

<400> SEQUENCE: 52

Glu Pro Lys Ser Cys Asp Lys Thr His Thr Cys Pro Pro Cys Pro
1 5 10 15

<210> SEQ ID NO 53
<211> LENGTH: 331
<212> TYPE: DNA
<213> ORGANISM: Artificial Sequence
<220> FEATURE:
<223> OTHER INFORMATION: Synthesized

<400> SEQUENCE: 53
agcacctgaa ctcctggggg gaccgtcagt cttcctcttc cccccaaaac ccaaggacac 60
cctcatgatc tcccggaccc ctgaggtcac atgcgtggtg gtggacgtga gccacgaaga 120
ccctgaggtc aagttcaact ggtacgtgga cggcgtggag gtgcataatg ccaagacaaa 180
gccgcgggag gagcagtaca acagcacgta ccgggtggtc agcgtcctca ccgtcctgca 240
ccaggactgg ctgaatggca aggagtacaa gtgcaaggtc tccaacaaag ccctcccagc 300
ccccatcgag aaaaccatct ccaaagccaa a 331

<210> SEQ ID NO 54
<211> LENGTH: 110
<212> TYPE: PRT
<213> ORGANISM: Artificial Sequence
<220> FEATURE:
<223> OTHER INFORMATION: Synthesized

<400> SEQUENCE: 54

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys
100 105 110

<210> SEQ ID NO 55
<211> LENGTH: 321
<212> TYPE: DNA
<213> ORGANISM: Artificial Sequence
<220> FEATURE:
<223> OTHER INFORMATION: Synthesized

<400> SEQUENCE: 55
gggcagcccc gagaaccaca ggtgtacacc ctgcccccat cccgggatga gctgaccaag 60
aaccaggtca gcctgacctg cctggtcaaa ggcttctatc ccagcgacat cgccgtggag 120
tgggagagca atgggcagcc ggagaacaac tacaagacca cgcctcccgt gctggactcc 180
gacggctcct tcttcctcta cagcaagctc accgtggaca agagcaggtg gcagcagggg 240
aacgtcttct catgctccgt gatgcatgag gctctgcaca accactacac gcagaagagc 300
ctctccctgt ctccgggtaa a 321

<210> SEQ ID NO 56
<211> LENGTH: 107
<212> TYPE: PRT
<213> ORGANISM: Artificial Sequence
<220> FEATURE:
<223> OTHER INFORMATION: Synthesized

<400> SEQUENCE: 56

Gly Gln Pro Arg Glu Pro Gln Val Tyr Thr Leu Pro Pro Ser Arg Asp
1 5 10 15

Glu Leu Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Lys Leu Thr Val Asp Lys Ser Arg Trp Gln Gln Gly
65 70 75 80

-continued

```
Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 57
<211> LENGTH: 1344
<212> TYPE: DNA
<213> ORGANISM: Artificial Sequence
<220> FEATURE:
<223> OTHER INFORMATION: Synthesized

<400> SEQUENCE: 57

gaagtccagc ttgtagaatc aggggggggc cttgttcaac ccggcagatc actcaggctt      60

tcttgtgccg cctctgggtt caccttcgat gactacgcta tgcactgggt cagacaagcg     120

ccgggcaagg gccttgagtg ggtttctgct atcacatgga attctggaca catcgactac     180

gccgattccg ttgagggtag gtttactatt agtcgggata acgcgaagaa cagcctctac     240

cttcaaatga attcattgag ggcggaggac actgcggttt actattgcgc aaaagtaagt     300

tacttgagca ccgcatcttc actggattac tggggccagg gaacattggt gacagtatcc     360

tcagcctcca ccaagggccc atcggtcttc cccctggcac cctcctccaa gagcacctct     420

gggggcacag cggccctggg ctgcctggtc aaggactact tccccgaacc ggtgacggtg     480

tcgtggaact caggcgccct gaccagcggc gtgcacacct tcccggctgt cctacagtcc     540

tcaggactct actccctcag cagcgtggtg accgtgccct ccagcagctt gggcacccag     600

acctacatct gcaacgtgaa tcacaagccc agcaacacca aggtggacaa gaaagttgag     660

cccaaatctt gtgacaaaac tcacacatgc ccaccgtgcc cagcacctga actcctgggg     720

ggaccgtcag tcttcctctt ccccccaaaa cccaaggaca ccctcatgat ctcccggacc     780

cctgaggtca catgcgtggt ggtggacgtg agccacgaag accctgaggt caagttcaac     840

tggtacgtgg acggcgtgga ggtgcataat gccaagacaa agccgcggga ggagcagtac     900

aacagcacgt accgggtggt cagcgtcctc accgtcctgc accaggactg gctgaatggc     960

aaggagtaca agtgcaaggt ctccaacaaa gccctcccag cccccatcga gaaaaccatc    1020

tccaaagcca aagggcagcc ccgagaacca gagacgctgc agcgcacgga cgcccccaaa    1080

acgcatatga ctcaccacgc tgtctctgac catgaagcca ccctgaggtg ctgggccctg    1140

agcttctacc ctgcggagat cacactgacc tggcagcggg atggggagga ccagacccag    1200

gacacggagc tcgtggagac caggcctgca ggggatggaa ccttccagaa gtgggtggct    1260

gtggtggtgc cttctggaca ggagcagaga tacacctgcc atgtgcagca tgagggtttg    1320

cccaagcccc tcaccctgag atgg                                           1344


<210> SEQ ID NO 58
<211> LENGTH: 448
<212> TYPE: PRT
<213> ORGANISM: Artificial Sequence
<220> FEATURE:
<223> OTHER INFORMATION: Synthesized

<400> SEQUENCE: 58

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
```

-continued

```
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Glu Thr
            340                 345                 350

Leu Gln Arg Thr Asp Ala Pro Lys Thr His Met Thr His His Ala Val
        355                 360                 365

Ser Asp His Glu Ala Thr Leu Arg Cys Trp Ala Leu Ser Phe Tyr Pro
    370                 375                 380

Ala Glu Ile Thr Leu Thr Trp Gln Arg Asp Gly Glu Asp Gln Thr Gln
385                 390                 395                 400

Asp Thr Glu Leu Val Glu Thr Arg Pro Ala Gly Asp Gly Thr Phe Gln
                405                 410                 415

Lys Trp Val Ala Val Val Val Pro Ser Gly Gln Glu Gln Arg Tyr Thr
            420                 425                 430

Cys His Val Gln His Glu Gly Leu Pro Lys Pro Leu Thr Leu Arg Trp
        435                 440                 445
```

<210> SEQ ID NO 59

<211> LENGTH: 1347
<212> TYPE: DNA
<213> ORGANISM: Artificial Sequence
<220> FEATURE:
<223> OTHER INFORMATION: Synthesized

<400> SEQUENCE: 59

```
gaagtccagc ttgtagaatc aggggggggc cttgttcaac ccggcagatc actcaggctt     60

tcttgtgccg cctctgggtt caccttcgat gactacgcta tgcactgggt cagacaagcg    120

ccgggcaagg gccttgagtg ggtttctgct atcacatgga attctggaca catcgactac    180

gccgattccg ttgagggtag gtttactatt agtcgggata acgcgaagaa cagcctctac    240

cttcaaatga attcattgag ggcggaggac actgcggttt actattgcgc aaaagtaagt    300

tacttgagca ccgcatcttc actggattac tggggccagg gaacattggt gacagtatcc    360

tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca atccagcgta ctccaaagat tcaggtttac   1080

tcacgtcatc cagcagagaa tggaaagtca aatttcctga attgctatgt gtctgggttt   1140

catccatccg acattgaagt tgacttactg aagaatggag agagaattga aaaagtggag   1200

cattcagact tgtctttcag caaggactgg tctttctatc tcttgtacta cactgaattc   1260

acccccactg aaaaagatga gtatgcctgc cgtgtgaacc atgtgacttt gtcacagccc   1320

aagatagtta agtgggatcg agacatg                                       1347
```

<210> SEQ ID NO 60
<211> LENGTH: 449
<212> TYPE: PRT
<213> ORGANISM: Artificial Sequence
<220> FEATURE:
<223> OTHER INFORMATION: Synthesized

<400> SEQUENCE: 60

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80
```

-continued

```
Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Ile Gln
            340                 345                 350

Arg Thr Pro Lys Ile Gln Val Tyr Ser Arg His Pro Ala Glu Asn Gly
        355                 360                 365

Lys Ser Asn Phe Leu Asn Cys Tyr Val Ser Gly Phe His Pro Ser Asp
    370                 375                 380

Ile Glu Val Asp Leu Leu Lys Asn Gly Glu Arg Ile Glu Lys Val Glu
385                 390                 395                 400

His Ser Asp Leu Ser Phe Ser Lys Asp Trp Ser Phe Tyr Leu Leu Tyr
                405                 410                 415

Tyr Thr Glu Phe Thr Pro Thr Glu Lys Asp Glu Tyr Ala Cys Arg Val
            420                 425                 430

Asn His Val Thr Leu Ser Gln Pro Lys Ile Val Lys Trp Asp Arg Asp
        435                 440                 445

Met
```

<210> SEQ ID NO 61
<211> LENGTH: 1389
<212> TYPE: DNA
<213> ORGANISM: Artificial Sequence
<220> FEATURE:
<223> OTHER INFORMATION: Synthesized

<400> SEQUENCE: 61
gaagtccagc ttgtagaatc aggggggggc cttgttcaac ccggcagatc actcaggctt 60
tcttgtgccg cctctgggtt caccttcgat gactacgcta tgcactgggt cagacaagcg 120
ccgggcaagg gccttgagtg ggtttctgct atcacatgga attctggaca catcgactac 180
gccgattccg ttgagggtag gtttactatt agtcgggata acgcgaagaa cagcctctac 240
cttcaaatga attcattgag ggcggaggac actgcggttt actattgcgc aaaagtaagt 300
tacttgagca ccgcatcttc actggattac tggggccagg gaacattggt gacagtatcc 360
tcagcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtgcacacct tcccggctgt cctacagtcc 540
tcaggactct actccctcag cagcgtggtg accgtgccct ccagcagctt gggcacccag 600
acctacatct gcaacgtgaa tcacaagccc agcaacacca aggtggacaa gaaagttgag 660
cccaaatctt gtgacaaaac tcacacatgc ccaccgtgcc cagcacctga actcctgggg 720
ggaccgtcag tcttcctctt ccccccaaaa cccaaggaca ccctcatgat ctcccggacc 780
cctgaggtca catgcgtggt ggtggacgtg agccacgaag accctgaggt caagttcaac 840
tggtacgtgg acggcgtgga ggtgcataat gccaagacaa agccgcggga ggagcagtac 900
aacagcacgt accgggtggt cagcgtcctc accgtcctgc accaggactg gctgaatggc 960
aaggagtaca agtgcaaggt ctccaacaaa gccctcccag cccccatcga gaaaaccatc 1020
tccaaagcca aagggcagcc ccgagaacca actccgatca ccaatgtacc tccagaggta 1080
actgtgctca caaacagccc tgtggaactg agagagccca acgtcctcat ctgtttcata 1140
gacaagttca ccccaccagt ggtcaatgtc acgtggcttc gaaatggaaa acctgtcacc 1200
acaggagtgt cagagacagt cttcctgccc agggaagacc accttttccg caagttccac 1260
tatctcccct tcctgccctc aactgaggac gtttacgact gcagggtgga gcactggggc 1320
ttggatgagc ctcttctcaa gcactgggag tttgatgctc caagccctct cccagagact 1380
acagagaac 1389

<210> SEQ ID NO 62
<211> LENGTH: 463
<212> TYPE: PRT
<213> ORGANISM: Artificial Sequence
<220> FEATURE:
<223> OTHER INFORMATION: Synthesized

<400> SEQUENCE: 62

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Ala Ile Thr Trp Asn Ser Gly His Ile Asp Tyr Ala Asp Ser Val
50 55 60

Glu Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Lys Val Ser Tyr Leu Ser Thr Ala Ser Ser Leu Asp Tyr Trp Gly

```
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Thr Pro
            340                 345                 350

Ile Thr Asn Val Pro Pro Glu Val Thr Val Leu Thr Asn Ser Pro Val
        355                 360                 365

Glu Leu Arg Glu Pro Asn Val Leu Ile Cys Phe Ile Asp Lys Phe Thr
    370                 375                 380

Pro Pro Val Val Asn Val Thr Trp Leu Arg Asn Gly Lys Pro Val Thr
385                 390                 395                 400

Thr Gly Val Ser Glu Thr Val Phe Leu Pro Arg Glu Asp His Leu Phe
                405                 410                 415

Arg Lys Phe His Tyr Leu Pro Phe Leu Pro Ser Thr Glu Asp Val Tyr
            420                 425                 430

Asp Cys Arg Val Glu His Trp Gly Leu Asp Glu Pro Leu Leu Lys His
        435                 440                 445

Trp Glu Phe Asp Ala Pro Ser Pro Leu Pro Glu Thr Thr Glu Asn
    450                 455                 460
```

<210> SEQ ID NO 63
<211> LENGTH: 1374
<212> TYPE: DNA
<213> ORGANISM: Artificial Sequence
<220> FEATURE:
<223> OTHER INFORMATION: Synthesized

<400> SEQUENCE: 63
gaagtccagc ttgtagaatc aggggggggc cttgttcaac ccggcagatc actcaggctt      60

```
tcttgtgccg cctctgggtt caccttcgat gactacgcta tgcactgggt cagacaagcg    120

ccgggcaagg gccttgagtg ggtttctgct atcacatgga attctggaca catcgactac    180

gccgattccg ttgagggtag gtttactatt agtcgggata acgcgaagaa cagcctctac    240

cttcaaatga attcattgag ggcggaggac actgcggttt actattgcgc aaaagtaagt    300

tacttgagca ccgcatcttc actggattac tggggccagg gaacattggt gacagtatcc    360

tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca cgagtccaac ctaaggtgac tgtatatcct   1080

tcaaagaccc agcccctgca gcaccacaac ctcctggtct gctctgtgag tggtttctat   1140

ccaggcagca ttgaagtcag gtggttcctg aacggccagg aagagaaggc tgggatggtg   1200

tccacaggcc tgatccagaa tggagactgg accttccaga ccctggtgat gctggaaaca   1260

gttcctcgaa gtggagaggt ttacacctgc caagtggagc acccaagcgt gacaagccct   1320

ctcacagtgg aatggagagc acggtctgaa tctgcacaga gcaagatgct gagt         1374
```

```
<210> SEQ ID NO 64
<211> LENGTH: 458
<212> TYPE: PRT
<213> ORGANISM: Artificial Sequence
<220> FEATURE:
<223> OTHER INFORMATION: Synthesized

<400> SEQUENCE: 64

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Arg Val
            340                 345                 350

Gln Pro Lys Val Thr Val Tyr Pro Ser Lys Thr Gln Pro Leu Gln His
        355                 360                 365

His Asn Leu Leu Val Cys Ser Val Ser Gly Phe Tyr Pro Gly Ser Ile
    370                 375                 380

Glu Val Arg Trp Phe Leu Asn Gly Gln Glu Glu Lys Ala Gly Met Val
385                 390                 395                 400

Ser Thr Gly Leu Ile Gln Asn Gly Asp Trp Thr Phe Gln Thr Leu Val
                405                 410                 415

Met Leu Glu Thr Val Pro Arg Ser Gly Glu Val Tyr Thr Cys Gln Val
            420                 425                 430

Glu His Pro Ser Val Thr Ser Pro Leu Thr Val Glu Trp Arg Ala Arg
        435                 440                 445

Ser Glu Ser Ala Gln Ser Lys Met Leu Ser
    450                 455
```

<210> SEQ ID NO 65
<211> LENGTH: 1374
<212> TYPE: DNA
<213> ORGANISM: Artificial Sequence
<220> FEATURE:
<223> OTHER INFORMATION: Synthesized

<400> SEQUENCE: 65

```
gaagtccagc ttgtagaatc aggggggggc cttgttcaac ccggcagatc actcaggctt      60

tcttgtgccg cctctgggtt caccttcgat gactacgcta tgcactgggt cagacaagcg     120

ccgggcaagg gccttgagtg ggtttctgct atcacatgga attctggaca catcgactac     180
```

gccgattccg ttgagggtag gtttactatt agtcgggata acgcgaagaa cagcctctac 240
cttcaaatga attcattgag ggcggaggac actgcggttt actattgcgc aaaagtaagt 300
tacttgagca ccgcatcttc actggattac tggggccagg gaacattggt gacagtatcc 360
tcagcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtgcacacct tcccggctgt cctacagtcc 540
tcaggactct actccctcag cagcgtggtg accgtgccct ccagcagctt gggcacccag 600
acctacatct gcaacgtgaa tcacaagccc agcaacacca aggtggacaa gaaagttgag 660
cccaaatctt gtgacaaaac tcacacatgc ccaccgtgcc cagcacctga actcctgggg 720
ggaccgtcag tcttcctctt ccccccaaaa cccaaggaca ccctcatgat ctcccggacc 780
cctgaggtca catgcgtggt ggtggacgtg agccacgaag accctgaggt caagttcaac 840
tggtacgtgg acggcgtgga ggtgcataat gccaagacaa agccgcggga ggagcagtac 900
aacagcacgt accgggtggt cagcgtcctc accgtcctgc accaggactg gctgaatggc 960
aaggagtaca agtgcaaggt ctccaacaaa gccctcccag cccccatcga gaaaaccatc 1020
tccaaagcca aagggcagcc ccgagaacca aatatccaga accctgaccc tgccgtgtac 1080
cagctgagag actctaaatc cagtgacaag tctgtctgcc tattcaccga ttttgattct 1140
caaacaaatg tgtcacaaag taaggattct gatgtgtata tcacagacaa aactgtgcta 1200
gacatgaggt ctatggactt caagagcaac agtgctgtgg cctggagcaa caaatctgac 1260
tttgcatgtg caaacgcctt caacaacagc attattccag aagacacctt cttccccagc 1320
ccagaaagtt cctgtgatgt caagctggtc gagaaaagct ttgaaacaga tacg 1374

<210> SEQ ID NO 66
<211> LENGTH: 458
<212> TYPE: PRT
<213> ORGANISM: Artificial Sequence
<220> FEATURE:
<223> OTHER INFORMATION: Synthesized

<400> SEQUENCE: 66

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Ala Ile Thr Trp Asn Ser Gly His Ile Asp Tyr Ala Asp Ser Val
50 55 60

Glu Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Lys Val Ser Tyr Leu Ser Thr Ala Ser Ser Leu Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Asn Ile
            340                 345                 350

Gln Asn Pro Asp Pro Ala Val Tyr Gln Leu Arg Asp Ser Lys Ser Ser
        355                 360                 365

Asp Lys Ser Val Cys Leu Phe Thr Asp Phe Asp Ser Gln Thr Asn Val
    370                 375                 380

Ser Gln Ser Lys Asp Ser Asp Val Tyr Ile Thr Asp Lys Thr Val Leu
385                 390                 395                 400

Asp Met Arg Ser Met Asp Phe Lys Ser Asn Ser Ala Val Ala Trp Ser
                405                 410                 415

Asn Lys Ser Asp Phe Ala Cys Ala Asn Ala Phe Asn Asn Ser Ile Ile
            420                 425                 430

Pro Glu Asp Thr Phe Phe Pro Ser Pro Glu Ser Ser Cys Asp Val Lys
        435                 440                 445

Leu Val Glu Lys Ser Phe Glu Thr Asp Thr
    450                 455
```

<210> SEQ ID NO 67
<211> LENGTH: 1443
<212> TYPE: DNA
<213> ORGANISM: Artificial Sequence
<220> FEATURE:
<223> OTHER INFORMATION: Synthesized

<400> SEQUENCE: 67

```
gaagtccagc ttgtagaatc aggggggggc cttgttcaac ccggcagatc actcaggctt      60

tcttgtgccg cctctgggtt caccttcgat gactacgcta tgcactgggt cagacaagcg     120

ccgggcaagg gccttgagtg ggtttctgct atcacatgga attctggaca catcgactac     180

gccgattccg ttgagggtag gtttactatt agtcgggata acgcgaagaa cagcctctac     240

cttcaaatga attcattgag ggcggaggac actgcggttt actattgcgc aaaagtaagt     300

tacttgagca ccgcatcttc actggattac tggggccagg gaacattggt gacagtatcc     360
```

```
tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca ctcgaggacc tgaaaaacgt gttcccaccc   1080

gaggtcgctg tgtttgagcc atcagaagca gagatctccc acacccaaaa ggccacactg   1140

gtgtgcctgg ccacaggctt ctaccccgac cacgtggagc tgagctggtg ggtgaatggg   1200

aaggaggtgc acagtggggt cagcacagac ccgcagcccc tcaaggagca gcccgccctc   1260

aatgactcca gatactgcct gagcagccgc ctgagggtct cggccacctt ctggcagaac   1320

ccccgcaacc acttccgctg tcaagtccag ttctacgggc tctcggagaa tgacgagtgg   1380

acccaggata gggccaaacc tgtcacccag atcgtcagcg ccgaggcctg gggtagagca   1440

gac                                                                 1443
```

<210> SEQ ID NO 68
<211> LENGTH: 481
<212> TYPE: PRT
<213> ORGANISM: Artificial Sequence
<220> FEATURE:
<223> OTHER INFORMATION: Synthesized

<400> SEQUENCE: 68

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Leu Glu
            340                 345                 350

Asp Leu Lys Asn Val Phe Pro Pro Glu Val Ala Val Phe Glu Pro Ser
        355                 360                 365

Glu Ala Glu Ile Ser His Thr Gln Lys Ala Thr Leu Val Cys Leu Ala
    370                 375                 380

Thr Gly Phe Tyr Pro Asp His Val Glu Leu Ser Trp Trp Val Asn Gly
385                 390                 395                 400

Lys Glu Val His Ser Gly Val Ser Thr Asp Pro Gln Pro Leu Lys Glu
                405                 410                 415

Gln Pro Ala Leu Asn Asp Ser Arg Tyr Cys Leu Ser Ser Arg Leu Arg
            420                 425                 430

Val Ser Ala Thr Phe Trp Gln Asn Pro Arg Asn His Phe Arg Cys Gln
        435                 440                 445

Val Gln Phe Tyr Gly Leu Ser Glu Asn Asp Glu Trp Thr Gln Asp Arg
    450                 455                 460

Ala Lys Pro Val Thr Gln Ile Val Ser Ala Glu Ala Trp Gly Arg Ala
465                 470                 475                 480

Asp
```

<210> SEQ ID NO 69
<211> LENGTH: 1458
<212> TYPE: DNA
<213> ORGANISM: Artificial Sequence
<220> FEATURE:
<223> OTHER INFORMATION: Synthesized

<400> SEQUENCE: 69

```
gaagtccagc ttgtagaatc aggggggggc cttgttcaac ccggcagatc actcaggctt     60

tcttgtgccg cctctgggtt caccttcgat gactacgcta tgcactgggt cagacaagcg    120

ccgggcaagg gccttgagtg ggtttctgct atcacatgga attctggaca catcgactac    180

gccgattccg ttgagggtag gtttactatt agtcgggata acgcgaagaa cagcctctac    240
```

-continued

```
cttcaaatga attcattgag ggcggaggac actgcggttt actattgcgc aaaagtaagt    300

tacttgagca ccgcatcttc actggattac tggggccagg gaacattggt gacagtatcc    360

tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca acagataaac aacttgatgc agatgtttcc   1080

cccaagccca ctatttttct tccttcaatt gctgaaacaa agctccagaa ggctggaaca   1140

tacctttgtc ttcttgagaa atttttccct gatgttatta agatacattg ggaagaaaag   1200

aagagcaaca cgattctggg atcccaggag gggaacacca tgaagactaa tgacacatac   1260

atgaaattta gctggttaac ggtgccagaa aagtcactgg acaaagaaca cagatgtatc   1320

gtcagacatg agaataataa aaacggagtt gatcaagaaa ttatctttcc tccaataaag   1380

acagatgtca tcacaatgga tcccaaagac aattgttcaa aagatgcaaa tgatacacta   1440

ctgctgcagc tcacaaac                                                 1458
```

```
<210> SEQ ID NO 70
<211> LENGTH: 486
<212> TYPE: PRT
<213> ORGANISM: Artificial Sequence
<220> FEATURE:
<223> OTHER INFORMATION: Synthesized

<400> SEQUENCE: 70

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Thr Asp
            340                 345                 350

Lys Gln Leu Asp Ala Asp Val Ser Pro Lys Pro Thr Ile Phe Leu Pro
        355                 360                 365

Ser Ile Ala Glu Thr Lys Leu Gln Lys Ala Gly Thr Tyr Leu Cys Leu
    370                 375                 380

Leu Glu Lys Phe Phe Pro Asp Val Ile Lys Ile His Trp Glu Glu Lys
385                 390                 395                 400

Lys Ser Asn Thr Ile Leu Gly Ser Gln Glu Gly Asn Thr Met Lys Thr
                405                 410                 415

Asn Asp Thr Tyr Met Lys Phe Ser Trp Leu Thr Val Pro Glu Lys Ser
            420                 425                 430

Leu Asp Lys Glu His Arg Cys Ile Val Arg His Glu Asn Asn Lys Asn
        435                 440                 445

Gly Val Asp Gln Glu Ile Ile Phe Pro Pro Ile Lys Thr Asp Val Ile
    450                 455                 460

Thr Met Asp Pro Lys Asp Asn Cys Ser Lys Asp Ala Asn Asp Thr Leu
465                 470                 475                 480

Leu Leu Gln Leu Thr Asn
                485
```

<210> SEQ ID NO 71
<211> LENGTH: 1425
<212> TYPE: DNA
<213> ORGANISM: Artificial Sequence
<220> FEATURE:
<223> OTHER INFORMATION: Synthesized

<400> SEQUENCE: 71
gaagtccagc ttgtagaatc aggggggggc cttgttcaac ccggcagatc actcaggctt 60

```
tcttgtgccg cctctgggtt caccttcgat gactacgcta tgcactgggt cagacaagcg    120

ccgggcaagg gccttgagtg ggtttctgct atcacatgga attctggaca catcgactac    180

gccgattccg ttgagggtag gtttactatt agtcgggata acgcgaagaa cagcctctac    240

cttcaaatga attcattgag ggcggaggac actgcggttt actattgcgc aaaagtaagt    300

tacttgagca ccgcatcttc actggattac tggggccagg gaacattggt gacagtatcc    360

tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca agaagtcagc ctcataccaa accatccgtt   1080

tttgtcatga aaaatggaac aaatgtcgct tgtctggtga aggaattcta ccccaaggat   1140

ataagaataa atctcgtgtc atccaagaag ataacagagt ttgatcctgc tattgtcatc   1200

tctcccagtg ggaagtacaa tgctgtcaag cttggtaaat atgaagattc aaattcagtg   1260

acatgttcag ttcaacacga caataaaact gtgcactcca ctgactttga agtgaagaca   1320

gattctacag atcacgtaaa accaaaggaa actgaaaaca caaagcaacc ttcaaagagc   1380

tgccataaac ccaaagccat agttcatacc gagaaggtga acatg                   1425
```

<210> SEQ ID NO 72
<211> LENGTH: 475
<212> TYPE: PRT
<213> ORGANISM: Artificial Sequence
<220> FEATURE:
<223> OTHER INFORMATION: Synthesized

<400> SEQUENCE: 72

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Arg Ser
            340                 345                 350

Gln Pro His Thr Lys Pro Ser Val Phe Val Met Lys Asn Gly Thr Asn
        355                 360                 365

Val Ala Cys Leu Val Lys Glu Phe Tyr Pro Lys Asp Ile Arg Ile Asn
    370                 375                 380

Leu Val Ser Ser Lys Lys Ile Thr Glu Phe Asp Pro Ala Ile Val Ile
385                 390                 395                 400

Ser Pro Ser Gly Lys Tyr Asn Ala Val Lys Leu Gly Lys Tyr Glu Asp
                405                 410                 415

Ser Asn Ser Val Thr Cys Ser Val Gln His Asp Asn Lys Thr Val His
            420                 425                 430

Ser Thr Asp Phe Glu Val Lys Thr Asp Ser Thr Asp His Val Lys Pro
        435                 440                 445

Lys Glu Thr Glu Asn Thr Lys Gln Pro Ser Lys Ser Cys His Lys Pro
    450                 455                 460

Lys Ala Ile Val His Thr Glu Lys Val Asn Met
465                 470                 475
```

<210> SEQ ID NO 73
<211> LENGTH: 1362
<212> TYPE: DNA
<213> ORGANISM: Artificial Sequence
<220> FEATURE:
<223> OTHER INFORMATION: Synthesized

<400> SEQUENCE: 73
gaagtccagc ttgtagaatc aggggggggc cttgttcaac ccggcagatc actcaggctt 60

```
tcttgtgccg cctctgggtt caccttcgat gactacgcta tgcactgggt cagacaagcg    120

ccgggcaagg gccttgagtg ggtttctgct atcacatgga attctggaca catcgactac    180

gccgattccg ttgagggtag gtttactatt agtcgggata acgcgaagaa cagcctctac    240

cttcaaatga attcattgag ggcggaggac actgcggttt actattgcgc aaaagtaagt    300

tacttgagca ccgcatcttc actggattac tggggccagg gaacattggt gacagtatcc    360

tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca gatggtaatg aagaaatggg tggtattaca   1080

cagacaccat ataaagtctc catctctgga accacagtaa tattgacatg ccctcagtat   1140

cctggatctg aaatactatg gcaacacaat gataaaaaca taggcggtga tgaggatgat   1200

aaaaacatag gcagtgatga ggatcacctg tcactgaagg aattttcaga attggagcaa   1260

agtggttatt atgtctgcta ccccagagga agcaaaccag aagatgcgaa cttttatctc   1320

tacctgaggg caagagtgtg tgagaactgc atggagatgg at                     1362
```

<210> SEQ ID NO 74
<211> LENGTH: 454
<212> TYPE: PRT
<213> ORGANISM: Artificial Sequence
<220> FEATURE:
<223> OTHER INFORMATION: Synthesized

<400> SEQUENCE: 74

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

-continued

```
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Asp Gly
            340                 345                 350

Asn Glu Glu Met Gly Gly Ile Thr Gln Thr Pro Tyr Lys Val Ser Ile
        355                 360                 365

Ser Gly Thr Thr Val Ile Leu Thr Cys Pro Gln Tyr Pro Gly Ser Glu
    370                 375                 380

Ile Leu Trp Gln His Asn Asp Lys Asn Ile Gly Gly Asp Glu Asp Asp
385                 390                 395                 400

Lys Asn Ile Gly Ser Asp Glu Asp His Leu Ser Leu Lys Glu Phe Ser
                405                 410                 415

Glu Leu Glu Gln Ser Gly Tyr Tyr Val Cys Tyr Pro Arg Gly Ser Lys
            420                 425                 430

Pro Glu Asp Ala Asn Phe Tyr Leu Tyr Leu Arg Ala Arg Val Cys Glu
        435                 440                 445

Asn Cys Met Glu Met Asp
    450
```

<210> SEQ ID NO 75
<211> LENGTH: 1332
<212> TYPE: DNA
<213> ORGANISM: Artificial Sequence
<220> FEATURE:
<223> OTHER INFORMATION: Synthesized

<400> SEQUENCE: 75

```
gaagtccagc ttgtagaatc aggggggggc cttgttcaac ccggcagatc actcaggctt      60

tcttgtgccg cctctgggtt caccttcgat gactacgcta tgcactgggt cagacaagcg     120

ccgggcaagg gccttgagtg ggtttctgct atcacatgga attctggaca catcgactac     180

gccgattccg ttgagggtag gtttactatt agtcgggata acgcgaagaa cagcctctac     240
```

-continued

```
cttcaaatga attcattgag ggcggaggac actgcggttt actattgcgc aaaagtaagt    300

tacttgagca ccgcatcttc actggattac tggggccagg gaacattggt gacagtatcc    360

tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca cagtcaatca aggaaacca cttggttaag   1080

gtgtatgact atcaagaaga tggttcggta cttctgactt gtgatgcaga agccaaaaat   1140

atcacatggt ttaaagatgg gaagatgatc ggcttcctaa ctgaagataa aaaaaaatgg   1200

aatctgggaa gtaatgccaa ggaccctcga gggatgtatc agtgtaaagg atcacagaac   1260

aagtcaaaac cactccaagt gtattacaga atgtgtcaga actgcattga actaaatgca   1320

gccaccatat ct                                                       1332
```

```
<210> SEQ ID NO 76
<211> LENGTH: 444
<212> TYPE: PRT
<213> ORGANISM: Artificial Sequence
<220> FEATURE:
<223> OTHER INFORMATION: Synthesized

<400> SEQUENCE: 76

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

-continued

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Ser
340 345 350

Ile Lys Gly Asn His Leu Val Lys Val Tyr Asp Tyr Gln Glu Asp Gly
355 360 365

Ser Val Leu Leu Thr Cys Asp Ala Glu Ala Lys Asn Ile Thr Trp Phe
370 375 380

Lys Asp Gly Lys Met Ile Gly Phe Leu Thr Glu Asp Lys Lys Lys Trp
385 390 395 400

Asn Leu Gly Ser Asn Ala Lys Asp Pro Arg Gly Met Tyr Gln Cys Lys
405 410 415

Gly Ser Gln Asn Lys Ser Lys Pro Leu Gln Val Tyr Tyr Arg Met Cys
420 425 430

Gln Asn Cys Ile Glu Leu Asn Ala Ala Thr Ile Ser
435 440

<210> SEQ ID NO 77
<211> LENGTH: 1284
<212> TYPE: DNA
<213> ORGANISM: Artificial Sequence
<220> FEATURE:
<223> OTHER INFORMATION: Synthesized

<400> SEQUENCE: 77
gaagtccagc ttgtagaatc aggggggggc cttgttcaac ccggcagatc actcaggctt 60
tcttgtgccg cctctgggtt caccttcgat gactacgcta tgcactgggt cagacaagcg 120
ccgggcaagg gccttgagtg ggtttctgct atcacatgga attctggaca catcgactac 180
gccgattccg ttgagggtag gtttactatt agtcgggata acgcgaagaa cagcctctac 240
cttcaaatga attcattgag ggcggaggac actgcggttt actattgcgc aaaagtaagt 300
tacttgagca ccgcatcttc actggattac tggggccagg gaacattggt gacagtatcc 360
tcagcctcca ccaagggccc atcggtcttc cccctggcac cctcctccaa gagcacctct 420
gggggcacag cggccctggg ctgcctggtc aaggactact tccccgaacc ggtgacggtg 480

```
tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgggtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca aagataccta tagaggaact tgaggacaga   1080

gtgtttgtga attgcaatac cagcatcaca tgggtagagg gaacggtggg aacactgctc   1140

tcagacatta caagactgga cctgggaaaa cgcatcctgg acccacgagg aatatatagg   1200

tgtaatggga cagatatata caaggacaaa gaatctaccg tgcaagttca ttatcgaatg   1260

tgccagagct gtgtggagct ggat                                          1284
```

```
<210> SEQ ID NO 78
<211> LENGTH: 428
<212> TYPE: PRT
<213> ORGANISM: Artificial Sequence
<220> FEATURE:
<223> OTHER INFORMATION: Synthesized

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

```
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Lys Ile
            340                 345                 350

Pro Ile Glu Glu Leu Glu Asp Arg Val Phe Val Asn Cys Asn Thr Ser
        355                 360                 365

Ile Thr Trp Val Glu Gly Thr Val Gly Thr Leu Leu Ser Asp Ile Thr
    370                 375                 380

Arg Leu Asp Leu Gly Lys Arg Ile Leu Asp Pro Arg Gly Ile Tyr Arg
385                 390                 395                 400

Cys Asn Gly Thr Asp Ile Tyr Lys Asp Lys Glu Ser Thr Val Gln Val
                405                 410                 415

His Tyr Arg Met Cys Gln Ser Cys Val Glu Leu Asp
            420                 425


<210> SEQ ID NO 79
<211> LENGTH: 294
<212> TYPE: DNA
<213> ORGANISM: Artificial Sequence
<220> FEATURE:
<223> OTHER INFORMATION: Synthesized

<400> SEQUENCE: 79

gagacgctgc agcgcacgga cgcccccaaa acgcatatga ctcaccacgc tgtctctgac      60

catgaagcca ccctgaggtg ctgggccctg agcttctacc ctgcggagat cacactgacc     120

tggcagcggg atggggagga ccagacccag gacacggagc tcgtggagac caggcctgca     180

ggggatggaa ccttccagaa gtgggtggct gtggtggtgc cttctggaca ggagcagaga     240

tacacctgcc atgtgcagca tgagggtttg cccaagcccc tcaccctgag atgg           294


<210> SEQ ID NO 80
<211> LENGTH: 297
<212> TYPE: DNA
<213> ORGANISM: Artificial Sequence
<220> FEATURE:
<223> OTHER INFORMATION: Synthesized

<400> SEQUENCE: 80

atccagcgta ctccaaagat tcaggtttac tcacgtcatc cagcagagaa tggaaagtca      60

aatttcctga attgctatgt gtctgggttt catccatccg acattgaagt tgacttactg     120

aagaatggag agagaattga aaaagtggag cattcagact tgtctttcag caaggactgg     180

tctttctatc tcttgtacta cactgaattc acccccactg aaaaagatga gtatgcctgc     240
```

cgtgtgaacc atgtgacttt gtcacagccc aagatagtta agtgggatcg agacatg 297

<210> SEQ ID NO 81
<211> LENGTH: 339
<212> TYPE: DNA
<213> ORGANISM: Artificial Sequence
<220> FEATURE:
<223> OTHER INFORMATION: Synthesized

<400> SEQUENCE: 81
actccgatca ccaatgtacc tccagaggta actgtgctca caaacagccc tgtggaactg 60
agagagccca acgtcctcat ctgtttcata gacaagttca ccccaccagt ggtcaatgtc 120
acgtggcttc gaaatggaaa acctgtcacc acaggagtgt cagagacagt cttcctgccc 180
agggaagacc accttttccg caagttccac tatctcccct tcctgccctc aactgaggac 240
gtttacgact gcagggtgga gcactggggc ttggatgagc ctcttctcaa gcactgggag 300
tttgatgctc caagccctct cccagagact acagagaac 339

<210> SEQ ID NO 82
<211> LENGTH: 324
<212> TYPE: DNA
<213> ORGANISM: Artificial Sequence
<220> FEATURE:
<223> OTHER INFORMATION: Synthesized

<400> SEQUENCE: 82
cgagtccaac ctaaggtgac tgtatatcct tcaaagaccc agcccctgca gcaccacaac 60
ctcctggtct gctctgtgag tggtttctat ccaggcagca ttgaagtcag gtggttcctg 120
aacggccagg aagagaaggc tgggatggtg tccacaggcc tgatccagaa tggagactgg 180
accttccaga ccctggtgat gctggaaaca gttcctcgaa gtggagaggt ttacacctgc 240
caagtggagc acccaagcgt gacaagccct ctcacagtgg aatggagagc acggtctgaa 300
tctgcacaga gcaagatgct gagt 324

<210> SEQ ID NO 83
<211> LENGTH: 324
<212> TYPE: DNA
<213> ORGANISM: Artificial Sequence
<220> FEATURE:
<223> OTHER INFORMATION: Synthesized

<400> SEQUENCE: 83
aatatccaga accctgaccc tgccgtgtac cagctgagag actctaaatc cagtgacaag 60
tctgtctgcc tattcaccga ttttgattct caaacaaatg tgtcacaaag taaggattct 120
gatgtgtata tcacagacaa aactgtgcta gacatgaggt ctatggactt caagagcaac 180
agtgctgtgg cctggagcaa caaatctgac tttgcatgtg caaacgcctt caacaacagc 240
attattccag aagacacctt cttccccagc ccagaaagtt cctgtgatgt caagctggtc 300
gagaaaagct ttgaaacaga tacg 324

<210> SEQ ID NO 84
<211> LENGTH: 393
<212> TYPE: DNA
<213> ORGANISM: Artificial Sequence
<220> FEATURE:
<223> OTHER INFORMATION: Synthesized

<400> SEQUENCE: 84
ctcgaggacc tgaaaaacgt gttcccaccc gaggtcgctg tgtttgagcc atcagaagca 60

```
gagatctccc acacccaaaa ggccacactg gtgtgcctgg ccacaggctt ctaccccgac    120

cacgtggagc tgagctggtg ggtgaatggg aaggaggtgc acagtggggt cagcacagac    180

ccgcagcccc tcaaggagca gcccgccctc aatgactcca gatactgcct gagcagccgc    240

ctgagggtct cggccacctt ctggcagaac ccccgcaacc acttccgctg tcaagtccag    300

ttctacgggc tctcggagaa tgacgagtgg acccaggata gggccaaacc tgtcacccag    360

atcgtcagcg ccgaggcctg ggtagagca gac                                  393


<210> SEQ ID NO 85
<211> LENGTH: 408
<212> TYPE: DNA
<213> ORGANISM: Artificial Sequence
<220> FEATURE:
<223> OTHER INFORMATION: Synthesized

<400> SEQUENCE: 85

acagataaac aacttgatgc agatgtttcc cccaagccca ctatttttct tccttcaatt     60

gctgaaacaa agctccagaa ggctggaaca tacctttgtc ttcttgagaa atttttccct    120

gatgttatta agatacattg ggaagaaaag aagagcaaca cgattctggg atcccaggag    180

gggaacacca tgaagactaa tgacacatac atgaaattta gctggttaac ggtgccagaa    240

aagtcactgg acaaagaaca cagatgtatc gtcagacatg agaataataa aaacggagtt    300

gatcaagaaa ttatctttcc tccaataaag acagatgtca tcacaatgga tcccaaagac    360

aattgttcaa aagatgcaaa tgatacacta ctgctgcagc tcacaaac                 408


<210> SEQ ID NO 86
<211> LENGTH: 375
<212> TYPE: DNA
<213> ORGANISM: Artificial Sequence
<220> FEATURE:
<223> OTHER INFORMATION: Synthesized

<400> SEQUENCE: 86

agaagtcagc ctcataccaa accatccgtt tttgtcatga aaaatggaac aaatgtcgct     60

tgtctggtga aggaattcta ccccaaggat ataagaataa atctcgtgtc atccaagaag    120

ataacagagt ttgatcctgc tattgtcatc tctcccagtg ggaagtacaa tgctgtcaag    180

cttggtaaat atgaagattc aaattcagtg acatgttcag ttcaacacga caataaaact    240

gtgcactcca ctgactttga agtgaagaca gattctacag atcacgtaaa accaaaggaa    300

actgaaaaca caaagcaacc ttcaaagagc tgccataaac ccaaagccat agttcatacc    360

gagaaggtga acatg                                                      375


<210> SEQ ID NO 87
<211> LENGTH: 312
<212> TYPE: DNA
<213> ORGANISM: Artificial Sequence
<220> FEATURE:
<223> OTHER INFORMATION: Synthesized

<400> SEQUENCE: 87

gatggtaatg aagaaatggg tggtattaca cagacaccat ataaagtctc catctctgga     60

accacagtaa tattgacatg ccctcagtat cctggatctg aaatactatg gcaacacaat    120

gataaaaaca taggcggtga tgaggatgat aaaaacatag gcagtgatga ggatcacctg    180

tcactgaagg aattttcaga attggagcaa agtggttatt atgtctgcta ccccagagga    240
```

agcaaaccag aagatgcgaa cttttatctc tacctgaggg caagagtgtg tgagaactgc 300
atggagatgg at 312

<210> SEQ ID NO 88
<211> LENGTH: 282
<212> TYPE: DNA
<213> ORGANISM: Artificial Sequence
<220> FEATURE:
<223> OTHER INFORMATION: Synthesized

<400> SEQUENCE: 88
cagtcaatca aaggaaacca cttggttaag gtgtatgact atcaagaaga tggttcggta 60
cttctgactt gtgatgcaga agccaaaaat atcacatggt ttaaagatgg gaagatgatc 120
ggcttcctaa ctgaagataa aaaaaaatgg aatctgggaa gtaatgccaa ggaccctcga 180
gggatgtatc agtgtaaagg atcacagaac aagtcaaaac cactccaagt gtattacaga 240
atgtgtcaga actgcattga actaaatgca gccaccatat ct 282

<210> SEQ ID NO 89
<211> LENGTH: 234
<212> TYPE: DNA
<213> ORGANISM: Artificial Sequence
<220> FEATURE:
<223> OTHER INFORMATION: Synthesized

<400> SEQUENCE: 89
aagataccta tagaggaact tgaggacaga gtgtttgtga attgcaatac cagcatcaca 60
tgggtagagg gaacggtggg aacactgctc tcagacatta caagactgga cctgggaaaa 120
cgcatcctgg acccacgagg aatatatagg tgtaatggga cagatatata caaggacaaa 180
gaatctaccg tgcaagttca ttatcgaatg tgccagagct gtgtggagct ggat 234

<210> SEQ ID NO 90
<211> LENGTH: 49
<212> TYPE: DNA
<213> ORGANISM: Artificial sequence
<220> FEATURE:
<223> OTHER INFORMATION: Synthesized

<400> SEQUENCE: 90
tagactcgag cggccgcacc atggacatga gggtccccgc tcagctcct 49

<210> SEQ ID NO 91
<211> LENGTH: 46
<212> TYPE: DNA
<213> ORGANISM: Artificial sequence
<220> FEATURE:
<223> OTHER INFORMATION: Synthesized

<400> SEQUENCE: 91
tggtggaatt ctcattacta gcactcgccg cggttgaagg acttgg 46

<210> SEQ ID NO 92
<211> LENGTH: 48
<212> TYPE: DNA
<213> ORGANISM: Artificial sequence
<220> FEATURE:
<223> OTHER INFORMATION: Synthesized

<400> SEQUENCE: 92
tagactcgag cggccgcacc atggagttgg gactgagctg gattttcc 48

-continued

<210> SEQ ID NO 93
<211> LENGTH: 48
<212> TYPE: DNA
<213> ORGANISM: Artificial sequence
<220> FEATURE:
<223> OTHER INFORMATION: Synthesized

<400> SEQUENCE: 93
acttaagctt ggtacctcat ttacccggag acagggagag gctcttct 48

<210> SEQ ID NO 94
<211> LENGTH: 24
<212> TYPE: DNA
<213> ORGANISM: Artificial sequence
<220> FEATURE:
<223> OTHER INFORMATION: Synthesized

<400> SEQUENCE: 94
tggttctcgg ggctgccctt tggc 24

<210> SEQ ID NO 95
<211> LENGTH: 30
<212> TYPE: DNA
<213> ORGANISM: Artificial sequence
<220> FEATURE:
<223> OTHER INFORMATION: Synthesized

<400> SEQUENCE: 95
atcgagaaaa ccatctccaa agccaaaggg 30

<210> SEQ ID NO 96
<211> LENGTH: 42
<212> TYPE: DNA
<213> ORGANISM: Artificial sequence
<220> FEATURE:
<223> OTHER INFORMATION: Synthesized

<400> SEQUENCE: 96
acttaagctt ggtacctcac catctcaggg tgaggggctt gg 42

<210> SEQ ID NO 97
<211> LENGTH: 47
<212> TYPE: DNA
<213> ORGANISM: Artificial sequence
<220> FEATURE:
<223> OTHER INFORMATION: Synthesized

<400> SEQUENCE: 97
acttaagctt ggtaccttac atgtctcgat cccacttaac tatcttg 47

<210> SEQ ID NO 98
<211> LENGTH: 50
<212> TYPE: DNA
<213> ORGANISM: Artificial sequence
<220> FEATURE:
<223> OTHER INFORMATION: Synthesized

<400> SEQUENCE: 98
acttaagctt ggtaccttag ttctctgtag tctctgggag agggcttgga 50

<210> SEQ ID NO 99
<211> LENGTH: 50
<212> TYPE: DNA
<213> ORGANISM: Artificial sequence
<220> FEATURE:
<223> OTHER INFORMATION: Synthesized

<400> SEQUENCE: 99
acttaagctt ggtacctcaa ctcagcatct tgctctgtgc agattcagac 50

<210> SEQ ID NO 100
<211> LENGTH: 47
<212> TYPE: DNA
<213> ORGANISM: Artificial sequence
<220> FEATURE:
<223> OTHER INFORMATION: Synthesized

<400> SEQUENCE: 100
acttaagctt ggtacctcac gtatctgttt caaagctttt ctcgacc 47

<210> SEQ ID NO 101
<211> LENGTH: 52
<212> TYPE: DNA
<213> ORGANISM: Artificial sequence
<220> FEATURE:
<223> OTHER INFORMATION: Synthesized

<400> SEQUENCE: 101
acttaagctt ggtaccctag tctgctctac cccaggcctc ggcgctgacg at 52

<210> SEQ ID NO 102
<211> LENGTH: 51
<212> TYPE: DNA
<213> ORGANISM: Artificial sequence
<220> FEATURE:
<223> OTHER INFORMATION: Synthesized

<400> SEQUENCE: 102
acttaagctt ggtaccttag tttgtgagct gcagcagtag tgtatcattt g 51

<210> SEQ ID NO 103
<211> LENGTH: 53
<212> TYPE: DNA
<213> ORGANISM: Artificial sequence
<220> FEATURE:
<223> OTHER INFORMATION: Synthesized

<400> SEQUENCE: 103
acttaagctt ggtaccttac atgttcacct tctcggtatg aactatggct ttg 53

<210> SEQ ID NO 104
<211> LENGTH: 46
<212> TYPE: DNA
<213> ORGANISM: Artificial sequence
<220> FEATURE:
<223> OTHER INFORMATION: Synthesized

<400> SEQUENCE: 104
acttaagctt ggtacctcaa tccatctcca tgcagttctc acacac 46

<210> SEQ ID NO 105
<211> LENGTH: 56
<212> TYPE: DNA
<213> ORGANISM: Artificial sequence
<220> FEATURE:
<223> OTHER INFORMATION: Synthesized

<400> SEQUENCE: 105
acttaagctt ggtacctcaa gatatggtgg ctgcatttag ttcaatgcag ttctga 56

<210> SEQ ID NO 106
<211> LENGTH: 47

-continued

```
<212> TYPE: DNA
<213> ORGANISM: Artificial sequence
<220> FEATURE:
<223> OTHER INFORMATION: Synthesized

<400> SEQUENCE: 106

acttaagctt ggtacctcaa tccagctcca cacagctctg gcacatt                47
```

HETERODIMERIC BISPECIFIC ANTIBODIES

CROSS-REFERENCE TO RELATED APPLICATION

The present application is a US national stage entry of PCT/US2018/038833 filed Jun. 21, 2018, which claims the benefit of U.S. 62/523,220 filed Jun. 21, 2017, which is incorporated by reference in its entirety for all purposes.

REFERENCE TO A SEQUENCE LISTING

The present application includes a txt sequence listing named 541262SEQLST.TXT of 174,922 bytes created Dec. 14, 2022, which is incorporated by reference.

BACKGROUND

Monoclonal antibodies as chimeric, humanized or fully human molecules have proven value as efficacious drugs for treatment of a range of medical conditions & diseases.

Antibody molecules in their native context are comprised of two heavy-chain homodimers, each of which forms a heterodimer in partnership with two identical light chain molecules (FIG. 1A). Conventional monoclonal antibodies, either as whole molecules comprised of bivalent (two-armed) heavy and light chain heterodimers with the Fc fragment as a contiguous element of the heavy chain, or as Fab fragments, bind or recognize one antigen per molecule (FIG. 1A).

Many diseases are comprised of multiple co-morbidities arising from multiple pathologies. Bispecific antibodies offer the ability to bind, and thereby neutralize two or more antigens per antibody molecule (FIG. 1B). The potential to significantly enhance the therapeutic properties (and value) of monoclonal antibody drugs have made bispecific antibodies an active area of investigation and invention. Accordingly, multiple solutions toward naturally produced, or engineered versions of bi-specific antibodies have been described in the scientific literature over the past decade, as reviewed in (Spiess et al. 2015).

The assembly of antibody heavy chains into homodimers is driven by the CH3 domain(Gunasekaran et al. 2010). Product purity of bi-specific antibodies is dependent on two factors, heterodimeric assembly of two different heavy-chains co-expressed in the cell, and appropriate pairing of two different light chains with the respective heavy chains (FIG. 2). Despite the progress in technologies for expressing bi-specific antibodies, there is a need in the art for improved product purity, as well as a scale-able manufacturing solution.

SUMMARY OF THE CLAIMED INVENTION

The invention provides a heterodimeric bispecific antibody (HBA) comprising a first antigen recognizing moiety (A) and a second antigen recognizing moiety (B). A contains a first light chain comprising a first light chain variable region (VL1) fused to a light chain constant region (CL), and a first heavy chain comprising a first heavy chain variable region (VH1) fused to a first heavy chain constant domain (CH1) optionally fused, through a hinge region (H), to a first heavy chain pairing partner (X). VL1 & VH1 can be either humanized, fully human, or non-human. B contains a second light chain comprising a second light chain variable region (VL2) fused to a first light chain pairing partner (m), which VL2 is different from VL1, and a second heavy chain comprising a second heavy chain variable region (VH2) fused to a second light chain pairing partner (n) fused, optionally through a hinge region (H), to a second heavy chain pairing partner (Y). VL2 and VH2 can be either humanized, fully human, or non-human. X and Y are members of a first binding pair of components from the immunoglobulin superfamily (X and Y binding pair). m and n are members of a second binding pair of components from the immunoglobulin superfamily that is different from the first binding pair (m and n binding pair). Optionally CH1 and X are fused through a constant heavy chain region (CH2) and n and Y are fused through the CH2.

In some HBA's, the CH1 is fused through H to X and n is fused through H to Y. In some HBA's the X and Y binding pair and the m and n binding pair are derived from MHC class I molecules (MHC I), MHC class II molecules (MHC II) or T-cell receptor complex of molecules (TCR). For example, the X and Y binding pair and the m and n binding pair can be any of (i) MHC II α2 domain and MHC II β2 domain, (ii) MHC I α3 domain and beta-2 microglobulin (β2M), (iii) TCR CD3 ε chain and TCR CD3 γ chain, (iv) TCR CD3 ε chain and TCR CD3 δ chain, (v) TCR antigen receptor (AgR) Cα domain and TCR AgR Cβ domain, or (vi) TCR AgR Cγ domain and TCR AgR Cδ domain. In any given pair, the actual heterologous polypeptides in the positions of X and Y or m and n can be reversed. However, X and Y are each different from both m and n.

Some HBA's of the invention comprise a first antigen recognizing moiety (C) and a second antigen recognizing moiety (D). C contains a first light chain variable region (VL1) fused to a first heavy chain variable region (VH1) fused, optionally through a hinge region (H), to a first heavy chain pairing partner (X). D comprises a second light chain variable region (VL2) fused to a second heavy chain variable region (VH2) fused, optionally through a hinge region (H), to a second heavy chain pairing partner (Y). X and Y are members of a first binding pair of components derived from the immunoglobulin superfamily (X and Y binding pair). Optionally, VH1 and X are fused through a constant heavy chain region (CH2) and VH2 and Y are fused through the CH2. In some such HBA's, the CH1 is fused through H to X and n is fused through H to Y. In some HBA's the X and Y binding pair and the m and n binding pair are derived from MHC class I molecules (MHC I), MHC II or TCR.

Any of the HBA's can include a CH2, such that VH1 and X are fused through a constant heavy chain region (CH2) and VH2 and Y are fused through CH2. In addition, or alternatively, X is fused to a third heavy chain binding partner (p) and Y is fused to a fourth heavy chain binding partner (q). If present, p and q are members of a third binding pair of components derived from the immunoglobulin superfamily (p and q binding pair). In some HBA's the p and q binding pair is derived from MHC I, MHC II or TCR. p and q can be the same as X and Y, respectively, or the p and q binding pair can be different from the X and Y binding pair. However, if a p and q binding pair and an m and n binding pair are both present, then p and q are each different from both m and n.

For example, if the X and Y binding pair is MHC I α3 domain and beta-2 microglobulin (β2M), (a) the m and n binding pair, if present, can be MHC II α2 domain and MHC II β2 domain, TCR CD3 ε chain and TCR CD3 γ chain, TCR CD3 ε chain and TCR CD3 δ chain, TCR AgR Cα domain and TCR AgR Cβ domain or TCR AgR Cγ domain and TCR AgR Cδ domain; and (b) the p and q binding pair can be MHC II α2 domain and MHC II β2 domain, TCR CD3 ε chain and TCR CD3 γ chain, TCR CD3 ε chain and TCR CD3 δ chain, TCR AgR Cα domain and TCR AgR Cβ domain or TCR AgR Cγ domain and TCR AgR Cδ domain, but only if different from the pair in (a).

In some of the HBA's, CL is human Cκ or Cλ. Some heavy chain segments, such as, for example, CH1, H and CH2 are from human IgA, IgD, IgM, IgE, or IgG isotypes 1, 2, 3 or 4, and can be, for example, from IgG1.

The HBA's can include at least one of A, B, C or D derived from a therapeutic antibody, such as any of the therapeutic antibodies disclosed herein, for example, A or B, but not both, can be derived from adalimumab. Some HBA's contain VH1, CH1, VL1, CL from adalimumab, X is MHC I α3 domain and Y is beta-2 microglobulin (β2M). As discussed above, the specific heterologous polypeptides in positions X and Y can be reversed. As provided in further detail infra, various substitutions of adalimumab CH3 with pairing partners from the immunoglobulin superfamily (IgSF) can readily be made with the teachings herein.

Also provided herein are polynucleotides comprising one or more nucleic acid(s) encoding the first heavy chain, the second light chain or the second heavy chain discussed supra. Also provided are polynucleotides comprising one or more nucleic acid(s) encoding moiety C or moiety D discussed supra. Vectors comprising one or more of these polynucleotides are provided, as well as host cells containing such polynucleotides or vectors. The invention also provides methods of making HBA's comprising culturing such host cells under conditions so as to express the nucleic acid(s) encoding the HBA, and recovering the HBA.

The invention further provides a heterodimeric bispecific fusion protein (HBFP) comprising a first (R1) comprising a first biologically active moiety (R1) and a second moiety (R2) comprising a second biologically active moiety (R2), which are fused to heterologous polypeptides in positions X and Y as discussed supra.

The invention further provides a method for treating a patient having or at risk for having cancer, an autoimmune or inflammatory condition, a neurodegenerative disease, an infectious disease, osteoporosis, dyslipidemia, macular degeneration, a blood coagulation disorder, a cardiovascular disease or disorder, an organ transplant, diabetes, influenza, a muscle wasting disorder or a gastrointestinal disease or disorder, comprising administering to the patient a therapeutically effective dose of any of the HBA's or HBFP's described herein.

Some patients have cancer, for example, ovarian cancer, prostate cancer, breast cancer, colorectal cancer, non-small cell lung carcinoma, gastrointestinal cancer, hematological cancer, metastatic cancer, squamous cell carcinoma, head and neck cancer, solid tumors, glioblastoma, neuroblastoma, testicular cancer, adrenocortical carcinoma, melanoma, non-Hodgkin's lymphoma or pancreatic cancer. Some patients have a hematological cancer such as lymphoma, non-Hodgkin's lymphoma, acute myelogenous leukemia, chronic lymphocytic leukemia, multiple myeloma, or Hodgkin's lymphoma.

Some patients have an autoimmune or inflammatory condition, such as inflammatory bowel disease, ulcerative colitis, Crohn's disease, rheumatoid arthritis, plaque psoriasis, psoriatic arthritis, ankylosing spondylitis, juvenile idiopathic arthritis, multiple sclerosis, systematic lupus erythematosus or uveitis.

Some patients have a neurodegenerative disease, such as Alzheimer's disease, Parkinson's disease or ALS.

BRIEF DESCRIPTION OF THE DRAWINGS

FIG. 1A depicts a conventional antibody. FIG. 1B depicts a bi-specific antibody. Inter-chain di-sulfide linkages are represented by thin lines, V & C denote variable and constant regions, respectively. L and H denote light and heavy chains, respectively. Functional activity of heavy chain constant regions is indicated in boxes. Bound antigens A, B & C are depicted as circles, hexagon or star shaped objects, respectively.

FIGS. 6A-B depict the adalimumab light chain DNA sequence and predicted protein sequence. FIG. 6A depicts the adalimumab light chain DNA sequence (SEQ ID NO:1) and FIG. 6B depicts the predicted protein sequence of adalimumab light chain (SEQ ID NO:2). The leader peptide and Cκ are shown in lowercase, with the variable region in uppercase. The CDRs are shaded grey and underlined.

FIGS. 7A-B depict the adalimumab heavy chain DNA sequence and predicted protein sequence. FIG. 7A depicts the adalimumab heavy chain DNA sequence (SEQ ID NO:3) and FIG. 7B depicts the predicted protein sequence of adalimumab heavy chain (SEQ ID NO:4). The leader peptide and constant regions are shown in lowercase, and VH is shown in uppercase. The CDR's are shaded grey and underlined. CH1 is shown in lowercase italics, the hinge region with a dotted underline, the CH2 domain in lowercase bold face, and the CH3 domain in lowercase double underline.

FIGS. 8A-B depict the DNA sequence and predicted protein sequence for an exemplary hybrid adalimumab heavy chain with MHC-1 HLA-A (A*68 allele) α3 domain replacing CH3 domain. FIG. 8A depicts the DNA sequence encoding the hybrid molecule (SEQ ID NO:5). FIG. 8B depicts the predicted protein sequence of the hybrid molecule (SEQ ID NO:6). FIG. 8C depicts the DNA sequence encoding an MHC-1 HLA-A (A*68 allele) α3 domain (SEQ ID NO:7). FIG. 8D depicts the protein sequence of an MHC-1 HLA-A (A*68 allele) α3 domain (SEQ ID NO:8). The leader peptide and constant regions are shown in lowercase, and VH in uppercase. The CDR's are shaded grey and underlined. CH1 is shown in lowercase italics, the hinge region with dotted underline, the CH2 domain in lowercase bold face, the flexible loop region separating CH2 domain from CH3 domain in lowercase double underline, the flexible loop region n-terminal to MHC-1 α3 domain as uppercase italic+wavy underline, and the α3 domain from MHC-1 in uppercase boldface.

FIGS. 9A-D depict the DNA sequence and predicted protein sequence for an exemplary hybrid adalimumab heavy chain with β2 microglobulin replacing CH3 domain. FIG. 9A depicts the DNA sequence encoding the hybrid molecule (SEQ ID NO:9). FIG. 9B depicts the predicted protein sequence of the hybrid molecule (SEQ ID NO:10). FIG. 9C depicts the DNA sequence encoding a β2 microglobulin (SEQ ID NO:11). FIG. 9D depicts the predicted protein sequence of a β2 microglobulin (SEQ ID NO:12). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, and the β2 microglobulin sequence in uppercase bold face.

FIGS. 10A-D depict the DNA sequence and predicted protein sequence for an exemplary hybrid adalimumab heavy chain with MHC II α2 domain (derived from HLA-DR alpha) replacing CH3 domain. FIG. 10A depicts the DNA sequence encoding the hybrid molecule (SEQ ID NO:13). FIG. 10B depicts the predicted protein sequence of the hybrid molecule (SEQ ID NO:14). FIG. 10C depicts the DNA sequence encoding an MHC II α2 domain from HLA-DR alpha (SEQ ID NO:15). FIG. 10D depicts the predicted protein sequence of an MHC II α2 domain from HLA-DR alpha (SEQ ID NO:16). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the flexible loop separating MHC II α1 and α2 domain in uppercase italic and wavy underline, the MHC II α2 domain in uppercase bold, the juxta-membrane connecting peptide between the MHC II α2 domain and the trans-membrane domain in uppercase dotted underline.

FIGS. 11A-D depict the DNA sequence and predicted protein sequence for an exemplary hybrid adalimumab heavy chain with MHC II β2 domain (derived from HLA-DR beta1) replacing CH3 domain. FIG. 11A depicts the DNA sequence encoding the hybrid molecule (SEQ ID NO:17). FIG. 11B depicts the predicted protein sequence of the hybrid molecule (SEQ ID NO:18). FIG. 11C depicts the DNA sequence encoding an MHC II β2 domain from HLA-DR beta1 (SEQ ID NO:19). FIG. 11D depicts the predicted protein sequence of an MHC II β2 domain from HLA-DR beta1 (SEQ ID NO:20). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the flexible loop separating MHC II β1 and β2 domain in uppercase italic and wavy underline, the MHC II β2 domain in uppercase bold, the juxta-membrane connecting peptide between the MHC II β2 domain and the trans-membrane domain in uppercase dotted underline.

FIGS. 12A-D depict the DNA sequence and predicted protein sequence for an exemplary hybrid adalimumab heavy chain with T-cell antigen receptor (TCR) Ca domain replacing CH3 domain. FIG. 12A depicts the DNA sequence encoding the hybrid molecule (SEQ ID NO:21). FIG. 12B depicts the predicted protein sequence of the hybrid molecule (SEQ ID NO:22). FIG. 12C depicts the DNA sequence encoding a TCR Cα domain (SEQ ID NO:23). FIG. 12D depicts the predicted protein sequence of a TCR Cα domain (SEQ ID NO:24). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the flexible loop separating TCR Vα and Cα domain in uppercase italic and wavy underline, the TCR Cα domain in uppercase bold, the juxta-membrane connecting peptide between the TCR Cα domain and the trans-membrane domain in uppercase dotted underline.

FIGS. 13A-D depicts the DNA sequence and predicted protein sequence for an exemplary hybrid adalimumab heavy chain with T-cell antigen receptor (TCR) Cβ domain replacing CH3 domain. FIG. 13A depicts the DNA sequence encoding the hybrid molecule (SEQ ID NO:25). FIG. 13B depicts the predicted protein sequence of the hybrid molecule (SEQ ID NO:26). FIG. 13C depicts the DNA sequence encoding a TCR Cβ domain (SEQ ID NO:27). FIG. 13D depicts the predicted protein sequence of a TCR Cβ domain (SEQ ID NO:28). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the flexible loop separating TCR Vβ and Cβ domain in uppercase italic and wavy underline, the TCR Cβ domain in uppercase bold, the juxta-membrane connecting peptide between the TCR Cβ domain and the trans-membrane domain in uppercase dotted underline.

FIGS. 14A-D depicts the DNA sequence and predicted protein sequence for an exemplary hybrid adalimumab heavy chain with T-cell antigen receptor (TCR) Cy domain replacing CH3 domain. FIG. 14A depicts the DNA sequence encoding the hybrid molecule (SEQ ID NO:29). FIG. 14B depicts the predicted protein sequence of the hybrid molecule (SEQ ID NO:30). FIG. 14C depicts the DNA sequence encoding a TCR Cγ domain (SEQ ID NO:31). FIG. 14D depicts the predicted protein sequence of a TCR Cγ domain (SEQ ID NO:32). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the flexible loop separating TCR Vγ and Cγ domain in uppercase italic and wavy underline, the TCR Cγ domain in uppercase bold, the juxta-membrane connecting peptide between the TCR Cγ domain and the trans-membrane domain in uppercase dotted underline.

FIGS. 15A-D depicts the DNA sequence and predicted protein sequence for an exemplary hybrid adalimumab heavy chain with T-cell antigen receptor (TCR) Cδ domain replacing CH3 domain. FIG. 15A depicts the DNA sequence encoding the hybrid molecule (SEQ ID NO:33). FIG. 15B depicts the predicted protein sequence of the hybrid molecule (SEQ ID NO:34). FIG. 15C depicts the DNA sequence encoding a TCR Cδ domain (SEQ ID NO:35). FIG. 15D depicts the predicted protein sequence of a TCR Cδ domain (SEQ ID NO:36). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the flexible loop separating TCR Vδ and Cδ domain in uppercase italic and wavy underline, the TCR Cδ domain in uppercase bold, the juxta-membrane connecting peptide between the TCR Cδ domain and the trans-membrane domain in uppercase dotted underline.

FIGS. 16A-D depicts the DNA sequence and predicted protein sequence for an exemplary hybrid adalimumab heavy chain with CD3 ε-chain ecto-domain replacing CH3 domain. FIG. 16A depicts the DNA sequence encoding the hybrid molecule (SEQ ID NO:37). FIG. 16B depicts the predicted protein sequence of the hybrid molecule (SEQ ID NO:38). FIG. 16C depicts the DNA sequence encoding a CD3 ε-chain ecto-domain (SEQ ID NO:39). FIG. 16D depicts the predicted protein sequence of a CD3 ε-chain ecto-domain (SEQ ID NO:40). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the unstructured peptide N-terminal to 8-chain structure in 1SY6 as uppercase italic and wavy underline, the CD3 ε-chain ecto-domain in uppercase bold, the juxtamembrane connecting peptide between the CD3 ε-chain ecto-domain and the trans-membrane domain in uppercase dotted underline.

FIGS. 17A-D depicts the DNA sequence and predicted protein sequence for an exemplary hybrid adalimumab heavy chain with CD3 γ-chain ecto-domain replacing CH3 domain. FIG. 17A depicts the DNA sequence encoding the hybrid molecule (SEQ ID NO:41). FIG. 17B depicts the predicted protein sequence of the hybrid molecule (SEQ ID NO:42). FIG. 17C depicts the DNA sequence encoding a CD3 γ-chain ecto-domain (SEQ ID NO:43). FIG. 17D depicts the predicted protein sequence of a CD3 γ-chain ecto-domain (SEQ ID NO:44). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the CD3 γ-chain ecto-domain in uppercase bold, the juxtamembrane connecting peptide between the CD3 γ-chain ecto-domain and the trans-membrane domain in uppercase dotted underline.

FIGS. 18A-D depicts the DNA sequence and predicted protein sequence for an exemplary hybrid adalimumab heavy chain with CD3 δ-chain ecto-domain replacing CH3 domain. FIG. 18A depicts the DNA sequence encoding the hybrid molecule (SEQ ID NO:45). FIG. 18B depicts the predicted protein sequence of the hybrid molecule (SEQ ID NO:46). FIG. 18C depicts the DNA sequence encoding a CD3 δ-chain ecto-domain (SEQ ID NO:47). FIG. 18D depicts the predicted protein sequence of a CD3 δ-chain ecto-domain (SEQ ID NO:48). The leader peptide and constant regions are shown in lowercase, and VH in uppercase. The CDR's are shaded grey and underlined. The CH1 is shown in lowercase italics, the hinge region in dotted underline, the CH2 domain in lowercase bold face, the flexible loop region separating CH2 domain from CH3 domain in lowercase double underline, the CD3 δ-chain ecto-domain in uppercase bold, the juxtamembrane connecting peptide between the CD3 δ-chain ecto-domain and the trans-membrane domain in uppercase dotted underline.

FIG. 19A Template for PCR amplification is clone GSB001 (Table 2). FIG. 19B Template for PCR amplification is clone GSB002 (Table 2). FIG. 19C PCR amplification products of light chain (LC, lanes 4, 5) and heavy chain (HC, lanes 6, 7)

FIG. 20A Amplification of common HC cassette from clone GSB003 indicated in Table 2. The yellow shaded region at the end of CH2 domain indicates a ~40 bp region of overlap with paired substitutions of CH3 domain indicated in FIG. 20B. FIG. 20B Amplification of unique paired substitutions for CH3 domain. X and Y denote paired domains indicated in examples 2-6 and listed as clones GSB004-GSB013 in Table 2, that can be substituted in place of the naturally occurring CH3 domain (found in antibody heavy chains) to effect assembly of heavy chain heterodimers during protein expression in mammalian cells. The yellow shaded region at the 5' end of each paired domain indicates a ~40 bp region of overlap with CH3 domain indicated in FIG. 20A. FIG. 20C PCR amplification products of the fragments illustrated in FIG. 20B. Gel #1 lanes 1-5 contain products amplified with gb primer pairs 5+6, 5+8, 5+10, 5+12 & 5+14 respectively. Gel #2 lanes 1-6 contain pcr products amplified with gb primer pairs 5+7, 5+9, 5+11, 5+13, 5+15, and 5+16, respectively. Lane 6 in gel #2 contains pcr product amplified from template GSB003 with gb primer pair 3+4a as shown in FIG. 20A.

FIG. 22 Agarose gels numbered 3-6 show the pcr amplified full length heavy chain fragments based on over-lap pcr scheme illustrated in FIG. 21 and the pcr reaction set up summarized in Table 4.

FIG. 26A. Adalimumab sample 1 and a mixture of equal parts samples 1, 2, & 3 as listed in Tabe 5. FIG. 26B. MHC I α1 and β2M as homodimers (diamond and triangle symbols, respectively) or heterodimer (square symbol). FIG. 26C MHC II α2 and MHC II β2 as homodimers (diamond and triangle symbols, respectively) or heterodimer (square symbol). FIG. 26D TCR Cα and TCR Cβ as homodimers (diamond and triangle symbols, respectively) or heterodimer (square symbol). FIG. 26E TCR Cγ and TCR Cδ2 as homodimers (diamond and triangle symbols, respectively) or heterodimer (square symbol). FIG. 26F CD3 ε and CD3 γ as homodimers (diamond and triangle symbols, respectively) or heterodimer (square symbol).

BRIEF DESCRIPTION OF THE SEQUENCES

Figure 1:
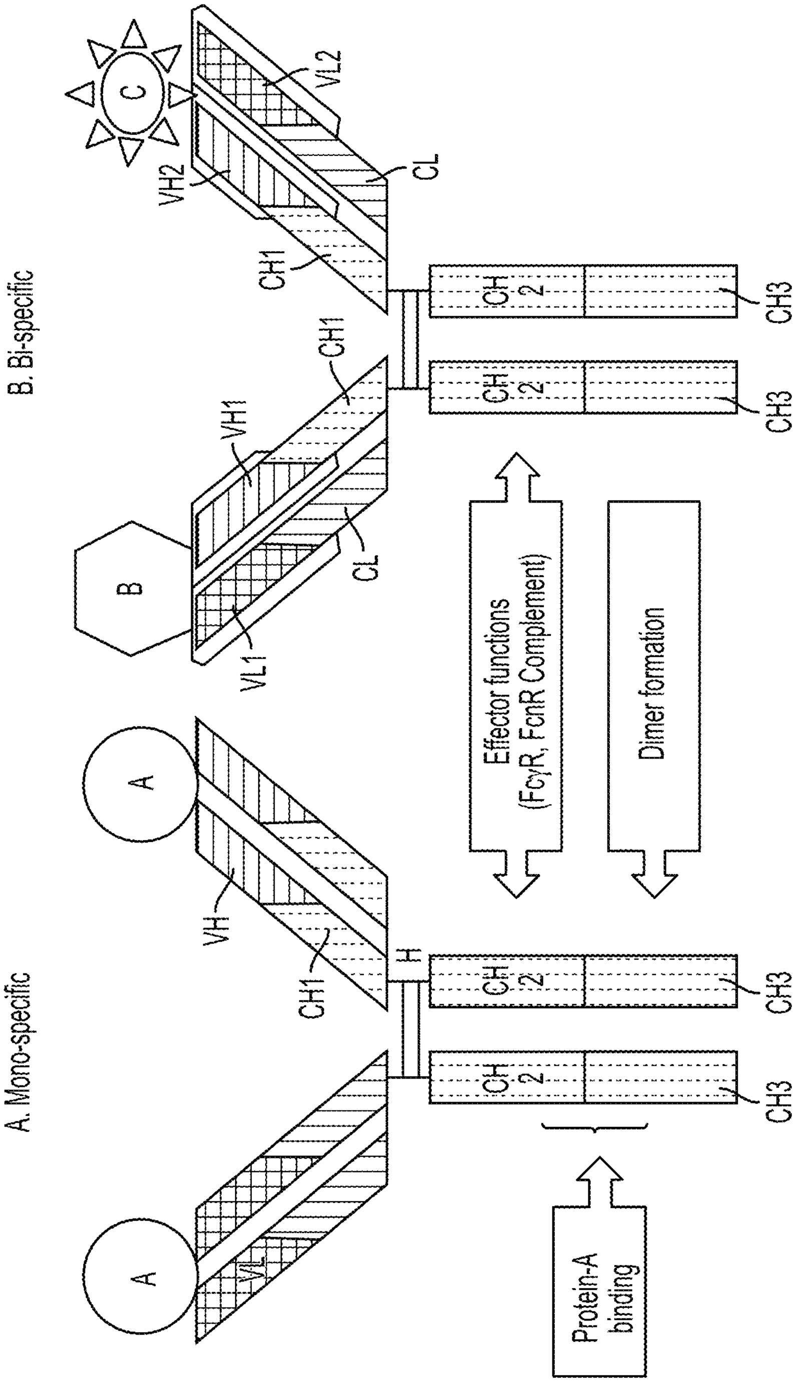
FIGS. 1A-B is a schematic illustration of structural domains in antibody molecules.
Figure 2:
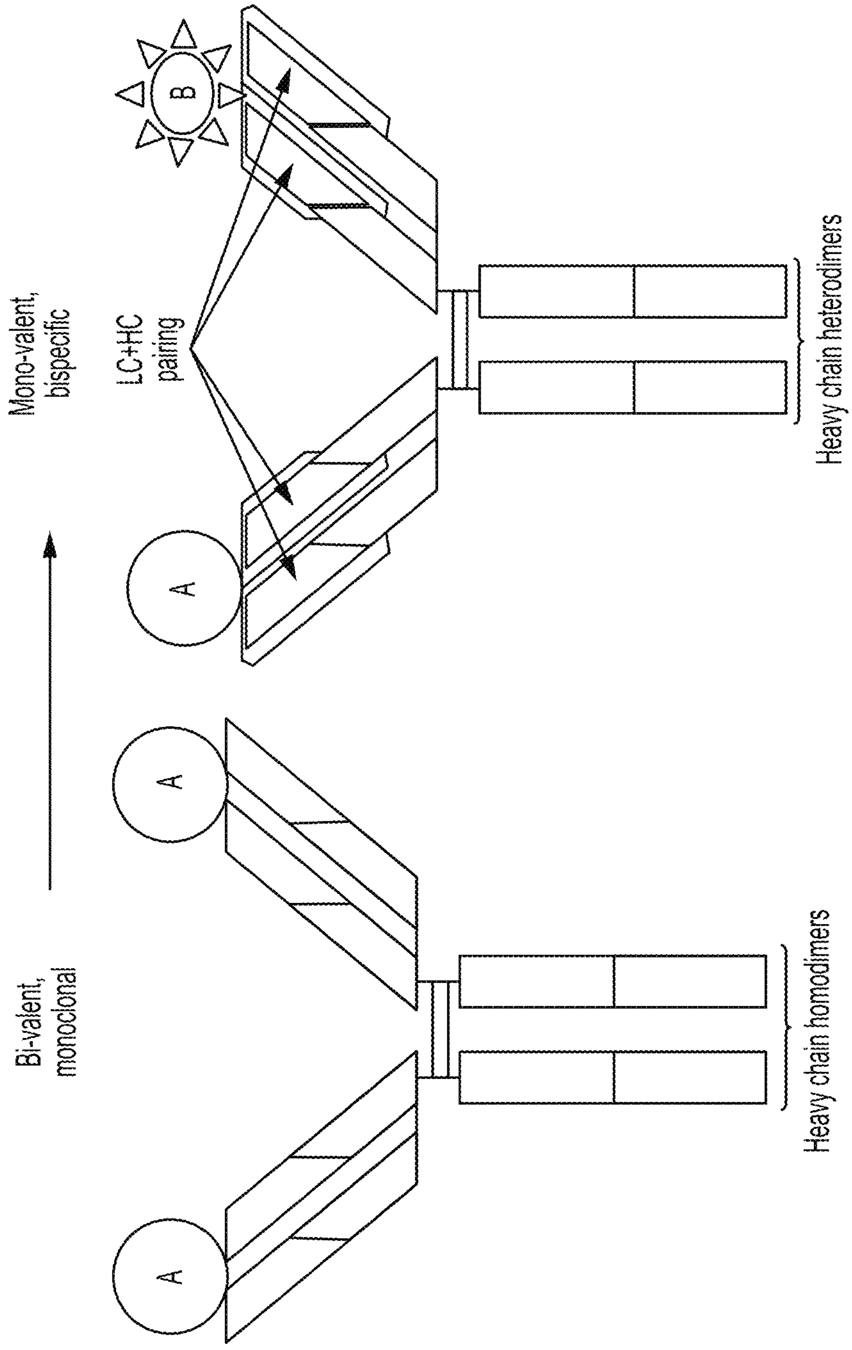
FIG. 2 is a schematic depiction of key requirements in engineering bi-specific antibodies as compared with conventional mono-specific antibodies. All annotations are as in FIG. 1.

Note: The typefaces associated with each sequence have the same meaning as indicated for FIGS. 6-18.

SEQ ID NO:1 sets forth a nucleic acid sequence encoding the adalimumab light chain (start codon, leader peptide and stop codon inclusive).

SEQ ID NO:2 sets forth the amino acid sequence of the adalimumab light chain (leader peptide inclusive).

SEQ ID NO:3 sets forth a nucleic acid sequence encoding the adalimumab heavy chain(start codon, leader peptide and stop codon inclusive).

SEQ ID NO:4 sets forth the amino acid sequence of the adalimumab heavy chain (leader peptide inclusive).

SEQ ID NO:5 sets forth a nucleic acid sequence encoding an exemplary adalimumab MHC-1α3 hybrid heavy chain (start codon, leader peptide and stop codon inclusive).

SEQ ID NO:6 sets forth the amino acid sequence of an exemplary adalimumab MHC-1α3 hybrid heavy chain (leader peptide inclusive).

SEQ ID NO:7 sets forth a nucleic acid sequence encoding an MHC I HLA-A (A*68 allele) α3 domain (stop codon inclusive).

SEQ ID NO:8 sets forth the amino acid sequence of an MHC I HLA-A (A*68 allele) α3 domain.

SEQ ID NO:9 sets forth a nucleic acid sequence encoding an exemplary adalimumab β2 microglobulin hybrid heavy chain (start codon, leader peptide and stop codon inclusive).

SEQ ID NO:10 sets forth the amino acid sequence of an exemplary adalimumab β2 microglobulin hybrid heavy chain (leader peptide inclusive).

SEQ ID NO:11 sets forth a nucleic acid sequence encoding a β2 microglobulin (stop codon inclusive).

SEQ ID NO:12 sets forth the amino acid sequence of a β2 microglobulin.

SEQ ID NO:13 sets forth a nucleic acid sequence encoding an exemplary adalimumab MHC II α2 domain (derived from HLA-DR alpha) hybrid heavy chain (start codon, leader peptide and stop codon inclusive).

SEQ ID NO:14 sets forth the amino acid sequence of an exemplary adalimumab MHC II α2 domain (derived from HLA-DR alpha) hybrid heavy chain (leader peptide inclusive).

SEQ ID NO:15 sets forth a nucleic acid sequence encoding an MHC II α2 domain from HLA-DR alpha (stop codon inclusive).

SEQ ID NO:16 sets forth the amino acid sequence of an MHC II α2 domain from HLA-DR alpha.

SEQ ID NO:17 sets forth a nucleic acid sequence encoding an exemplary adalimumab MHC II β2 domain (derived from HLA-DR beta1) hybrid heavy chain (start codon, leader peptide and stop codon inclusive).

SEQ ID NO:18 sets forth the amino acid sequence of an exemplary adalimumab MHC II β2 domain (derived from HLA-DR beta1) hybrid heavy chain (leader peptide inclusive).

SEQ ID NO:19 sets forth a nucleic acid sequence encoding an MHC II β2 domain from HLA-DR beta1 (stop codon inclusive).

SEQ ID NO:20 sets forth the amino acid sequence of an MHC II β2 domain from HLA-DR beta1.

SEQ ID NO:21 sets forth a nucleic acid sequence encoding an exemplary adalimumab TCR Cα domain hybrid heavy chain (start codon, leader peptide and stop codon inclusive).

SEQ ID NO:22 sets forth the amino acid sequence of an exemplary adalimumab TCR Cα domain hybrid heavy chain (leader peptide inclusive).

SEQ ID NO:23 sets forth a nucleic acid sequence encoding a TCR Cα domain (stop codon inclusive).

SEQ ID NO:24 sets forth the amino acid sequence of a TCRCα domain.

SEQ ID NO:25 sets forth a nucleic acid sequence encoding an exemplary adalimumab TCR Cβ domain hybrid heavy chain (start codon, leader peptide and stop codon inclusive).

SEQ ID NO:26 sets forth the amino acid sequence of an exemplary adalimumab TCR Cβ domain hybrid heavy chain (leader peptide inclusive).

SEQ ID NO:27 sets forth a nucleic acid sequence encoding a TCR Cβ domain (stop codon inclusive).

SEQ ID NO:28 sets forth the amino acid sequence of a TCR Cβ domain.

SEQ ID NO:29 sets forth a nucleic acid sequence encoding an exemplary adalimumab TCR Cγ domain hybrid heavy chain (start codon, leader peptide and stop codon inclusive).

SEQ ID NO:30 sets forth the amino acid sequence of an exemplary adalimumab TCR Cγ domain hybrid heavy chain (leader peptide inclusive).

SEQ ID NO:31 sets forth a nucleic acid sequence encoding a TCR Cγ domain (stop codon inclusive).

SEQ ID NO:32 sets forth the amino acid sequence of a TCRCγ domain.

SEQ ID NO:33 sets forth a nucleic acid sequence encoding an exemplary adalimumab TCR Cδ domain hybrid heavy chain (start codon, leader peptide and stop codon inclusive).

SEQ ID NO:34 sets forth the amino acid sequence of an exemplary adalimumab TCR Cδ domain hybrid heavy chain (leader peptide inclusive).

SEQ ID NO:35 sets forth a nucleic acid sequence encoding a TCR Cδ domain (stop codon inclusive).

SEQ ID NO:36 sets forth the amino acid sequence of a TCRCδ domain.

SEQ ID NO:37 sets forth a nucleic acid sequence encoding an exemplary adalimumab CD3 ε-chain ecto-domain hybrid heavy chain (start codon, leader peptide and stop codon inclusive).

SEQ ID NO:38 sets forth the amino acid sequence of an exemplary adalimumab CD3 ε-chain ecto-domain hybrid heavy chain (leader peptide inclusive).

SEQ ID N0:39 sets forth a nucleic acid sequence encoding a CD3 ε-chain ecto-domain (stop codon inclusive).

SEQ ID NO:40 sets forth the amino acid sequence of a CD3 ε-chain ecto-domain.

SEQ ID NO:41 sets forth a nucleic acid sequence encoding an exemplary adalimumab CD3 γ-chain ecto-domain hybrid heavy chain (start codon, leader peptide and stop codon inclusive).

SEQ ID NO:42 sets forth the amino acid sequence of an exemplary adalimumab CD3 γ-chain ecto-domain hybrid heavy chain (leader peptide inclusive).

SEQ ID NO:43 sets forth a nucleic acid sequence encoding a CD3 γ-chain ecto-domain (stop codon inclusive).

SEQ ID NO:44 sets forth the amino acid sequence of a CD3 γ-chain ecto-domain.

SEQ ID NO:45 sets forth a nucleic acid sequence encoding an exemplary adalimumab CD3 δ-chain ecto-domain hybrid heavy chain (start codon, leader peptide and stop codon inclusive).

SEQ ID NO:46 sets forth the amino acid sequence of an exemplary adalimumab CD3 δ-chain ecto-domain hybrid heavy chain (leader peptide inclusive).

SEQ ID NO:47 sets forth a nucleic acid sequence encoding a CD3 δ-chain ecto-domain (stop codon inclusive).

SEQ ID NO:48 sets forth the amino acid sequence of a CD3 δ-chain ecto-domain.

SEQ ID NO:49 sets forth the nucleic acid sequence of an exemplary CH1 domain.

SEQ ID NO:50 sets forth the amino acid sequence of an exemplary CH1 domain.

SEQ ID NO:51 sets forth the nucleic acid sequence of an exemplary hinge region.

SEQ ID NO:52 sets forth the amino acid sequence of an exemplary hinge region.

SEQ ID NO:53 sets forth the nucleic acid sequence of an exemplary CH2 domain.

SEQ ID NO:54 sets forth the amino acid sequence of an exemplary CH2 domain.

SEQ ID NO:55 sets forth the nucleic acid sequence of an exemplary CH3 domain.

SEQ ID NO:56 sets forth the amino acid sequence of an exemplary CH3 domain.

SEQ ID NO:57 sets forth a nucleic acid sequence encoding an exemplary adalimumab MHC-1 HLA-A (A*68 allele) α3 hybrid heavy chain.

SEQ ID NO:58 sets forth the amino acid sequence of an exemplary adalimumab MHC-1 HLA-A (A*68 allele) α3 hybrid heavy chain.

SEQ ID N0:59 sets forth a nucleic acid sequence encoding an exemplary adalimumab β2 microglobulin hybrid heavy chain.

SEQ ID NO:60 sets forth the amino acid sequence of an exemplary adalimumab β2 microglobulin hybrid heavy chain.

SEQ ID NO:61 sets forth a nucleic acid sequence encoding an exemplary adalimumab MHC II α2 domain (from HLA-DR alpha) hybrid heavy chain.

SEQ ID NO:62 sets forth the amino acid sequence of an exemplary adalimumab MHC II α2 domain (from HLA-DR alpha) hybrid heavy chain.

SEQ ID NO:63 sets forth a nucleic acid sequence encoding an exemplary adalimumab MHC II β2 domain (from HLA-DR beta1) hybrid heavy chain.

SEQ ID NO:64 sets forth the amino acid sequence of an exemplary adalimumab MHC II β2 domain (from HLA-DR beta1) hybrid heavy chain.

SEQ ID NO:65 sets forth a nucleic acid sequence encoding an exemplary adalimumab TCR Cα domain hybrid heavy chain.

SEQ ID NO:66 sets forth the amino acid sequence of an exemplary adalimumab TCR Cα domain hybrid heavy chain.

SEQ ID NO:67 sets forth a nucleic acid sequence encoding an exemplary adalimumab TCR Cβ domain hybrid heavy chain.

SEQ ID NO:68 sets forth the amino acid sequence of an exemplary adalimumab TCR Cβ domain hybrid heavy chain.

SEQ ID NO:69 sets forth a nucleic acid sequence encoding an exemplary adalimumab TCR Cγ domain hybrid heavy chain.

SEQ ID NO:70 sets forth the amino acid sequence of an exemplary adalimumab TCR Cγ domain hybrid heavy chain.

SEQ ID NO:71 sets forth a nucleic acid sequence encoding an exemplary adalimumab TCR Cδ domain hybrid heavy chain.

SEQ ID NO:72 sets forth the amino acid sequence of an exemplary adalimumab TCR Cδ domain hybrid heavy chain.

SEQ ID NO:73 sets forth a nucleic acid sequence encoding an exemplary adalimumab CD3 ε-chain ecto-domain hybrid heavy chain.

SEQ ID NO:74 sets forth the amino acid sequence of an exemplary adalimumab CD3 ε-chain ecto-domain hybrid heavy chain.

SEQ ID NO:75 sets forth a nucleic acid sequence encoding an exemplary adalimumab CD3 γ-chain ecto-domain hybrid heavy chain.

SEQ ID NO:76 sets forth the amino acid sequence of an exemplary adalimumab CD3 γ-chain ecto-domain hybrid heavy chain.

SEQ ID NO:77 sets forth a nucleic acid sequence encoding an exemplary adalimumab CD3 δ-chain ecto-domain hybrid heavy chain.

SEQ ID NO:78 sets forth the amino acid sequence of an exemplary adalimumab CD3 δ-chain ecto-domain hybrid heavy chain.

SEQ ID NO:79 sets forth a nucleic acid sequence encoding an MHC I HLA-A (A*68 allele) α3 domain.

SEQ ID NO:80 sets forth a nucleic acid sequence encoding a β2 microglobulin.

SEQ ID NO:81 sets forth a nucleic acid sequence encoding an MHC II α2 domain from HLA-DR alpha.

SEQ ID NO:82 sets forth a nucleic acid sequence encoding an MHC II β2 domain from HLA-DR beta1.

SEQ ID NO:83 sets forth a nucleic acid sequence encoding a TCR Cα domain.

SEQ ID NO:84 sets forth a nucleic acid sequence encoding a TCR CP domain.

SEQ ID NO:85 sets forth a nucleic acid sequence encoding a TCR Cγ domain.

SEQ ID NO:86 sets forth a nucleic acid sequence encoding a TCR Cδ domain.

SEQ ID NO:87 sets forth a nucleic acid sequence encoding a CD3 ε-chain ecto-domain.

SEQ ID NO:88 sets forth a nucleic acid sequence encoding a CD3 γ-chain ecto-domain.

SEQ ID NO:89 sets forth a nucleic acid sequence encoding a CD3 δ-chain ecto-domain.

DEFINITIONS

The heterodimeric bispecific antibodies (HBA's) or heterodimeric bispecific Fc fusion proteins (HBFP's) are typically provided in isolated form. This means that an HBA or HBFP is typically at least 50% w/w pure of interfering proteins and other contaminants arising from its production or purification but does not exclude the possibility that the HBA or HBFP is combined with an excess of pharmaceutical accepTable carrier(s) or other vehicle intended to facilitate its use. Sometimes HBA's or HBFP's are at least 60, 70, 80, 90, 95 or 99% w/w pure of interfering proteins and contaminants from production or purification. Often an HBA or HBFP is the predominant macromolecular species remaining after its purification.

Specific binding of an HBA or HBFP to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an HBA or HBFP binds one and only one target.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the HBA's of the invention have been expressed and secreted. A pair of heavy and light chain variable regions, or heavy chain variable region alone as in the case of Camelids or engineered mimetics thereof, defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcRn binding. Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is bivalent. In natural antibodies, the binding sites are the same. However, bispecific antibodies can be made in which the two binding sites are different (see, e.g., Songsivilai and Lachmann, *Clin. Exp. Immunol.,* 79:315-321 (1990); Kostelny et al., *J. Immunol.,* 148:1547-53 (1992)). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chain variable regions or between different light chain variable regions are assigned the same number. Although Kabat numbering can be used for antibody constant regions, the EU index is more commonly used, as is the case in this application.

In a mono-specific bivalent antibody, the two heavy chain and two light chain variable regions are the same. In a bispecific bivalent antibody, there are two different heavy and light chain variable region pairings or "arms" with different binding specificities.

The term "antibody" includes any form of antibody with at least one binding region including monovalent fragments, bivalent tetrameric units of two heavy chains and light chains, and higher order complexes, particularly trimers, tetramers and pentamers of bivalent units. An antibody can be mono-specific in which case all binding regions have the same specificity or multi-specific in which the binding sites have at least two specificities.

The term "epitope" refers to a site on an antigen to which an antibody or HBA binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. Some antibodies bind to an end-specific epitope, meaning an antibody binds preferentially to a polypeptide with a free end relative to the same polypeptide fused to another polypeptide resulting in loss of the free end. An epitope typically includes at least 3, and more usually, at least 5 or 8-10 amino acids in a unique spatial conformation. Methods of determining spatial conformation of epitopes include, for example, x-ray crystallography, cryo-electron microscopy, and 2-dimensional nuclear magnetic resonance. See, e.g., Epitope Mapping Protocols, in *Methods in Molecular Biology*, Vol. 66, Glenn E. Morris, Ed. (1996).

The term "antigen" or "target antigen" indicates a target molecule bound by an antibody. An antigen may be a protein of any length (natural, synthetic or recombinantly expressed), a nucleic acid or carbohydrate among other molecules. Antigens include receptors, ligands, counter receptors, and coat proteins.

A heterologous polypeptide in a fusion protein is a polypeptide not naturally linked to an immunoglobulin constant region. Such a polypeptide can be a full-length protein or any fragment thereof of sufficient length to retain specific binding to the antigen or ligand bound by the full-length protein. For example, a heterologous polypeptide can be a receptor extracellular domain or ligand thereto.

The term "fused" when used in describing the structure of heterodimeric bispecific antibodies or heterodimeric bispecific fusion proteins means that the segments in question are either directly connected or connected through intervening amino acids.

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. For other proteins, sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), or BLAST (basic local alignment search tool) as defined in the national center for biotechnology information web site (world wide web blast.ncbi.nlm.nih.gov/Blast.cgi), using default gap parameters, or by inspection, and the best alignment. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al., *J. Immunol.* 169:3076, 2002; Vajdos et al., *Journal of Molecular Biology,* 320: 415-428, 2002; Iwahashi et al., *Mol. Immunol.* 36:1079-1091, 1999; Tamura et al, *Journal of Immunology,* 164:1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, *Mol. Immunol.* 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

A human antibody can be isolated from a human, or otherwise result from expression of human immunoglobulin genes (e.g., in a transgenic mouse, in vitro or by phage display). Methods for producing human antibodies include the trioma method of Oestberg et al., *Cys muoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991) and phage display methods (see, e.g.

Dower et al., WO 91/17271 and McCafferty et al., WO 92/01047, U.S. Pat. Nos. 5,877,218, 5,871,907, 5,858,657, 5,837,242, 5,733,743 and 5,565,332.

DETAILED DESCRIPTION

General

The invention provides bispecific heterodimeric antibodies with modified heavy chain IgG constant regions that promote efficient assembly of antibody heavy chain heterodimer pairs, as well as arm specific pairing of heavy and light chains. Some antibodies of the invention have modified light chain constant regions that promote arm specific pairing of the modified light chain with the desired heavy chain for efficient assembly of antibody light chain+heavy chain heterodimer pairs. A heterodimeric bispecific antibody as described herein comprises two polypeptide chains having different amino acid sequences, which, together, can bind to two different antigens, or two different epitopes on the same antigen.

The heterodimeric antibodies include heterologous components derived from polypeptides or proteins, e.g. the immunoglobulin superfamily (IgSF), that naturally occur as heterodimers, or are engineered to assemble as heterodimers during expression in cells or in-vitro. As used herein, the term “IgSF” excludes antibody domains. Domains from the IgSF in place of CH3 domain and/or the CH1+CL domain of the antibody heavy and light chains mediate the correct assembly of the bispecific antibodies, thereby reducing mispaired contaminants and enhancing overall product purity and yield.

Antibodies

The heterodimeric bispecific antibodies of the invention (HBA’s) specifically bind to different targets. The targets can be completely different target proteins or antigens, or can be different epitopes within a common target protein or antigen. Thus, the HBA comprises a first antigen recognizing moiety (A) and a second antigen recognizing moiety (B), where A and B bind to different target proteins or antigens or different epitopes within a common target protein or antigen.

The first antigen recognizing moiety (A) has a light chain variable region (VL1) fused to a light chain constant region (CL). VL1 can be either humanized, fully human, or non-human. A also has a heavy chain variable region (VH1) fused to a heavy chain constant domain (CH1), which is fused to a heterologous molecule in place of CH3 (X). The term “fused” VH1 can be either humanized, fully human, or non-human. The heterologous polypeptide is derived from a component within the immunoglobulin superfamily (IgSF) that can form heterodimers with at least one other component from the IgSF (pairing partner). In some HBA’s of the invention, the CH1 is fused to X through an antibody hinge region (H). In some HBA’s, CH1 and X are fused through constant heavy chain region CH2 and in some HBA’s, CH1 is fused to CH2 through H. CL can be Cκ light chain constant region or Cλ light chain constant region. CH1, H and CH2 can be from any of the heavy chain constant region isotypes, such as, for example, human IgA, IgD, IgE, IgM, IgG1, IgG2, IgG3 and IgG4. In some HBA’s VL1 is fused directly to VH1.

The second antigen recognizing moiety (B) has a light chain variable region (VL2), which is different from VL1. VL2 can be either humanized, fully human, or non-human. To promote appropriate pairing of the light and heavy chains of B, in place of CL, VL2 is fused to a heterologous polypeptide (m) in place of CL. This heterologous polypeptide is derived from the IgSF that is not X or the pairing partner for X. B also has a heavy chain variable region (VH2), which is different from VH1. VH2 can be either humanized, fully human, or non-human. VH2 is fused to heterologous polypeptide in place of CH1 (n). n is derived from the IgSF pairing partner for m, and is fused to the IgSF pairing partner for X in place of CH3 (Y). In some HBA’s n is fused to Y through CH2. In some HBA’s, n is fused to Y through H and in some HBA’s n is fused to Y through H and CH2. To effect optimal assembly of the antibody heavy and light chains, m and n of the m/n binding pair are different from both X and Y of the X/Y binding pair in any given HBA. In some HBA’s, VL2 is fused directly to VH2.

In some HBA’s, the CL, CH1 and CH2 are derived from the corresponding mono-specific antibody from which the HBA is derived.

IgSF Domains for Promoting Assembly of Heavy Chain Heterodimers

Some of the heterodimeric antibodies of the invention involve a replacement of the homo-dimer promoting CH3 domain with protein domains that adopt the canonical immunoglobulin fold (Bork et al. 1994*; Smith and Xue* 1997; Barclay 2003) and have the same pfam identifier as native CH3. Table 1 lists a set of representative naturally occurring heterodimers in the immunoglobulin superfamily (IgSF) that meet these criteria.

TABLE 1

Heterodimers from the IgSF and the domains mediating heterodimer assembly of the respective chains. TCR AgR denotes the antigen receptor on T-cells. C-indicates constant region.

| Chain-a (X) | pfam id | pdb id | NCBI acc# | Chain-b (Y) | pfam id | pdb id | NCBI acc # |
|---|---|---|---|---|---|---|---|
| CH3 | C1-set | 1L6X | Z17370 | CH3 | C1-set | 1L6X | Z17370 |
| MHC I or homolog α3 domain | C1-set | 2HLA | AJ245567 | β2M | C1-set | 2HLA | NM_004048 |
| MHC II α2 domain | C1-set | 1DLH | NM_019111 | MHC II β2 domain | C1-set | 1DLH | NM_002124 |
| TCR AgR Cα domain | C1-set | 1QSF | AK301287 | TCR AgR Cβ domain | C1-set | 1QSF | BC110303 |
| TCR AgR Cγ domain | C1-set | 1HXM | BC072396 | TCR AgR Cδ domain | C1-set | 1HXM | AK303149 |
| TCR CD3 ε-chain ecto-domain | I-set | 1SY6 | X03884 | TCR CD3 γ-chain ecto-domain | I-set | 1SY6 | NM_000073 |

TABLE 1-continued

Heterodimers from the IgSF and the domains mediating heterodimer assembly of the respective chains. TCR AgR denotes the antigen receptor on T-cells. C-indicates constant region.

| Chain-a (X) | pfam id | pdb id | NCBI acc# | Chain-b (Y) | pfam id | pdb id | NCBI acc # |
|---|---|---|---|---|---|---|---|
| TCR CD3 ε-chain ecto-domain | I-set | 1XIW | X03884 | TCR CD3 δ-chain ecto-domain | I-set | 1XIW | BC039035 |

Thus, the X/Y binding pair can be derived from any of a number of IgSF heterodimers meeting the above criteria, including MHC class I molecules (MHC I), MHC class II molecules (MHC II) and T-Cell receptor complex of molecules (TCR).

The domain swap of CH3 in antibody heavy chain with domains from molecules that naturally exist as heterodimer pairs drives assembly of heavy chain heterodimers for the production of bi-specific antibodies, as illustrated in FIGS. 3A-D. The case of β2 microglobulin (β2m) as "light chain" component of a heterodimer pair with α3 domain from MHC-1 presents an opportunity for increased combinatorial diversity of MHC-1 α3 like-domains, as β2m has been documented to assemble as a heterodimer with a number of MHC-1 homologs, listed in Table 2.

TABLE 2

MHC-I homologs documented to assemble as heterodimers with β2microglobulin.

| Heavy Chain | Light Chain |
|---|---|
| MHC I haplotypes (HLA-A, B, C, D, E, F, G) | β2 microglobulin |
| FcRn | |
| CD1(a, b, c, d, e) | |
| HCMV UL18 (H301 gene) | |

Thus, in addition to α3 domain from any of the MHC-1 haplotypes listed in Table 2, one may substitute the α3 domain from the cognate MHC-1 heavy chains listed in Table 2 to equal or better effect in promoting heterodimerization of antibody heavy chains.

Four basic formats comprised of heterodimer heavy chains can be envisioned as illustrated schematically in FIGS. 3A-D where CH3 domain has been replaced by an X/Y binding pair, for example, a heterodimer pair selected from Table 1, an Fab'2 equivalent (FIG. 3A); a full antibody equivalent (FIG. 3B); an "extended format" antibody utilizing an additional binding pair derived from a heterodimer within the IgSF (p/q binding pair). In some HBA's, the heterodimer pair selected from Table 1 is duplicated in tandem (FIG. 3C). In this case the p/q binding pair is identical to the X/Y binding pair. Alternatively, the p/q binding pair is a different heterodimer pair, for example, selected from Table 1 (FIG. 3D). The p/q binding pair can also be derived from any of a number of IgSF heterodimers meeting the above criteria, including MHC class I molecules (MHC I), MHC class II molecules (MHC II) and T-Cell receptor complex of molecules (TCR). The extended formats illustrated in FIGS. 3C and 3D may confer more efficient assembly of, or stability to, the heterodimer, in addition to facilitating purification by affinity chromatography during manufacture.

Promoting Appropriate Pairing of Heavy and Light Chains

The approach illustrated schematically in FIGS. 3A-D can be employed in a combinatorial manner with a given heterodimeric heavy chain combination to effect appropriate pairing of the heavy chain with a particular light chain in an "arm specific" manner, as illustrated in FIGS. 4A-D. To effect arm specific pairing of light chains, the CH1 domain of the heavy chain and the corresponding CL (e.g., Cκ Cλ) domain on the light chain of an arm are replaced by heterodimer forming domains from, for example, the molecules listed in Tables 1 and 2. For example, a paired domain swap of CH1 domain on one heavy chain and the Cκ domain of the corresponding light chain with cognate domains from a different set of heterodimer promoting domains (an m/n pair) are used to effect "arm-specific" pairing of light chains with heterodimer heavy chains (FIG. 4B). This rule can be applied to a bispecific antibody of extended format in which an X/Y pairs is duplicated in tandem manner, as illustrated in FIG. 4C, or in combination with a different p/q pair as illustrated in FIG. 4D, to effect more efficient assembly of, or confer more stability to, the heterodimer heavy chains. For optimal assembly of the antibody heavy and light chains, m and n of the m/n binding pair are different from both X and Y of the X/Y binding pair and both p and q of the p/q binding pair in any given HBA.

Tables 3-9 list some combinatorial solutions for domain matching of any given X/Y pair in place of CH3 on the heavy chains with potential m/n pairs in place of CH1 and CL (Cκ or Cλ) domains on the heavy chain and light chain, respectively. For proper assembly, m and n are different from X and Y. Some heterodimeric bispecific antibodies may additionally include an extended domain p/q as shown in FIGS. 4C and 4D. Some of such p/q binding pairs are identical to the X/Y binding pairs, such that p=X and q=Y. For other heterodimeric bispecific antibodies, p and q are different from X and Y and different from m and n. For some heterodimeric bispecific antibodies, one heavy chain contains a swap of CH3 domain only (single swap heavy chain), while the second heavy chain contains a swap of both the CH1 and CH3 domains (double swap heavy chain). The single swap heavy chain, with a natural CH1 domain, would be expected to pair with a light chain containing the Ck (or Cλ) domain found on natural antibody light chains. Table 3 summarizes some potential permutations of components. As indicated in Table 3, one may select any binding pair of components from the immunoglobulin superfamily as X and Y (the CH3 substitutions). For an extended heavy chain, one can optionally include any binding pair of components from the immunoglobulin superfamily, provided that p and q are different from X and Y or duplicate the pair in positions X and Y (i.e., p=X and q=Y). One can also select a binding pair of components from the superfamily as m and n (the substitutions for CL and CH1), provided that m and n are different from X and Y and p and q (i.e., m≠X, Y, p or q and n≠X, Y, p or q).

TABLE 3

Summary of some potential permutations of heterodimeric bispecific antibody components.

| X/Y Pair Select any pair Substituted for CH3 (A and B moieties, respectively) | | p/q Pair p = X and q = Y (select same pair as selected for X/Y) or p/q ≠ X/Y or Y/X(select different pair from that selected for X/Y) Heavy chain extension (A and B moieties, respectively) | | m/n Pair m/n ≠ X/Y or Y/X (select different pair from that selected for X/Y) m/n ≠ p/q or q/p (select different pair from that selected for p/q) Substituted for CL and CH1, respectively (B moiety only) | |
|---|---|---|---|---|---|
| X | Y | p | q | m | n |
| MHC I α3 domain | β-2 microglobulin | MHC I α3 domain | β-2 microglobulin | MHC I α3 domain | β-2 microglobulin |
| β-2 microglobulin | MHC I α3 domain | β-2 microglobulin | MHC I α3 domain | β-2 microglobulin | MHC I α3 domain |
| Any MHC component listed in Table 2 | β-2 microglobulin | Any MHC component listed in Table 2 | β-2 microglobulin | Any MHC component listed in Table 2 | β-2 microglobulin |
| β-2 microglobulin | Any MHC component listed in Table 2 | β-2 microglobulin | Any MHC component listed in Table 2 | β-2 microglobulin | Any MHC component listed in Table 2 |
| MHC II α2 domain | MHC II β2 domain | MHC II α2 domain | MHC II β2 domain | MHC II α2 domain | MHC II β2 domain |
| MHC II β2 domain | MHC II α2 domain | MHC II β2 domain | MHC II α2 domain | MHC II β2 domain | MHC II α2 domain |
| TCR Cα | TCR Cβ | TCR Cα | TCR Cβ | TCR Cα | TCR Cβ |
| TCR Cβ | TCR Cα | TCR Cβ | TCR Cα | TCR Cβ | TCR Cα |
| TCR Cγ | TCR Cδ | TCR Cγ | TCR Cδ | TCR Cγ | TCR Cδ |
| TCR Cδ | TCR Cγ | TCR Cδ | TCR Cγ | TCR Cδ | TCR Cγ |
| CD3 ε-chain | CD3 γ-chain | CD3 ε-chain | CD3 γ-chain | CD3 ε-chain | CD3 γ-chain |
| CD3 γ-chain | CD3 ε-chain | CD3 γ-chain | CD3 ε-chain | CD3 γ-chain | CD3 ε-chain |
| CD3 ε-chain | CD3 δ-chain | CD3 ε-chain | CD3 δ-chain | CD3 ε-chain | CD3 δ-chain |
| CD3 δ-chain | CD3 ε-chain | CD3 δ-chain | CD3 ε-chain | CD3 δ-chain | CD3 ε-chain |

As indicated in Table 3, for any given binding pair, the specific positions can be reversed. For example, Table 4 is not limited to the specific positions within each binding pair shown. Table 4 is intended to encompass HBA's in which X is MHC I (or homolog) α3 domain and Y is β2m, and in which m is MHC II β2 domain and n is MHC II α2 domain or m is TCR AgR Cβ domain and n is TCR AgR Cα domain or m is TCR AgR Cδ domain and n is TCR AgR Cγ domain or m is TCR CD3 γ-chain and n is TCR CD3 ε-chain or m is TCR CD3 δ-chain and n is TCR CD3 ε-chain. The same rationale for selecting from among the various possible permutations applies for each of the HBA's of the inventions, including those listed in any of Tables 3-10.

TABLE 4

Some possible solutions for m and n where X and Y are MHC-I and β2m, or vice-versa.

| X | Y | m | n |
|---|---|---|---|
| MHC I (or homolog) α3 domain | β2m | MHC II α2 domain | MHC II β2 domain |
| | | TCR AgR Cα domain | TCR AgR Cβ domain |
| | | TCR AgR Cγ domain | TCR AgR Cδ domain |
| | | TCR CD3 ε-chain | TCR CD3 γ-chain |
| | | TCR CD3 ε-chain | TCR CD3 δ-chain |

In some HBA's, when the X/Y binding pair is derived from MHC II, the m/n binding pair is derived from MHC I or TCR. Some X/Y binding pairs include MHC II α2 domain and MHC II β2 domain. In some such HBA's, X is MHC II α2 domain and Y is MHC II β2 domain or X and Y are MHC II β2 domain and MHC II α2 domain, respectively, and m and n can be MHC I α3 domain and β2M, respectively, or β2M and MHC I α3 domain, respectively. For example, in some HBA's, X is MHC II α2 domain, Y is MHC II β2 domain, m is MHC I α3 domain and n is β2M. In other HBA's, X is MHC II β2 domain, Y is MHC II α2 domain, m is β2M and n is MHC I α3 domain. The same rationale can be applied to select for the HBA's of the invention the X/Y binding pairs and m/n binding pairs from among the various possible permutations of IgSF pairing partners, including those listed in any of Tables 3-10.

TABLE 5

Some possible solutions for m and n where X and Y are MHC-II α2 & β2 domains or vice-versa.

| X | Y | m | n |
|---|---|---|---|
| MHC II α2 domain | MHC II β2 domain | MHC I (or homolog) α3 domain | β2m |

TABLE 5-continued

| Some possible solutions for m and n where X and Y are MHC-II α2 & β2 domains or vice-versa. | | | |
|---|---|---|---|
| X | Y | m | n |
| | | TCR AgR Cα domain | TCR AgR Cβ domain |
| | | TCR AgR Cγ domain | TCR AgR Cδ domain |
| | | TCR CD3 ε-chain | TCR CD3 γ-chain |
| | | TCR CD3 ε-chain | TCR CD3 δ-chain |

In some HBA's, when the X/Y binding pair is derived from TCR, the m/n binding pair is derived from MHC I, MHC II or TCR. The X/Y binding pair can be TCR AgR Cα domain and TCR AgR Cβ domain and the m/n binding pair can be selected from the m and n pairing partners listed in Table 6.

TABLE 6

| Some possible solutions for m and when X and Y are TCR Cα & Cβ domains or vice-versa. | | | |
|---|---|---|---|
| X | Y | m | n |
| TCR AgR Cα domain | TCR AgR Cβ domain | MHC I (or homolog) α3 domain | β2m |
| | | MHC II α2 domain | MHC II β2 domain |
| | | TCR AgR Cγ domain | TCR AgR Cδ domain |
| | | TCR CD3 ε-chain | TCR CD3 γ-chain |
| | | TCR CD3 ε-chain | TCR CD3 δ-chain |

The X/Y binding pair of some HBA's is TCR AgR Cγ domain and TCR AgR Cδ domain and the m/n binding pair can be selected from the m and n pairing partners listed in Table 7.

TABLE 7

| Some possible solutions for m and n when X and Y are TCR Cγ & Cδ domains or vice-versa. | | | |
|---|---|---|---|
| X | Y | m | n |
| TCR AgR Cγ domain | TCR AgR Cδ domain | MHC I (or homolog) α3 domain | β2m |
| | | MHC II α2 domain | MHC II β2 domain |
| | | TCR AgR Cα domain | TCR AgR Cβ domain |
| | | TCR CD3 ε-chain | TCR CD3 γ-chain |
| | | TCR CD3 ε-chain | TCR CD3 δ-chain |

For some HBA's, the X/Y binding pair is TCR CD3 ε chain and TCR CD3 γ chain and the m binding pair can be selected from the m and n pairing partners listed in Table 8.

TABLE 8

| Some possible solutions for m and n when X and Y are ectodomains from CD3 ε & γ chain or vice-versa. In some antibodies, the ε-chain ectodomain is only on the double swap heavy chain only. | | | |
|---|---|---|---|
| X | Y | m | n |
| TCR CD3 ε-chain ecto-domain | TCR CD3 γ-chain ecto-domain | MHC I (or homolog) α3 domain | β2m |
| | | MHC II α2 domain | MHC IIβ2 domain |
| | | TCR AgR Cα domain | TCR AgR Cβ domain |
| | | TCR AgR Cγ domain | TCR AgR Cδ domain |
| | | TCR CD3 ε-chain ecto-domain | TCR CD3 δ-chain ecto-domain |

The X/Y binding pair for some HBA's is TCR CD3 chain and TCR CD3 δ chain and the/n binding pair can be selected from the m and n pairing partners listed in Table 9.

TABLE 9

| Some possible solutions for m and n when X and Y are ectodomains from CD3 ε & δ chain or vice-versa. In this instance, the ε-chain ectodomain would likely have to be on the double swap heavy chain only. | | | |
|---|---|---|---|
| X | Y | m | n |
| TCR CD3 ε-chain ecto-domain | TCR CD3 δ-chain ectodomain | MHC I (or homolog) α3 domain | β2m |
| | | MHC II α2 domain | MHC II β2 domain |
| | | TCR AgR Cα domain | TCR AgR Cβ domain |
| | | TCR AgR Cγ domain | TCR AgR Cδ domain |
| | | TCR CD3 ε chain | TCR CD3 γ-chain |

Another aspect of this invention encompasses an extended format heterodimeric heavy chain in which the X/Y binding pair is coupled with a p/q binding pair in a tandem manner on the heavy chain, as illustrated in FIG. 41D, to effect more efficient assembly of, or confer more stability to, the heterodimeric heavy chains. An exemplary solution to the possible combinations of X/Y, p/q, and m/n pairs to effect arm-specific pairing of two different light chains with the appropriate heavy chain in the extended format bispecific antibody illustrated in FIG. 4D is provided in Table 10.

TABLE 10

| An exemplary illustration of some solutions for arm specific pairing of light chains in an extended format bi-specific mAb of the type where X/Y and m/n pairs are used in tandem on the heavy chain, as illustrated in FIG. 4D. | | | | | |
|---|---|---|---|---|---|
| X | Y | P | q | m | n |
| MHC I α3 domain | β-2 microglobulin | MHC II α2 domain | MHC II β2 domain | TCR Cα | TCR Cβ |
| | | | | TCR Cγ | TCR Cδ |
| | | | | CD3 ε-chain | CD3 γ-chain |
| | | | | CD3 ε chain | CD3 δ-chain |

Following the guidance provided supra for selecting pairing partners for positions within an HBA, the amino acid sequences for the MHC I α3/β2 microglobulin, β2 microglobulin/MHC I α3, MHC II α2/MHC II β2, MHC II β2/MHC II α2, TCR Cα/TCR Cβ, TCR Cβ/TCR Cα, TCR Cγ/TCR Cδ, TCR Cδ/TCR Cγ, CD3 ε-chain/CD3 γ-chain, CD3 γ-chain/CD3 ε-chain, CD3 ε-chain/CD3 δ-chain and CD3 δ-chain/CD3 ε-chain binding pairs for positions X/Y, p/q and/or m/n can be selected, for example, from SEQ ID NO:7/11, 11/7, 15/19, 19/15, 23/27, 27/23, 31/35, 35/31, 39/43 and 43/39, respectively.

Figure 5A:
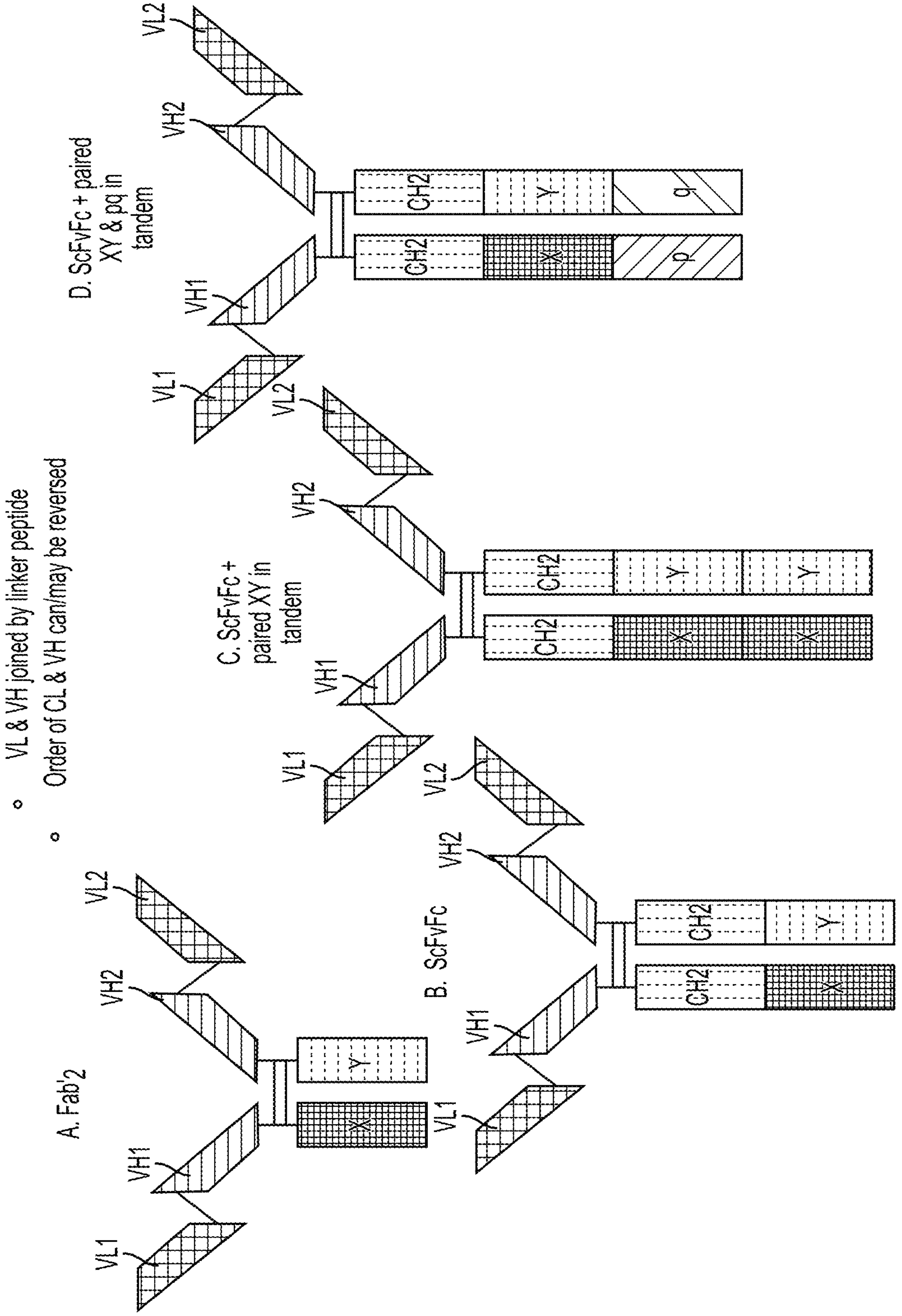
FIG. 5A depicts an alternate solution to arm-specific pairing of light chains, involving heterodimer heavy chain formats as scFv constructs.

An Alternative Solution to the Light Chain Pairing Problem Using scFv Heavy Chain Heterodimers An alternate solution to the problem of light chain pairing is envisioned wherein the two different heavy chains are expressed such that the amino-terminus of the variable region of each heavy chain is covalently linked to the carboxy-terminus of the corresponding light chain to form a single chain Fv (where each Fv recognizes a different antigen, or different epitope on the same antigen), in the context of CH3 domain swapped heterodimer promoting domains. In such HBA's, the one antigen recognizing moiety has a light chain variable region (VL1) fused to a heavy chain variable region (VH1), which is fused to a heterologous polypeptide derived from the IgSF (X). In some HBA's VH1 is fused through a hinge region (H) to X. The other antigen recognizing moiety has a different light chain variable region (VL2) fused to a different heavy chain variable region (VH2), which is fused to the pairing partner for X in the IgSF (Y). In some HBA's, VH2 is fused through H to Y. Some of the HBA's include a CH2 region, through which VH1 is fused to X and VH2 is fused to Y. In some HBA's VH1 is fused to X through H and CH2, and VH2 is fused to Y through H and CH2. Some examples of such formats are illustrated schematically in FIG. 5A. As discussed previously, the X/Y binding pair can be derived from MHC I, MHC II or TCR, for example as shown in Tables 3-10. The m/n pair would not be present in these single chain Fv-like HBA's. Such single chain Fv-like HBA's can also include a heavy chain extension p/q binding pair as discussed previously, which can also be derived from MHC I, MHC II or TCR, for example as shown in Tables 3 and 10.

Some Exemplary Structures of Heterodimer Forming Domains & Design Considerations Structural information can be used to guide the design of CH3 domain swapped heavy chain constructs. The pdb identifiers of some of the reference crystal structures are listed in Table 1. Visual inspection of the respective structures enables demarcation of the respective Ig C-1 pfam set domains in each representative member of the IgSF selected for this purpose. Some ribbon diagrams may be created for this purpose, for example, by using for example Macpymol, Cn3D, or similar structure modeling and/or visualization programs.

In order to maximize proper folding and assembly of the heterodimer forming domains in the context of an Ig heavy chain, i.e. VH1-CH1-H—CH2-X+VH2-CH1-H—CH2-Y where X and Y are, for example, as defined in Table 1, some heterodimeric bispecific antibodies retain the flexible linker separating CH2 and CH3 domains in the Ig heavy chain as a carboxy terminal extension at the end of CH2 domain. Some such heterodimeric bispecific antibodies also retain the analogous flexible loop region separating the selected heterodimer forming domains from the immediately upstream domain in the parent molecule, for fusion to the flexible linker carboxy-terminal to the heavy chain CH2 domain.

For example, some adalimumab hybrid heavy chains in which the adalimumab CH3 domain is replaced with MHC-1 α3 domain, β2 microglobulin, MHC II α2 domain, MHC II β2 domain, TCR Cα domain, TCR Cβ domain, TCR Cγ domain, TCR Cδ domain, CD3 ε-chain ecto-domain, CD3 γ-chain ecto-domain and CD3 δ-chain ecto-domain have the amino acid sequence of SEQ ID NO's: 6 or 58, 10 or 60, 14 or 62, 18 or 64, 22 or 66, 26 or 68, 30 or 70, 34 or 72, 38 or 74, 42 or 76 and 46 or 78, respectively.

Heterodimeric Bispecific Fusion Proteins (HBFP)

Figure 5B:
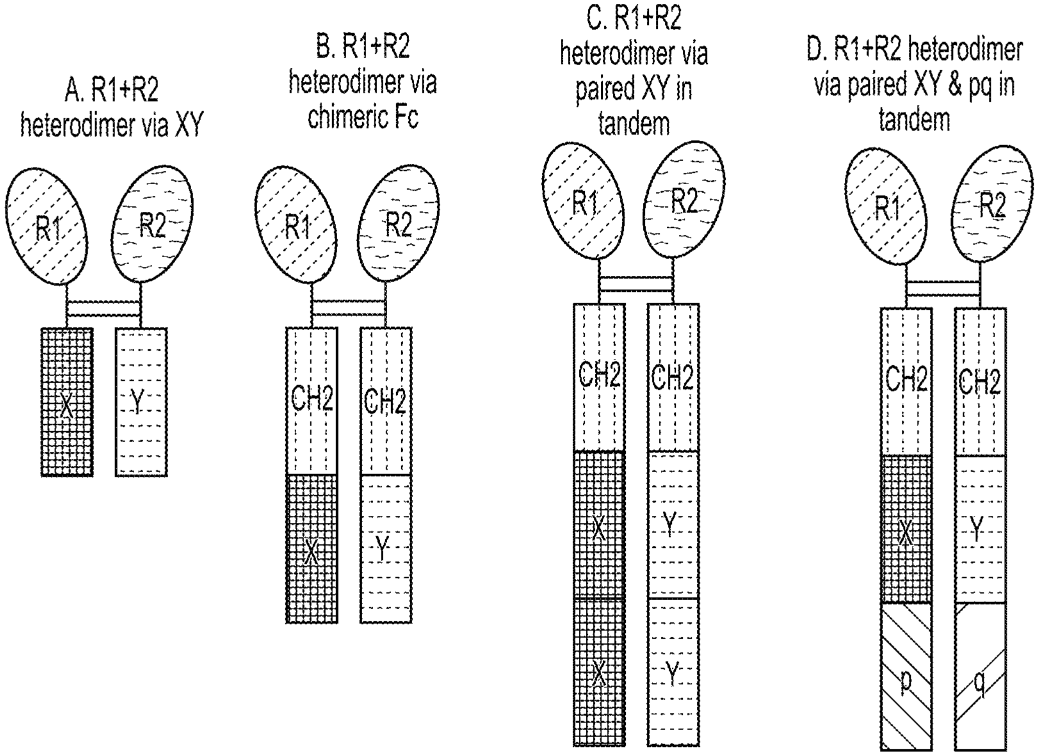
FIG. 5B depicts heterodimer bispecific fusion protein formats enabled via use of paired heterodimer domains from Ig superfamily members listed in Table 1.

The strategies detailed supra can also be applied for expression and manufacturing heterodimeric bispecific fusion proteins (HBFP's), as illustrated in FIG. 5B. Thus, the invention also provides a heterodimeric bispecific fusion protein comprising two distinct moieties. The first moiety (A) comprises a biologically active polypeptide (R1) and the second moiety (B) comprises a different biologically active polypeptide (R2). R1 is fused to X (described supra) and R2 is fused to Y (described supra), optionally through a hinge region (as described above). Some of such fusion proteins include the CH2 heavy chain constant region fused to each of X and Y. Some fusion proteins also involve a tandem heavy chain arrangement as described above, which additionally includes p fused to X and q fused to Y. In some such fusion proteins, p is the same as X and q is the same as Y. In other fusion proteins the p and q pair is different from the X and Y pair.

The bispecific fusion proteins of the invention enjoy a prolonged half-life compared to individual proteins or fusion proteins lacking features endowed by the Fc region of antibodies R1 and R2 can be any of a number of therapeutic proteins, including ligand binding extracellular domains of cell surface receptors for disease exacerbating ligands or enzymes. A list of commercially approved FDA Fc-fusion proteins, and Fc fusion proteins in clinical development is provided in Tables 11 and 12, respectively.

TABLE 11

FDA approved Fc-Fusion protein therapeutics (all are formatted as human IgG1 Fc fusion proteins).

| Product | Source molecule/ receptor | Ligand, and Indication |
|---|---|---|
| Elocate | FVIII | Blood clotting factor, Hemophilia A |
| Alprolix | FIX | Blood clotting factor, Hemophila B |
| Amevive, (alefacept) | LFA3 | Binds CD2; inhibits T-cell proliferation, psoriasis & transplant rejection. |
| Enbrel ®, (etanercept) | TNFR2 | Binds to soluble and membrane TNF, thus reducing cytokine-induced inflammation in RA, plaque, psoriasis, psoriatic arthritis |
| Orencia ®, (abatacept) | Mutated CTLA4 | Binds CD80, CD86; inhibits T-cell costimulation in RA |
| Nulojix ®, (belatocept) | CTLA4 | Binds CD80, CD86; inhibits T-cell costimulation in translplant rejection. |
| Eylea ® (aflibercept); Zaltrap ® (zivaflibercept) | VEGFR1/ VEGFR2 | Binds VEGF-A, VEGF-B, and placental growth factor, preventing neovascularization in wet age-related macular degeneration and macular edema (Eylea) as well as in colorectal cancer (Zaltrap). |

TABLE 11-continued

| Product | Source molecule/ receptor | Ligand, and Indication |
| --- | --- | --- |
| Arcalyst ® (rilonacept) IL-1 Trap | IL1R AcP and IL1R sequentially fused to IgG1 Fc | Binds IL-1 with high affinity, neutralizing IL-1 in CAPS (cryopyrin associated periodic syndrome). |

FDA approved Fc-Fusion protein therapeutics (all are formatted as human IgG1 Fc fusion proteins).

TABLE 12

Fc fusion protein in clinical development, all as human IgG1 isotype.

| Product | Source molecule/ receptor | Ligand and proposed indication |
| --- | --- | --- |
| Blisbimod (a-623, AMG623) | BAFF | Binds to BAFF and inhibits receptor interaction, decreasing B-cell survival in SLE and RA. |
| Dulaglutide (LY2189265) | GLP1 peptide analog | Mimics effects of GLP1 on insulin resistance and VLDL production. |
| APG101 apocept | CD95 ectodomain. | Blocks the CD95 ligand (CD95L, FasL, Apo-1L) from binding to CD95, reducing cancer cell migration in malignant glioma and preventing early cell death in myelodysplastic syndrome |
| IL-6 trap | IL-6R ectodomain co-expressed with gp130, both as independent Fc fusions | Binds IL-6, preventing IL-6 dependent cell proliferation |

Nucleic Acids

The invention further provides nucleic acids encoding any of the heavy and light chains described above, for example, X, Y, p, q, m and n. Included are polynucleotides having one or more nucleic acids that encode the heavy chain and light chain of antigen recognizing moiety A, for example, a hybrid derived from adalimumab or any antibody with therapeutic potential such as an therapeutic antibody disclosed infra, the light chain of antigen recognizing moiety B and the heavy chain of antigen recognizing moiety B, for example a hybrid derived from a second antibody with therapeutic potential such as an antibody disclosed infra. Some polynucleotides encode one or more of the antigen recognizing moieties of the Fv-like HBA's or the HBFP's discussed above.

One can readily combine the nucleic acid sequences of the applicable segments of known or new therapeutic antibodies with nucleic acid sequences encoding the IgSF pairing partners of choice. Following the guidance provided supra for selecting pairing partners for positions within an HBA, nucleic acid sequences encoding the MHC I α3/β2 microglobulin, β2 microglobulin/MHC I α3, MHC II α2/MHC II β2, MHC II β2/MHC II α2, TCR Cα/TCR C3, TCR CP/TCR Cα, TCR Cγ/TCR Cδ, TCR Cδ/TCR Cγ, CD3 ε-chain/CD3 γ-chain, CD3 γ-chain/CD3 ε-chain, CD3 ε-chain/CD3 δ-chain and CD3 δ-chain/CD3 ε-chain binding pairs for positions X/Y, p/q and/or m/n can be selected, for example, from SEQ ID NO:7/11, 11/7, 79/80, 80/79, 15/19, 19/15, 81/82, 82/81, 23/27, 27/23, 83/84, 84/83, 31/35, 35/31, 85/86, 86/85, 39/43, 87/88, 88/87, and 43/39, 87/89, 89/87, respectively.

For example, some adalimumab hybrid heavy chains in which the adalimumab CH3 domain is replaced with MHC-1 α3 domain, β2 microglobulin, MHC II α2 domain, MHC II β2 domain, TCR Cα domain, TCR CP domain, TCR Cγ domain, TCR Cδ domain, CD3 ε-chain ecto-domain, CD3 γ-chain ecto-domain and CD3 δ-chain ecto-domain are encoded by the nucleic acid sequences of SEQ ID NO's: 5 or 57, 9 or 59, 13 or 61, 17 or 63, 21 or 65, 25 or 67, 29 or 69, 33 or 71, 37 or 73, 41 or 75 and 45 or 77, respectively.

Therapeutic Heterodimeric Bispecific Antibodies

HBA's incorporating the heavy chain modifications described above can be made to any target molecule. The HBA's are particularly useful for surface-bound or circulating target proteins (e.g., on cells or viruses) in which aggregation or neutralization of the target protein induces a desired response. The desired response can be, for example, clearing of a target protein, reducing aggregation of a target protein, clearing of a cell or virus bearing a target, signal transduction through a receptor, e.g., inducing apoptosis or cytostasis, inhibiting a receptor binding to a ligand or counterreceptor, or internalization of an HBA conjugated to a toxic agent. HBA's can be made to the same targets as existing therapeutic antibodies or fusion proteins or can be derivatized versions of therapeutic antibodies or fusion proteins in which one or more of the existing constant regions have been replaced by the heterologous polypeptides of the present invention.

Thus, the teachings herein can be applied to create novel HBA's using mono-specific antibodies having properties of interest, such as, for example, antibodies with established therapeutic efficacy. For example, the variable regions of A or B or both can be derived from abagoavomab, abciximab, abituzumab, abrilumab, actoxumab, adalimumab, adecatumumab, aducanumab, afasevikumab, afelimomab, afutuzumab, alacixumab pegol, alemtuzumab, alirocumab, altumomab pentetate, amatuximab, anatumomab mafeatox, anetumab ravtansine, anifrolumab, anrukinzumab, apolizumab, arcitumomab, ascrinvacumab, aselizumab, atezolizumab, atinumab, atizumab, atorolimumab, avelumab, bapeineuzumab, natalizumab, basiliximab, bavituximab, bectumomab, begelomab, belimumab, benralizumab, bertilimumab, besilesomab, bevacizumab, bezlotoxumab, biciromab, bimagrumab, bimekizumab, bivatuzumab mertansine, bleselumab, blinatumomab, blontuvetmab, blosozumab, bococizumab, brazikumab, brentuximab vedotin, briakinumab, brodalumab, brolucizumab, brontictuzumab, burosumab, cabiralizumab, canakinumab, cantuzumab metansine, cantuzumab ravtansine, caplacizumab, capromab pendetide, carlumab, carotuximab, cedelizumab, cergutuzumab amunaeleukin, certolizumab pegol, cetuximab, cituximab bogatox, cixutumumab, clazakizumab, clenoliximab, clivatuzumab tetraxetan, codrituzumab, coltuximab ravtansine, conatumumabe, concizumab, crenezumab, coredumab, dacetuzumab, daclizumab, dalotuzumab, dapirolizumab pegol, daratumumab, dectrekumab, demcizumab, denosumab, depatuxizumab, derlotuximab, detumomab, dinutuxidmab, diridavumab, domogrozumab, dorimomab, drozitumab, duligotumab, dupilumab, durvalumab, dusigitumab, ecromeximab, eculizumab, edobabcomab, edrecolomab, efalizumab, efungumab, eldelumab, elgemtumab, elotuzumab, elsilimomab, emactuzumab, emibetuzumab, emicizumab, enavatuzumab, enlimomab, enoblituzumab, enokizumab, enoticumab, ensituximab, eptitumomab, epratuzumab, erenumab, erlizumab, ertumaxomab, etaracizumab, etrolizumab, evinacumab, evolocumab, exbivirumab, fanolesomab, farlimomab, farletuzumab, fasinumab, felvizumab, fezakinumab, figitumumab, firivumab, flanvotumab, fletikumab, fontolizumab, foralumab, foravirumab, fresolimumab, fluranumab, futuximab, glacanezumab, galiximab, ganitumab, gantenerumab, gavilimomab, gemtuzumab, gevokizumab, girentuximab, glembatumumab, golimumab, gomiliximab, guselkumab, ibalizumab, ibritumomab, icrucumab, idarucizumab, igovomab, imalumab, imciromab, imgatuzumab, inclacumab, indatuximab, indusatumab, inebilizumab, infliximab, intetumumab, inolimomab, inotuzumoab, ipilimumab, iratmumab, isatuximab, itolizumab, ixekizumab, keliximab, labetuzumab, lampalizumab, landelumab, landogrozumab, laprituximab, lebrikizumab, lemalesomab, lendalizumab, lenzilumab, lerdelimumab, lexatumumab, libivirumab, lifastuzumab, ligelizumab, lilotomab, lintuzumab, lirilumab, lodelcizumab, likivetmab, lorvotuzumab, lucatumumab, lulizumab, lumiliximab, lumretuzumab, mapatumumab, margetuximab, maslimomab, mavrilimumab, matuzumab, mepolizumab, metelimumab, milatuzumab, minretumomab, mirvetuximab, mitumomab, mogamulizumab, monalizaumab, morolimumab, motavizumab, moxetumomab, muromonab, nacolomab, namilumab, naptumomab, natatuximab, narnatumab, natlizumab, navicixizumab, navivumab, nebacumab, necitumumab, nemolizumab, nerelimomab, nesvacumab, nimotuzumab, nivolumab, nofetumomab, obiltoxaximab, obinutuzumab, ocaratuzumab, ocrelizumab, odulimomab, ofatumumab, olaratumab, olokizumab, oalizumab, onartuzumab, ontuxizumab, opicinumab, opotruzumab, oregovomab, orticumab, otelixizumab, otlertuzumab, oxelumab, ozanezumab, ozoralizumab, pagibximab, palivizumab, pamrevlumab, pankomab, panobacumab, parsatuzumab, pascolizumab, pateclizumab, patritumab, pembrolizumab, pemtumomab, perakizumab, pertuzumab, pexelizumab, pidilizumab, pinatuzumab, pintumomab, placulumab, plozalizumab, polatuzumab, ponezumab, prezalizumab, priliximab, pritoxaximab, pritumumab, quilizumab, racotumomab, radretumab, rafivirumab, ralpancizumab, ramucirumab, ranibizumab, ranibizumab, raxibacumab, refanezumab, regavirumab, reslizumab, rilotmumab, rinucumab, risankizumab, rituximab, rivabazumab, robatumumab, roledumab, romosozumab, rontalizumab, rovalpituzumab, rovelizumab, ruplizumab, sacituzumab, samalizumab, sapelizumab, sarilumab, satumomab, secukinumab, seribantumab, setoxaximab, sevirumab, sibrotuzumab, sifalimumab, siltuximab, simtuzumab, siplizumab, sirukumab, sofituzumab, solanezumab, solitomab, sonepcizumab, sontuzumab, stamulumab, sulesomab, suvizumab, tabalumab, tacatuzumab, tadocizumab, talizumab, tamtuetmab, tanezumab, tefibazumab, telimomab, tenatumomab, teneliximab, teplizumab, teprotumumab, tesidolumab, tetlomab, tezepelumab, ticilimumab, tildrakizumab, tigatuzumab, timolumab, tisotumab, tocilizumab, tosatoxumab, tositumomab, tovetumab, tralokinumab, trastuzumab, tregalizumab, tremelimumab, trevogrumab, tocutuzumab, tuvirumab, ulituximab, ulocuplumab, urelumab, urtoxazumab, ustekinumab, utomilumab, vadastuximab, vandortuzumab, vantictumab, vanucizumab, vapaliximab, varlillumab, vatelizumab, vedolizumab, veltuzumab, vepalimomab, vesencumab, visilizumab, vobarilizumab, volociximab, vorsetuzumab, votumumab, xentuzumab, zalutumumab, zanolimumab, zatuximab, ziralimumab and zolimomab. HBA's derived from combinations of the above referenced mono-specific antibodies may be used to achieve synergistic effects across various disease indications.

Therapeutic Heterodimeric Bispecific Fusion Proteins (HBFP's)

HBFP's incorporating the heavy chain modifications described above can be made to any target molecule. The HBFP's are particularly useful for surface-bound or circulating target proteins (e.g., on cells or viruses) in which aggregation or neutralization of the target protein induces a desired response. The desired response can be, for example, clearing of a target protein, reducing aggregation of a target protein, clearing of a cell or virus bearing a target, signal transduction through a receptor, e.g., inducing apoptosis or cystostasis, inhibiting a receptor binding to a ligand or counterreceptor, or internalization of an HBFP conjugated to a toxic agent. HBFP's can be made to the same targets as existing therapeutic fusion proteins or can be derivatized versions of therapeutic Fc fusion proteins in which one or more of the existing constant regions have been replaced by the heterologous polypeptides of the present invention.

Thus, the teachings herein can be applied to create novel HBFP's using therapeutically relevant biologic molecules having properties of interest, such as, for example, receptors, enzymes, or enzyme inhibitors (e.g. serpins) with established therapeutic efficacy. For example, the biologically active regions of R1 or R2 or both can be derived from Elocate, Alprolix, Amevive (alefacept), Enbrel® (etanercept), Orencia® (abatacept), Nulojix® (belatocept), Eylea® (aflibercept), Zaltrap® (zivaflibercept), Arcalyst® (rilonacept), IL-1 Trap, Blisbimod (a-623, AMG623), Dulaglutide (LY2189265), APG101, apocept, IL-6 trap, or C1-esterase inhibitor.

Genetic Engineering and Expression

HBA's or HBFP's having the modifications described above can be produced by recombinant expression. Production of an antibody or fusion protein typically requires several expression units. For example, in the case of HBA's, one for each for the different heavy chains, and one or two for the two light chains depending whether the light chains are the same or different. The expression units can be present on separate vectors, or split among two or more vectors, or all can be present on the same vector. Production of an Fc fusion protein typically requires two expression units, one for each heavy chain. The expression units can be on the same or different vectors. For example, one heavy chain expression vector expresses one arm of the HBA or HBFP and the other heavy chain expression vector expresses the other arm of the HBA or HBFP. Typically such constructs are fused at their N-termini to a signal sequence. The modified constant regions of the HBA's or HBFP's can be introduced by methods such as site specific or cassette mutagenesis, or introduced in de novo nucleic acid synthesis. The light chain expression units typically include from N-terminus to C-terminus a signal peptide, a variable region and a light chain constant region (or the substituted heterologous polypeptide), as for standard expression of an antibody.

The order in which fusions of genetic elements is performed in building a construct encoding several components is not important. The segments can also be linked simultaneously by joining overlapping oligonucleotides encoding the respective segments in an overlapping PCR-type reaction, or by the methodology of Gibson (Gibson 2011;

Merryman and Gibson 2012). In practice, once expression units encoding the heavy chain constant regions of the invention have been produced, the same expression units can be used to insert any heavy chain variable region(s) or other binding region(s) in the case of a fusion protein (and sometimes a light chain variable region) without recreating the DNA segment encoding all of the heavy chain components.

Mammalian cells are a preferred host for expressing nucleotide segments encoding HBA's or HBFP's of the invention (see Winnacker, From Genes to Clones, (VCH Publishers, NY, 1987)). A number of suiTable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Preferably, an HBA or HBFP of the invention is expressed from a monoclonal cell line.

Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Cells are transfected with one or more vectors encoding the HBA or HBFP to be expressed. For a multi-chain antibody, the heavy and light chains can be expressed on the same or separate vectors. For expression of multi-subunit complexes, the DNA encoding the components of the complexes (i.e., different antibodies or fusion proteins) can be on the same or different vectors.

HBA's or HBFP's can be made by culturing host cells, such as the cells discussed above, under conditions so as to express the nucleic acid(s) encoding the HBA or HBFP, and recovering the antibody or fusion protein. In some methods, one or more HBA or HBFP chains are separately isolated and assembled, outside of the cell, for example, in the supernatant or in vitro. In some methods, HBA or HBFP chains are expressed, processed to remove signal peptides, assembled and secreted from host cells. It is believed that association of different heavy chains, association between heavy and light chains occur at least predominantly within cells so that HBA's are secreted in a fully associated state.

HBA's or HBFP's can be purified from cell culture supernatants by conventional antibody purification methods. The purification can include a chromatography step using protein A or protein G as the affinity reagent, provided that the requisite protein A or protein G binding sites are retained in the heterologous heavy chain. In addition, affinity chromatography directed towards the X/Y, or p/q, or m/n, or any combination of the above binding pairs, could be employed sequential to, or instead of protein-A or protein-G chromatography, to effect product purity during manufacture of HBA or HBFP described supra. Conventional antibody or protein purification procedures, such as ion exchange, hydroxyapatite chromatograph or HPLC can also be used (see generally, Scopes, Protein Purification (Springer-Verlag, NY, 1982)).

Conjugated Antibodies or Fusion Proteins

The HBA's or HBFP's can include conjugated therapeutic moieties that can be used to treat, combat, ameliorate, prevent or improve an unwanted condition or disease in a patient. For example, HBA's or HBFP's can be conjugated to a toxic agent. Toxic agents can be cytotoxic or cystostatic. Some example of toxic agents include antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, camptothecins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, *vinca* alkaloids, or the like. A variety of radionuclides are available for the production of radioconjugated antibodies. Examples include $^{212}$Bi, $^{131}$I, $^{131}$In, $^{90}$Y, and $^{186}$Re. Conjugates of an antibody and toxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). A toxic agent can also be linked to an antibody via a linker, which may be cleavable under intracellular conditions (US 2003-0083263, 2005-0238649 and 2005-0009751). Many of the above toxic agents are only effective or most effective when internalized within a cell. The HBA's of the invention can be internalized by binding to cellular receptors, for example, crosslinking of cellular receptors can promote internalization. The HBA's can also be coupled to one or more other antibodies or to a detecTable label.

Therapeutic Applications

The HBA's or HBFP's disclosed herein can be used for treating or effecting prophylaxis of a disease in a patient having or at risk for the disease targeted by any of the mono-specific antibodies or fusion proteins disclosed herein. For example, the HBA's or HBFP's can be used to treat or effect prophylaxis of a patient having or at risk for having cancer, an autoimmune or inflammatory condition, a neurodegenerative disease, an infectious disease, osteoporosis, dyslipidemia, macular degeneration, a blood coagulation disorder, a cardiovascular disease or disorder, an organ transplant, diabetes, influenza, a muscle wasting disorder or a gastrointestinal disease or disorder by administering the HBA or HBFP in a therapeutically effective regime.

The HBA's or HBFP's of the invention can be used for treating cancers including those for which commercial antibodies or fusion proteins mentioned above have been used. The methods can be used to treat one or more hematological malignancies, such as leukemia (e.g., T cell large granular lymphocyte leukemia), lymphoma (Hodgkin's or Non-Hodgkin's), or multiple myeloma. Some HBA's or HBFP's are suiTable for treating solid tumors such as, for example, skin cancer (e.g., melanoma), ovarian, endometrial, bladder, breast, rectum, colon, gastric, pancreatic, lung, thymus, kidney and brain. Some HBA's or HBFP's can be used to treat prostate cancer, breast cancer, colorectal cancer, non-small cell lung carcinoma, gastrointestinal cancer, metastatic cancer, squamous cell carcinoma, head and neck cancer, solid tumors, glioblastoma, neuroblastoma, testicular cancer, adrenocortical carcinoma or pancreatic cancer. Other hematological cancers suiTable for treatment with some HBA's of the invention include acute myelogenous leukemia and chronic lymphocytic leukemia.

The HBA's or HBFP's of the invention can also be used for suppressing various undesirable immune responses including those in which the therapeutic antibodies mentioned above have been used.

One category of immune disorders treaTable by some HBA's or HBFP's of the invention is transplant rejection. When allogeneic cells or organs (e.g., skin, kidney, liver, heart, lung, pancreas and bone marrow) are transplanted into a recipient (i.e., the donor and recipient are different individuals from the same species), the recipient's host immune system is likely to mount an immune response to foreign antigens in the transplant (host-versus-graft disease) leading to destruction of the transplanted tissue. The HBA's or HBFP's of the present invention are useful, inter alia, to block alloantigen-induced immune responses in the recipient.

A related use for HBA's or HBFP's of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants.

A further situation in which immune suppression is desirable is in treatment of autoimmune or inflammatory diseases such as Crohn's disease, ulcerative colitis, inflammatory bowel disease, multiple sclerosis, stiff man syndrome, rheumatoid arthritis, myasthenia gravis, Type I diabetes, Graves' disease, myasthenia gravis, Sjogren's syndrome and lupus erythematosus. In these diseases, the body develops a cellular and/or humoral immune response against one of its own antigens leading to destruction of that antigen, and potentially crippling and/or fatal consequences. Autoimmune diseases are treated by administering the applicable HBA's or HBFP's of the invention.

Other immune disorders treaTable by the HBA's or HBFP's of the invention include asthma, allergies, celiac disease, plaque psoriasis, psoriatic arthritis, ankylosing spondylitis, juvenile idiopathic arthritis and uveitis. Celiac disease, psoriasis and uveitis are autoimmune diseases.

Some HBA's or HBFP's are useful for the treatment of neurodegenerative diseases such as Alzheimer's disease, Parkinson's disease, corticobasal degeneration, frontotemporal lobar degeneration, Lewy body disease, Pick's disease, progressive supranuclear palsy, multiple system atrophy and ALS.

The HBA's or HBFP's can also be used for treatment of pathogenic infections, such as viral, bacterial, protozoan or fungal infection. Some example of viral infections include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus. Some examples of bacterial infections include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, Lymes disease bacteria, streptococci, or *neisseria*. Some examples of pathogenic fungi include *Candida, Aspergillus, Cryptococcus, Histoplasma, Pneumocystis* and Stachybotrys. Examples of protozoa include *Cryptosporidium, Giardia lamblia* and *plasmodium*.

The specific disease targeted will depend on the individual properties of the antibody selected for conversion into an HBA. Pharmaceutical compositions comprising the HBA's or HBFP's of the invention would be administered to the patient in a regime (dose, frequency and route of administration) effective to reduce the risk, lessen the severity or delay the onset and/or progression of at least one sign or symptom of the disease.

HBA's or HBFP's are administered in an effective regime, meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an HBA or HBFP are 0.01-20, or 0.5-5, or 0.01-1, or 0.01-0.5 or 0.05-0.5 mg/kg body weight (e.g., 0.1, 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the HBA or HBFP in the circulation, the duration of effect, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Other Applications

The HBA's can be used for detecting their target molecule in the context of clinical diagnosis or treatment or in research. For example, the HBA's can be used to detect a cancer-related antigen as an indication a patient is suffering from an immune mediated disorder amenable to treatment. The HBA's can also be sold as research reagents for laboratory research in detecting targets and their response to various stimuli. In such uses, HBA's can be labeled with fluorescent molecules, spin-labeled molecules, enzymes or radioisotopes, and can be provided in the form of kit with all the necessary reagents to perform the assay. The HBA's can also be used to purify their target antigens e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. VH and VL Domains Selected from Adalimumab

The VH and VL domains from adalimumab[1] are selected as the antigen specificity determinants for a construct, as it is a well characterized antibody of known crystal structure (pdb id 3WD5). A discrepancy in sequence of adalimumab VH at residue 82 is noted between the pdb entry and the drugbank.ca web site, with pdb indicating D82, and the drugbank entry indicating Q82. Structural inspection of 3WD5 revealed residue 82 is framework 3, and likely to be of minimal consequence for antigen recognition, Q82 was retained for testing in the prototype construct. Sequence analysis of adalimumab V regions revealed VH is closest to human sub-group 3, and VL is closest to human kappa chains sub-group 1 (Kabat et al. 1991). Leader peptides for adalimumab V-regions were selected from a human anti-HIV-1 gp41 antibody designated 3D6 as its V region sequences belonged to the same subgroup as adalimumab (Felgenhauer et al. 1990; Kabat et al. 1991). The amino-acid sequences of L and V regions of adalimumab are reverse translated and codon optimized for human codon usage[2], and fused to human Cκ and Cγ1 encoding sequence. The full sequences of Adalimumab light chain and heavy chain protein and DNA sequences are provided in FIGS. 6 and 7, respectively.

Example 2. MHC-1 α3 Domain Paired with β2 Microglobulin Replacing CH3 Domain in Heavy Chains In order to effect heterodimer formation between two heavy chains, the CH3 domains are replaced with MHC-1 α3 domain or β2 microglobulin domain, taking into consideration structural information regarding flexible loops separating distinct domains. The DNA and predicted protein sequences for these MHC-1 α3 domain from HLA-A (A*68 allele) or β2 microglobulin hybrid adalimumab heavy chains are provided in FIGS. 8A, B and 9A, B, respectively. The DNA and protein sequences of MHC I α3 domain from HLA-A (A*68 allele) and β2 microglobulin in isolation, for use in any X/Y, m/n or p/q combination described in FIGS. 3A-D, 4A-D, & 5A-B are provided in FIGS. 8C, D and 9C, D respectively.

Example 3 MHC II α2 Domain Paired with MHC II β2 Domain

The CH3 domains are replaced with MHC-II α2 domain or MHC II β2 domain, taking into consideration structural information regarding flexible loops separating distinct domains. The DNA and predicted protein sequences for these MHC-II α2 domain (derived from HLA-DR alpha) or MHC II β2 domain (derived from HLA-DR beta1) hybrid adalimumab heavy chains are provided in FIGS. 10A, B and 11A, B respectively. The DNA and protein sequences of MHC II α2 domain (derived from HLA-DR alpha) and MHC II β2 domain (derived from HLA-DR beta1) in isolation, for use in any X/Y, m/n, or p/q combination as envisioned in FIGS. 3A-D, 4A-D, & 5A-B are provided in FIGS. 10C, D and 11C, D respectively.

Example 4. T-Cell Antigen Receptor Ca Paired with T-Cell Antigen Receptor Cβ Domains The CH3 domains are replaced with T-cell antigen receptor (TCR) Cα domain or TCR Cβ domain, taking into consideration structural information regarding flexible loops separating distinct domains. The DNA and predicted protein sequences for these TCR Cα domain or TCR Cβ domain hybrid adalimumab heavy chains are provided in FIGS. 12A, B and 13A, B respectively. The DNA and protein sequences of TCR Cα domain and TCR Cβ domain in isolation, for use in any X/Y, m/n, or p/q combination as envisioned in FIGS. 3A-D, 4A-D, & 5A-B are provided in FIGS. 12C, D and 13C, D respectively.

Example 5. T-Cell Antigen Receptor Cγ Paired with T-Cell Antigen Receptor Cδ Domains The CH3 domains are replaced with T-cell antigen receptor (TCR) Cγ domain or TCR Cδ domain, taking into consideration structural information regarding flexible loops separating distinct domains. The DNA and predicted protein sequences for these TCR Cγ domain or TCR Cδ domain hybrid adalimumab heavy chains are provided in FIGS. 14A, B and 15A, B respectively. The DNA and protein sequences of TCR Cγ domain and TCR Cδ domain in isolation, for use in any X/Y, m/n, or p/q combination as envisioned in FIGS. 3A-D, 4A-D, & 5A-B are provided in FIGS. 14C, D and 15C, D respectively.

Example 6. Ecto-Domains of CD3 ε, δ and ε, γ as Paired Heterodimer Chains in Place of CH3

Figure 3:
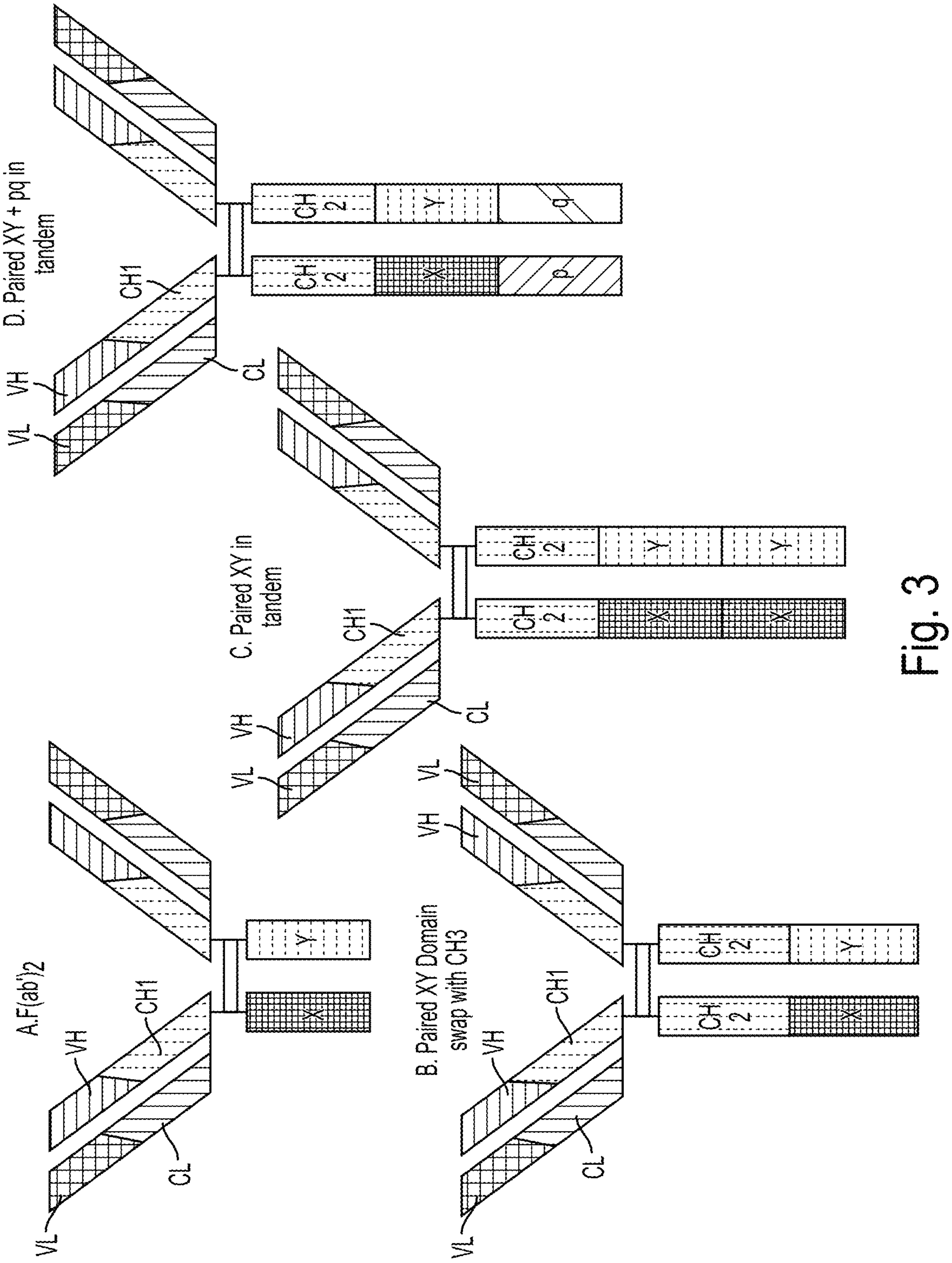
FIGS. 3A-D show a schematic depiction of various bi-specific antibody formats with heterodimer heavy chains assembled by replacement of CH3 domain with domains from pairs of molecules listed in Table 1.
Figure 4:
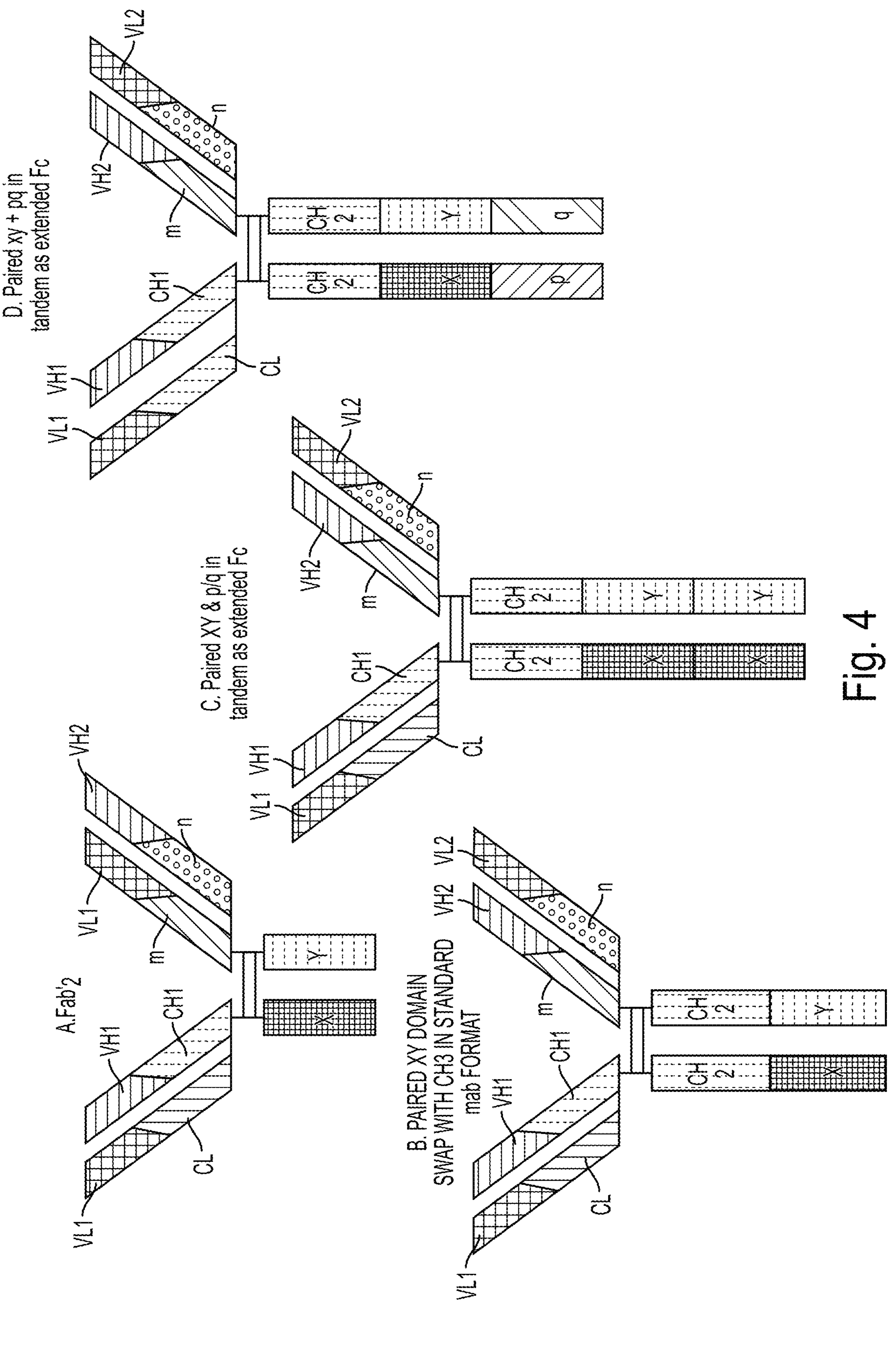
FIGS. 4A-D depicts arm specific pairing of light chain with heterodimer heavy chains in bi-specific antibody formats as detailed in Tables 3-8.

The CD3 ε-chain ectodomain pairs with CD3 γ-chain as well as with CD3 δ-chain ectodomain (Arnett et al. 2004; Kjer-Nielsen et al. 2004). The CD3 γ, δ, and ε-chain ectodomains are Ig SF members and their Ig fold is of pfam id I-set (Table 1), in contrast with CH3 (pfam id C-set). The potential for promoting heterodimer formation in Ig heavy chains as CH3 domain swaps with CD3 γ, δ, & ε-chain ectodomains is tested. The CH3 domains are replaced with CD3 ε, γ, or δ-ectodomain, taking into consideration structural information regarding flexible loops separating distinct domains. The DNA and predicted protein sequences for these CD3 ε-ectodomain, γ-ectodomain, or δ-ectodomain hybrid adalimumab heavy chains are provided in FIGS. 16A, B, 17A, B and 18A, B respectively. The DNA and protein sequences of CD3 ε-ectodomain, γ-ectodomain, or δ-ectodomain in isolation, for use in any X/Y, m/n, or p/q combination as envisioned in FIGS. 3, 4, & 5 are provided in FIGS. 16C, D, 17C, D and 18C, D respectively.

Example 7. Proof of Concept Construction and Expression of Heavy Chains Comprised of Paired Sets of Heterodimers as Described in Examples 1-5

Recombinant synthetic DNAs were purchased from Blue Heron as clones in pUC19. These clones provided the cassettes encoding the domains listed in examples 1-6 for making bi-functional antibody constructs. The clones are listed in Table 13. All synthetic clones and constructs derived from the clones were sequence verified prior to their use in subsequent steps throughout the course of this work.

TABLE 13

List of synthetic DNAs as pUC19 clones used for assembly of positive control antibody, and bi-functional heavy chain constructs.

| Clone name | Description | Notes |
|---|---|---|
| GSB001 | Adalimumab L-VL-Cκ | Sequence as in FIG. 6 |
| GSB002 | Adalimumab L-VH-Cγ1 | CH1-H-CH2-CH3 domains of human Cg1, sequence as in FIG. 7 |
| GSB003 | Adlimumab L-VH-CH1-H-CH2x | CH1-H-CH2x domains of human Cg1, sequence as in FIG. 7 |
| GSB004 | MHC I α3 domain | Sequence as in FIG. 8 C |
| GSB005 | β2 microglobulin | Sequence as in FIG. 9 C |
| GSB006 | MHC II α2 domain | Sequence as in FIG. 10 C |
| GSB007 | MHC II β2 domain | Sequence as in FIG. 11 C |
| GSB008 | TCR Cα domain | Sequence as in FIG. 12 C |
| GSB009 | TCR Cβ domain | Sequence as in FIG. 13 C |
| GSB010 | TCR Cγ domain | Sequence as in FIG. 14 C |
| GSB011 | TCR Cδ domain | Sequence as in FIG. 15 C |
| GSB014 | CD3 ε ecto-domain | Sequence as in FIG. 16 C |
| GSB012 | CD3 γ ecto-domain | Sequence as in FIG. 17 C |
| GSB013 | CD3 δ ecto-domain | Sequence as in FIG. 18 C |

Forward and reverse pcr primers used for assembling and cloning the bi-functional antibody expression constructs into target mammalian expression vector pcDNA3.1-are listed in Table 14.

TABLE 14

List of PCR primers. F indicates forward orientation, R indicates reverse orientation. The underlined sequence denotes the restriction site in the non-complentary tail incorporated to facilitate cloning in the mammalian expression vector of choice (pcDNA3.1-).

| Primer name | Size (nts) | SEQ ID NO | Target template (Table 2) | Orientation (restriction site) | Sequence (non-complementary restriction site underlined) |
|---|---|---|---|---|---|
| gb001 | 49 | 90 | GSB001 (Adalimumab L-VL-CK) | F (Not I) | TAGACTCGAGCGGCCGCACCATGGACATGAGG GTCCCCGCTCAGCTCCT |
| gb002 | 46 | 91 | GSB001 (Adalimumab L-VL-CK) | R (Eco RI) | TGGTGGAATTCTCATTACTAGCACTCGCCGCG GTTGAAGGACTTGG |
| gb003 | 48 | 92 | GSB002 (Adalimumab L-VH-Cγ1) | F (Not I) | TAGACTCGAGCGGCCGCACCATGGAGTTGGGA CTGAGCTGGATTTTCC |
| gb004 | 48 | 93 | GSB002 Adalimumab L-VH-Cγ1) | R (Kpn I) | ACTTAAGCTTGGTACCTCATTTACCCGGAGAC AGGGAGAGGCTCTTCT |

TABLE 14-continued

List of PCR primers. F indicates forward orientation, R indicates reverse orientation. The underlined sequence denotes the restriction site in the non-complentary tail incorporated to facilitate cloning in the mammalian expression vector of choice (pcDNA3.1-).

| Primer name | Size (nts) | SEQ ID NO | Target templatetion (Table 2) | Orientation (restric-etion site) | Sequence (non-complementary restriction site underlined) |
|---|---|---|---|---|---|
| gb004a | 24 | 94 | GSB003 (Adlimumab L-VH-CH1-H-CH2x) | R | TGGTTCTCGGGGCTGCCCTTTGGC |
| gb005 | 30 | 95 | G5B004-GSB014 | F | ATCGAGAAAACCATCTCCAAAGCCAAAGGG |
| gb006 | 42 | 96 | G5B004 (MHC I α3 domain) | R (Kpn I) | ACTTAAGCTTGGTACCTCACCATCTCAGGGTG AGGGGCTTGG |
| gb007 | 47 | 97 | G5B005 (β2 microglobulin) | R (Kpn I) | ACTTAAGCTTGGTACCTTACATGTCTCGATCC CACTTAACTATCTTG |
| gb008 | 50 | 98 | G5B006 (MHC II α2 domain) | R (Kpn I) | ACTTAAGCTTGGTACCTTAGTTCTCTGTAGTC TCTGGGAGAGGGCTTGGA |
| gb009 | 50 | 99 | GSB007 (MHC II β2 domain) | R (Kpn I) | ACTTAAGCTTGGTACCTCAACTCAGCATCTTG CTCTGTGCAGATTCAGAC |
| gb010 | 47 | 100 | GSB008 (TCR Cα domain) | R (Kpn I) | ACTTAAGCTTGGTACCTCACGTATCTGTTTCA AAGCTTTTCTCGACC |
| gb011 | 50 | 101 | GSB009 (TCR Cβ domain) | R (Kpn I) | ACTTAAGCTTGGTACCCTAGTCTGCTCTACCC CAGGCCTCGGCGCTGACGAT |
| gb012 | 50 | 102 | GSB010 (TCR Cγ domain) | R (Kpn I) | ACTTAAGCTTGGTACCTTAGTTTGTGAGCTGC AGCAGTAGTGTATCATTTG |
| gb013 | 50 | 103 | GSB011 (TCR Cδ domain) | R (Kpn I) | ACTTAAGCTTGGTACCTTACATGTTCACCTTC TCGGTATGAACTATGGCTTTG |
| gb014 | 46 | 104 | GSB014 (CD3 ε ecto-domain) | R (Kpn I) | ACTTAAGCTTGGTACCTCAATCCATCTCCATG CAGTTCTCACACAC |
| gb015 | 56 | 105 | GSB012 (CD3 γ ecto-domain) | R (Kpn I) | ACTTAAGCTTGGTACCTCAAGATATGGTGGC TGCATTTAGTTCAATGCAGTTCTGA |
| gb016 | 47 | 106 | GSB013 (CD3 δ ecto-domain) | R (Kpn I) | ACTTAAGCTTGGTACCTCAATCCAGCTCCACA CAGCTCTGGCACATT |

Figure 19A:
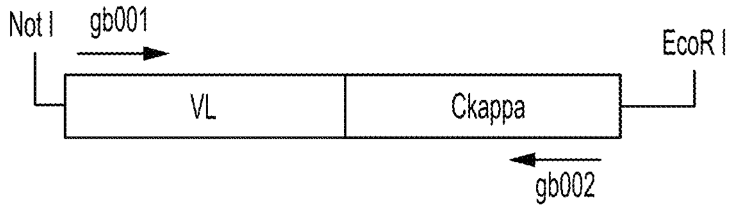
FIGS. 19A-C Illustrate the cloning strategy for assembling adalimumab light (FIG. 19A) and heavy chain (FIG. 19B) positive control antibody. PCR primers are designated as arrows, annotated by names as indicated in Table 3. Amplified fragments are shown in FIG. 19C.
Figure 19B:
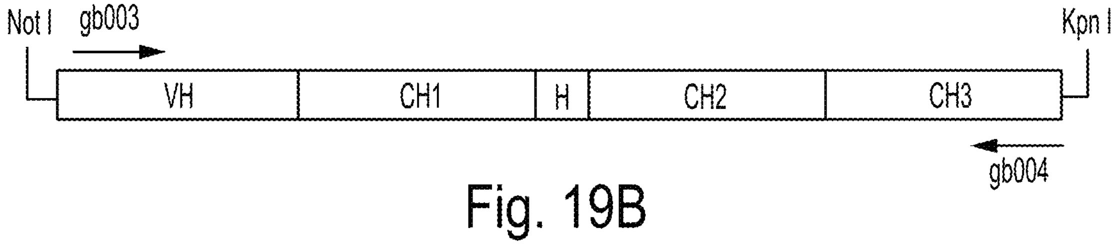
Figure 19C:
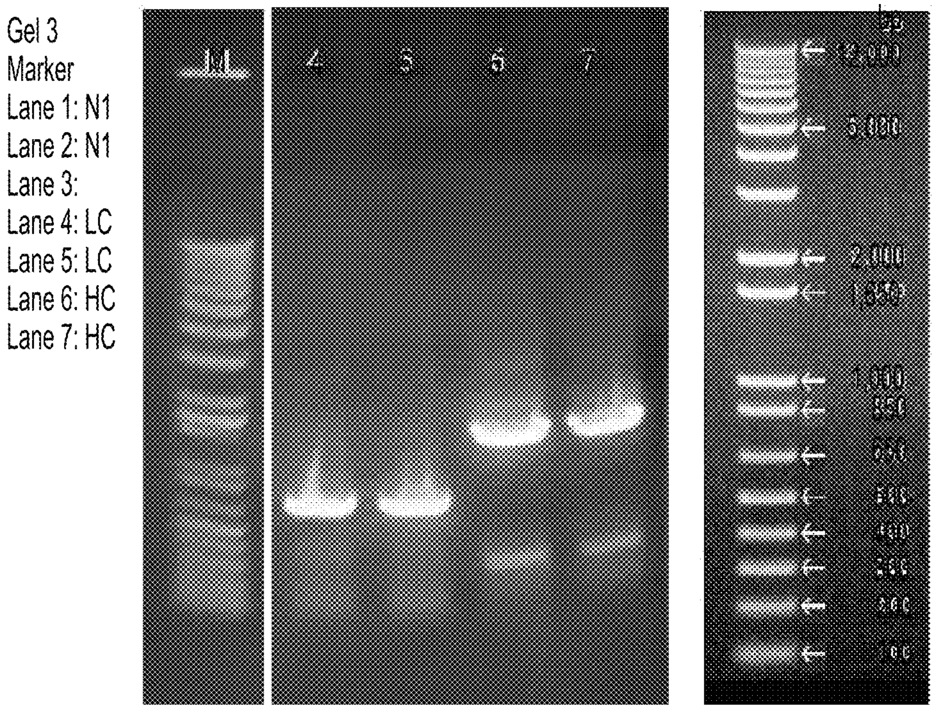

The strategy for assembling the full-length light and heavy chains of the positive control antibody (adalimumab) listed in example 1 is illustrated in FIGS. 19A and 19B respectively, and the pcr amplified products are shown in FIG. 19C. The amplified fragments were cloned into pcDNA3.1-for expression in mammalian cells using the restriction sites indicated.

Figure 20A:
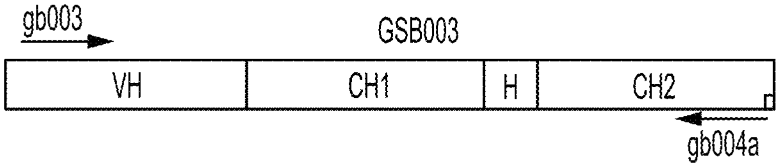
FIGS. 20A-C Illustrate the strategy for PCR amplification of heavy chain cassette fragments.
Figure 20B:
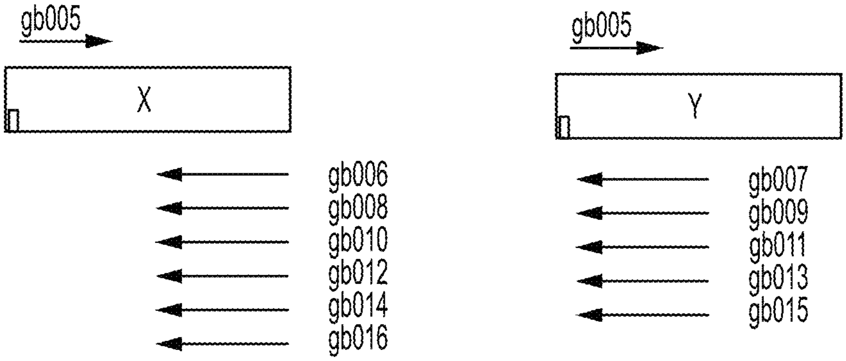
Figure 20C:
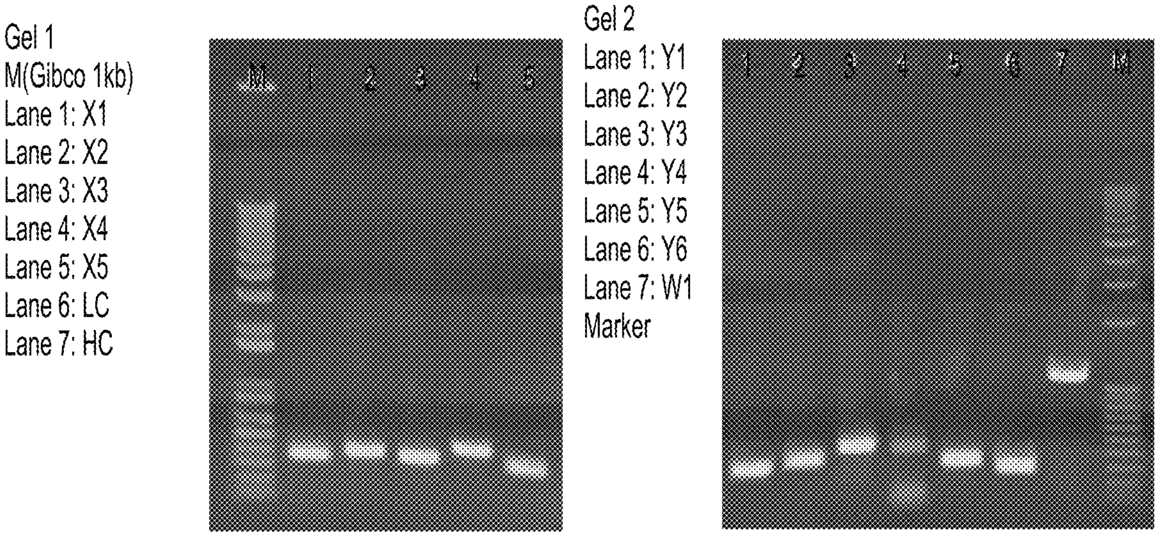

The strategy for amplification of paired heavy chains cassettes listed in examples 2-6, using templates and primers listed in Tables 2 and 3 respectively, is illustrated in FIG. 20.

Figure 21:
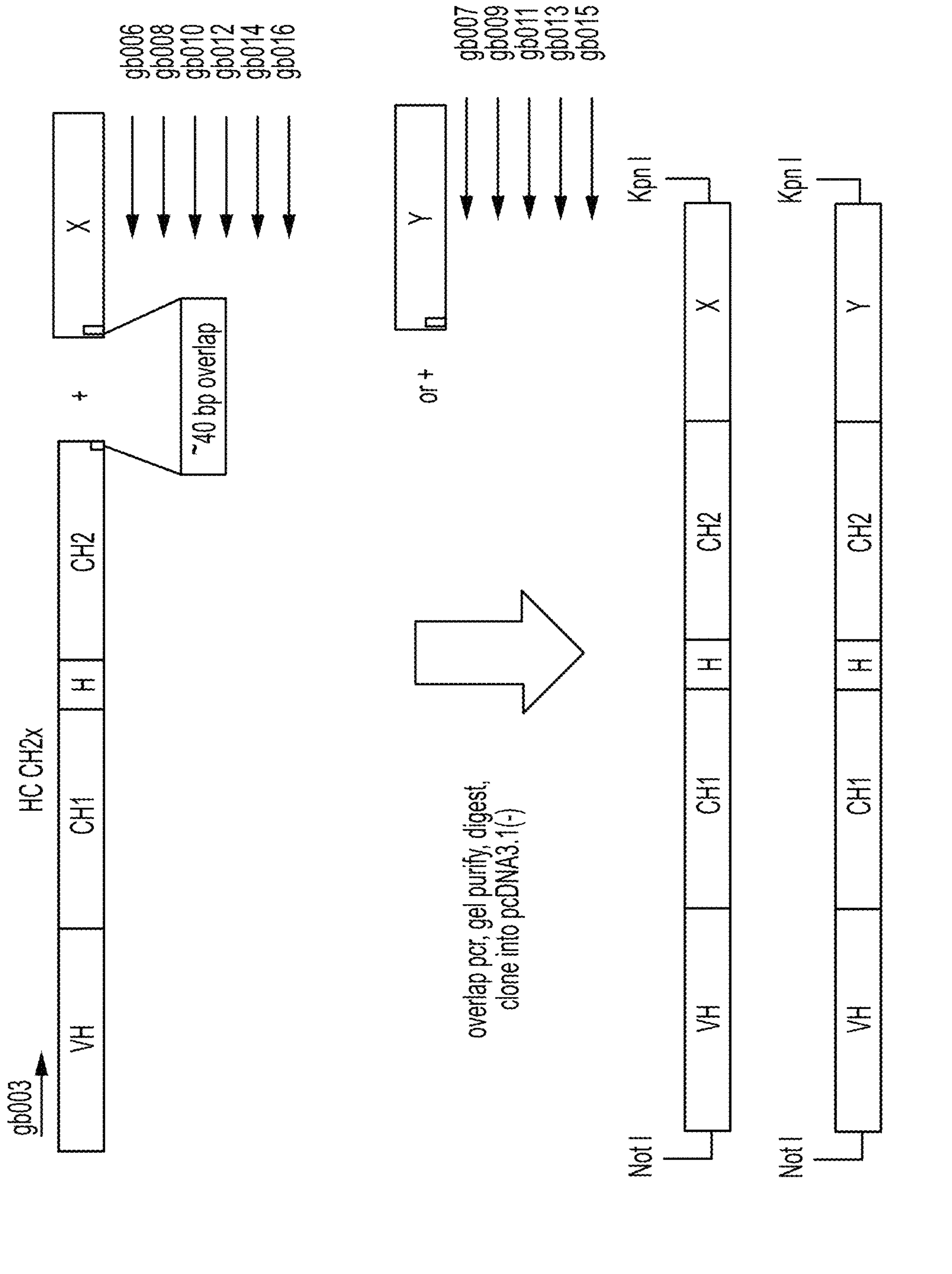
FIG. 21 Illustrates the strategy for assembly of full length heavy chain constructs by overlap pcr using end to end primer pairs, i.e. gb003+gb006, gb003+gb007, gb003+gb008, . . . gb003+gb016.

The strategy for assembling paired heterodimeric heavy chains listed in examples 2-6 from amplified cassette fragments (FIG. 20) is illustrated in FIG. 21, the pcr reaction set up is summarized in Table 15, and full length amplified heavy chain fragments are shown in FIG. 22.

TABLE 15

Reaction set up for over-lap pcr mediated assembly of paired full length heavy chain constructs illustrated in FIG. 21.

| Templates | Primer-1 (fwd) | Primer-2 (rev) | Product (bp) | Final Product | Lab Nomenclature |
|---|---|---|---|---|---|
| HC-CH2x + 1a/X1 | gb003 | gb006 | 1401 | FLHC1a | N1 |
| HC-CH2x + 1b/Y1 | gb003 | gb007 | 1379 | FLHC1b | N2 |
| HC-CH2x + 2a/X2 | gb003 | gb008 | 1452 | FLHC2a | N3 |
| HC-CH2x + 2b/Y2 | gb003 | gb009 | 1437 | FLHC2b | N4 |
| HC-CH2x + 3a/X3 | gb003 | gb010 | 1437 | FLHC3a | N5 |
| HC-CH2x + 3b/Y3 | gb003 | gb011 | 1506 | FLHC3b | N6 |
| HC-CH2x + 4a/X4 | gb003 | gb012 | 1521 | FLHC4a | N7 |
| HC-CH2x + 4b/Y4 | gb003 | gb013 | 1488 | FLHC4b | N8 |
| HC-CH2x + 5a/X5 | gb003 | gb014 | 1425 | FLHC5a | N9 |
| HC-CH2x + 5b/Y5 | gb003 | gb015 | 1395 | FLHC5b | N10 |
| HC-CH2x + 5c/Y6 | gb003 | gb016 | 1347 | FLHC5c | N11 |

The amplified fragments were purified from the gels shown in FIG. 22 and directionally cloned into pcDNA3.1-, using the restriction sites indicated in FIG. 21. DNA was isolated from individual bacterial colonies for sequence verification of the respective constructs. Purified maxi-prep DNA samples from sequence verified clones were used for transient transfection and expression in mammalian Expi293™ cells (grown to a density of 2.5E6 cells/mL at time of transfection) as summarized in Table 16 below. Transfections were performed using the Expi293™ Expression System [Gibco A14351] per manufacturer's protocol. Each transfection contained empty pcDNA3.1-vector, GFP expression plasmid, and the adalimumab light chain. The heavy chains were either the adalimumab heavy chain, or one, or both pairs of paired heavy chain combinations described in examples 1-5. All transfections were carried out with 1 μg of each construct A, construct B, & construct C, plus 0.1 μg construct D to each of the 21 reactions listed in Table 16. Two additional no-DNA control wells were included, and 7.5 μL Enhancer 1 and 75 μL Enhancer 2 was added to each well 20 hours post transfection.

TABLE 16

Transient transfections with expression constructs: PC LC-positive control adalimumab light chain; PC HC-positive control adalimumab heavy chain; empty vector-pcDNA3.1-; GFP-green fluorescent protein expression vector; FLHC1a-Adalimumab HC/MHC I α1 domain fusion; FLHC1b-Adalimumab HC/β2microglobulin; FLHC2a-Adalimumab HC/MHCII α2 domain fusion; FLHC2b-Adalimumab HC/MHC II β2 domain fusion; FLHC3a-Adalimumab HC/TCR Cα domain fusion; FLHC3b-Adalimumab HC/TCR Cβ; FLHC4a-Adalimumab HC/TCR Cγ domain fusion; FLHC4b-Adalimumab HC/TCR Cδ domain fusion; FLHC5a-Adalimumab HC/CD3 ε-ectodomian fusion; FLHC 5b-Adalimumab HC/CD3 γ-ectodomain; FLHC 5c-Adalimumab HC/CD3 δ-ectodomain;

| Transfection/ Sample # | Construct A | Construct B | Construct C | Construct D (@ 0.1X tot DNA) |
|---|---|---|---|---|
| 1 | PC LC | PC HC | empty vector | GFP |
| 2 | PC LC | PC HC | empty vector | GFP |
| 3 | PC LC | PC HC | empty vector | GFP |
| 4 | PC LC | FLHC1a | empty vector | GFP |
| 5 | PC LC | FLHC1a | FLHC1b | GFP |
| 6 | PC LC | empty vector | FLHC1b | GFP |
| 7 | PC LC | FLHC2a | empty vector | GFP |
| 8 | PC LC | FLHC2a | FLHC2b | GFP |
| 9 | PC LC | empty vector | FLHC2b | GFP |
| 10 | PC LC | FLHC3a | empty vector | GFP |
| 11 | PC LC | FLHC3a | FLHC3b | GFP |
| 12 | PC LC | empty vector | FLHC3b | GFP |
| 13 | PC LC | FLHC4a | empty vector | GFP |
| 14 | PC LC | FLHC4a | FLHC4b | GFP |
| 15 | PC LC | empty vector | FLHC4b | GFP |
| 16 | PC LC | FLHC5a | empty vector | GFP |
| 17 | PC LC | FLHC5a | FLHC5b | GFP |
| 18 | PC LC | empty vector | FLHC5b | GFP |
| 19 | PC LC | FLHC5a | empty vector | GFP |
| 20 | PC LC | FLHC5a | FLHC5c | GFP |
| 21 | PC LC | empty vector | FLHC5c | GFP |

Figure 23:
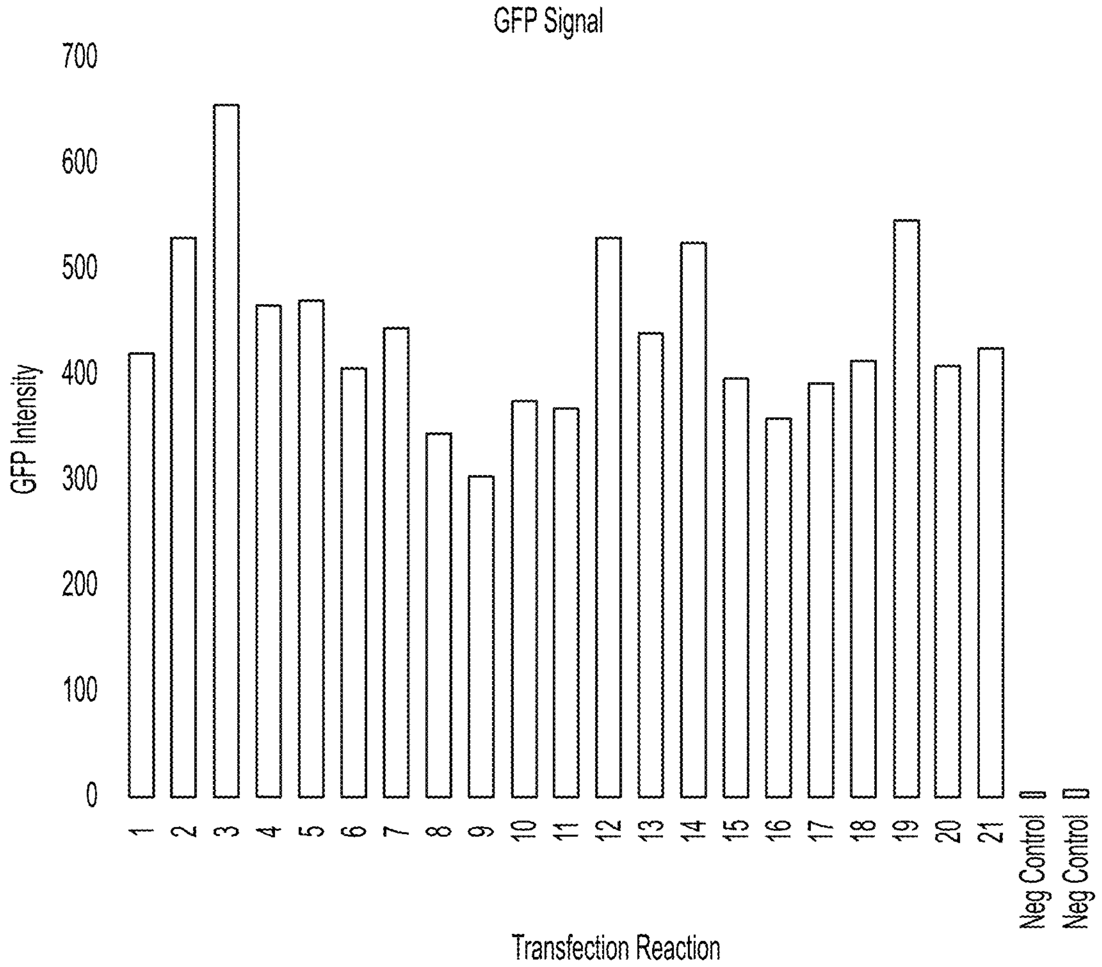
FIG. 23 GFP expression levels in cells harvested 72 hr post transfection. Reaction numbers are as indicated in Table 5.
Figure 24A:
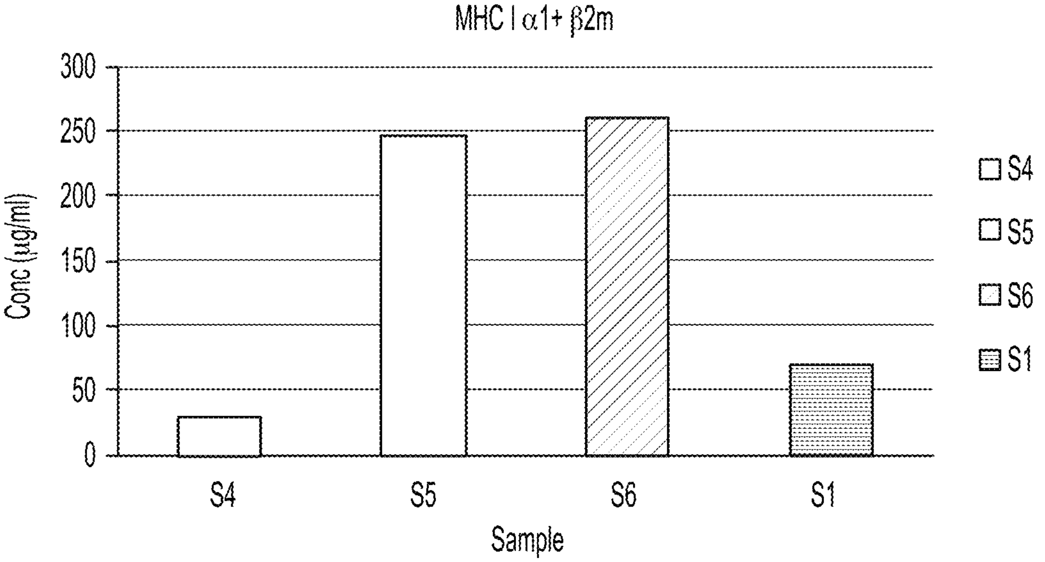
FIG. 24. Protein concentrations in conditioned media from transfections listed in Table 5. Sample numbers in the figure correspond to transfection numbers in Table 5. For each set of transfections, the single heavy chain transfected samples are indicated by left or right diagonal bars, and the samples transfected with the paired heavy chains are indicated by the black bars. S1 (positive control antibody adlimumab) is used as the reference for comparison with all the test constructs.
Figure 24B:
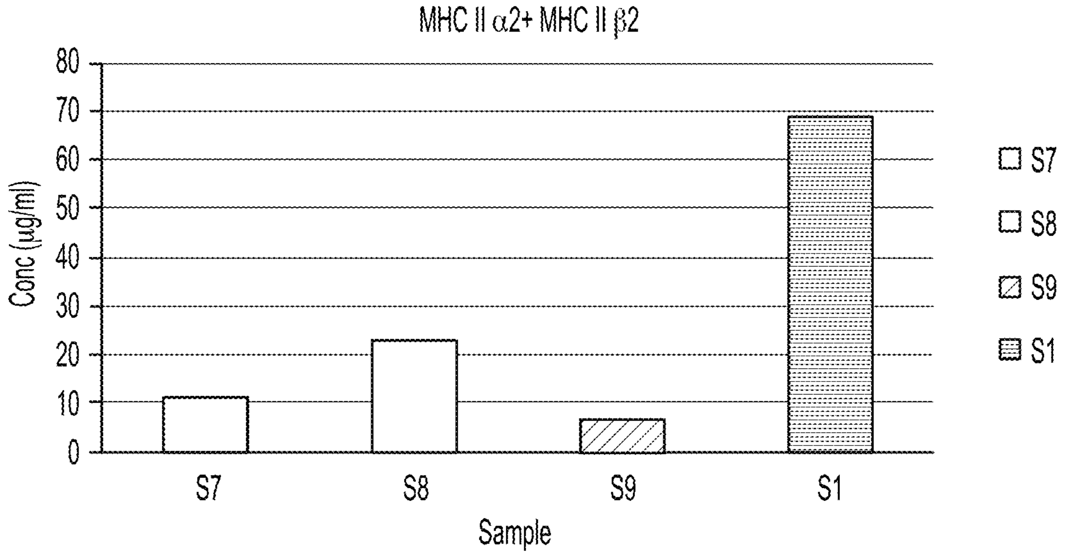
Figure 24C:
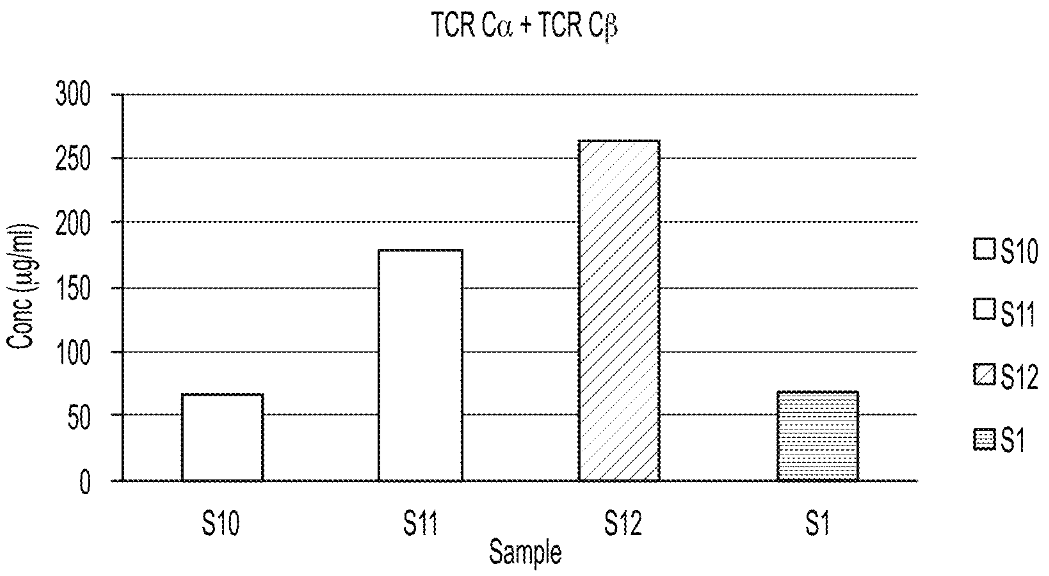
Figure 24D:
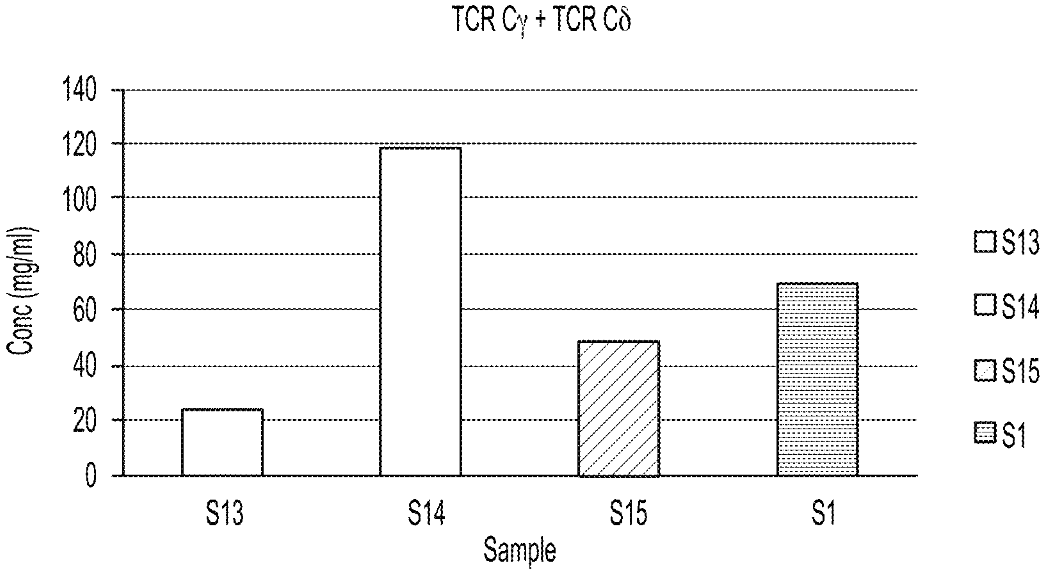
Figure 24E:
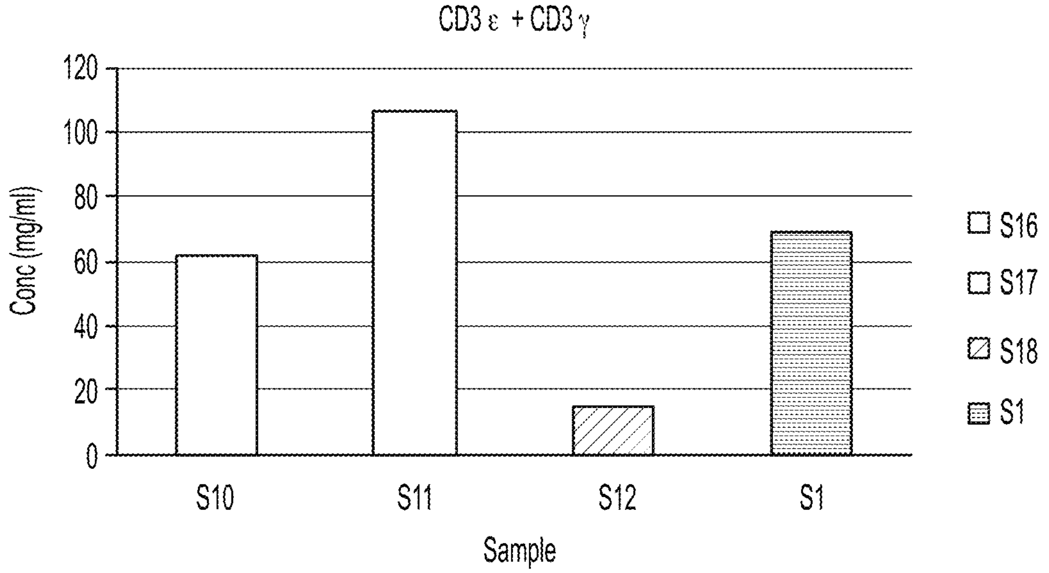
Figure 24F:
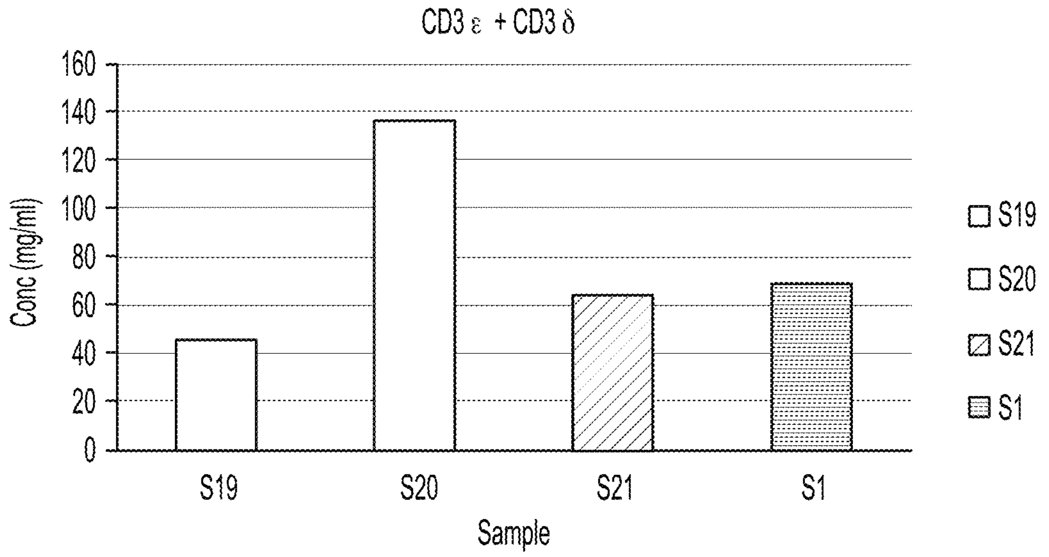

Conditioned media was harvested from cells 72 h post transfection for detection of expressed and secreted proteins by immunoassay, and transfected cells were harvested for analysis of GFP reporter by flow cytometry to check transfection efficiency across all reactions listed in Table 16. The GFP expression in transfected cells is shown in FIG. 23.

Expression of recombinant protein by the transfected cells, and concentration of protein in conditioned media was confirmed by ELISA. ELISA for protein concentration was carried out in 96 well plates coated overnight with 100 uL of 10 ug/mL Goat anti human IgG (Jackson Immune lab, Cat. 109-005-008) per well (1 ug/well). The coated plates were blocked, washed, incubated with 100 uL/well conditioned media in triplicate from transfected cells, or human IgG as concentration standard for 1 hr. at room temperature, washed again and incubated with 100 uL of 1:10000 HRP conjugated second antibody (Jackson immune lab, Cat. 109-035-003) in blocking buffer at RT for 1 hr. as detection reagent, washed and developed by adding 100 uL of $H_2O_2$-Amplx Red HRP substrate for 30 min at RT in the dark. Human IgG was used as concentration standard in the ELISA at a range of concentrations. Results from concentration assessment of conditioned media from transfections listed in Table 16 are presented in FIGS. 24A-F. The results in FIG. 24 demonstrate robust expression of paired heavy chain heterodimers (black bars) relative to the unpaired heavy chain constructs (left or right diagonal bars), as well as relative to the positive control antibody adalimumab (grey shaded bars).

Biochemical characterization of the secreted heavy chains homo and heterodimers was carried out by immunoprecipitation of conditioned media, followed by SDS-PAGE. Immunoprecipitation was carried out on an equal amount of protein (~10 g/sample, based on concentration as determined in FIG. 24) from each transfected sample, as follows:

1. Final volume of all samples was adjusted to 1 mL with 1×PBS (Table #) containing BSA (conc.) to keep total protein conc the same in all the samples.
2. 20 μL of AbraMag™ Goat anti-Human IgG magnetic beads [Abraxis 544060] was added to each sample (Table #) and incubated for 1 hour with mixing.
3. Following incubation, media was removed from beads using a DynaMag™-2 [Invitrogen 12321D] magnetic separator.
4. Beads were resuspended 3× with 0.5 mL RIPA buffer followed by 2× wash with PBS.
5. Protein was eluted from beads with 30 μL 1× Non-Reducing LiDS Sample Buffer.
6. Half of the sample volume (15 μL) was reduced with PME (10% final concentration).
7. All samples were heated (95° C., 5 min), chilled on ice, then centrifuged for 2 minutes prior to loading on gel.
8. Samples were (15 μL per lane) were run on SDS-PAGE 4-12% gradient gels.
9. Following electrophoresis, gels were stained with GelCode™ Blue Safe Protein Stain [Thermo Scientific #24594] and destained as per manufacturer's recommendation.

Figure 25A:
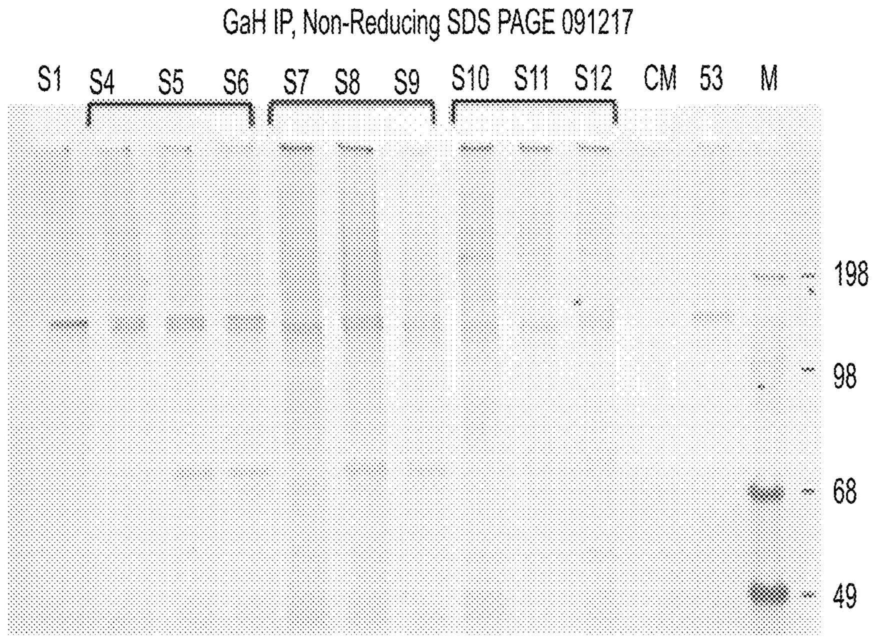
FIGS. 25A-C show non-reducing (FIG. 20A & B) and reducing (FIG. 20C) Coomassie blue stained SDS-PAGE of immunoprecipitated conditioned media samples. Sample numbers annotated above the lanes on the respective gels are as listed in Table 5.
Figure 25B:
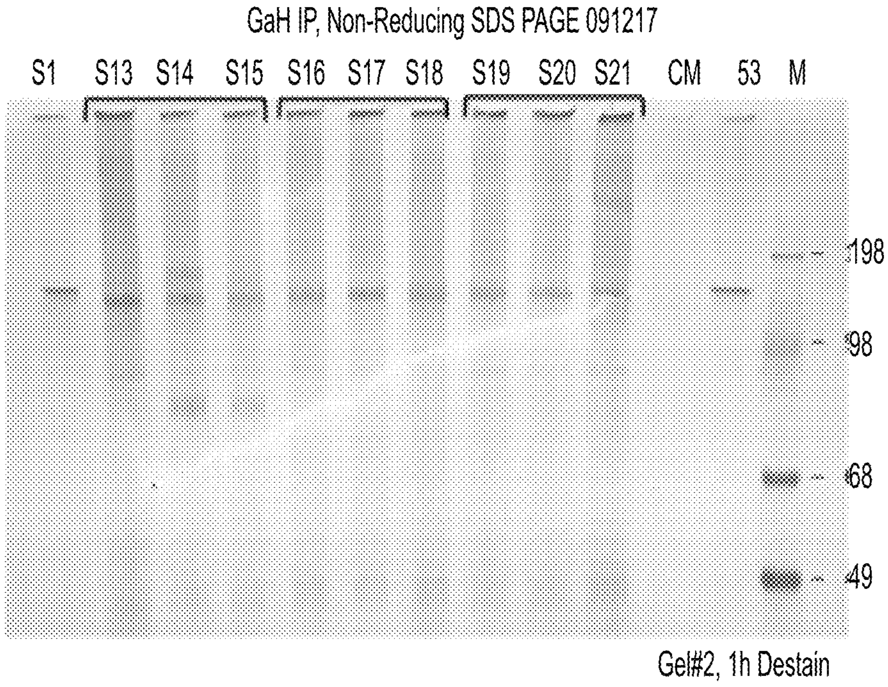
Figure 25C:
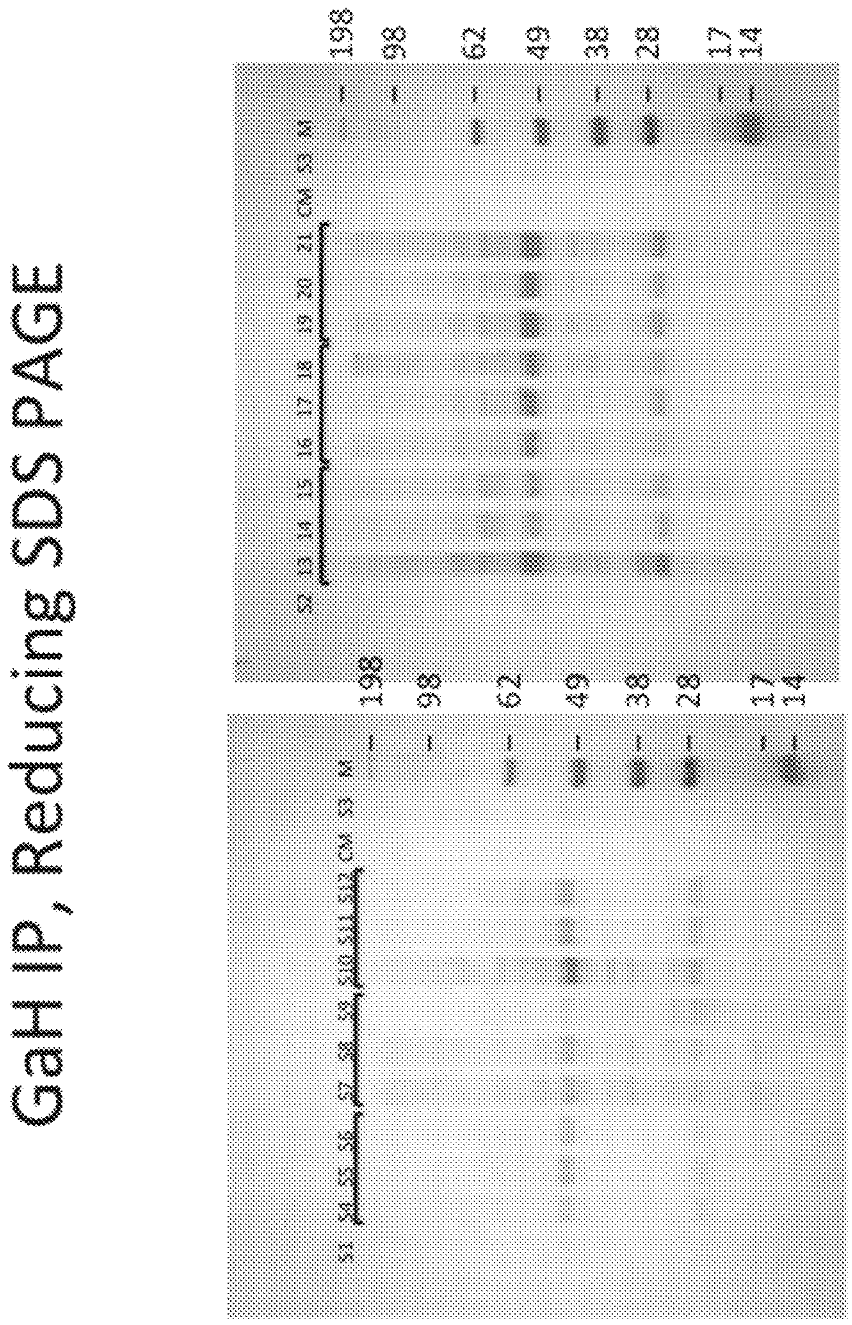
Figure 26A:
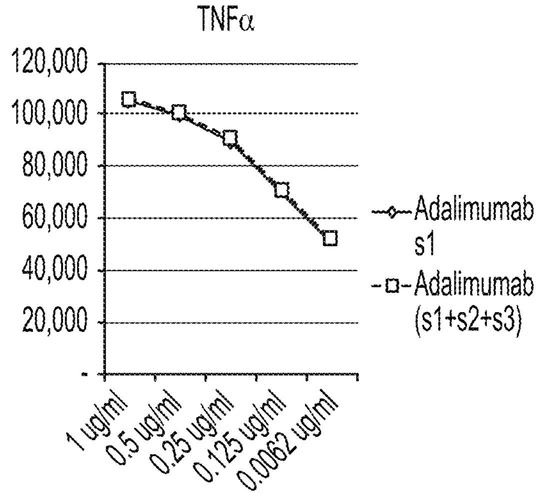
FIGS. 26A-F Show results from ELISA assay for binding to TNFα antigen immobilized on plates demonstrating function of hybrid heavy chain homodimers as well as paired heavy chain heterdimers. The left panel in each part of FIG. 26 shows binding to antigen, and the right panel in each part of FIG. 26 shows relative concentration of each sample by ELSIA using goat-anti-human capture and reporter antibodies as described in examples.
Figure 26B:
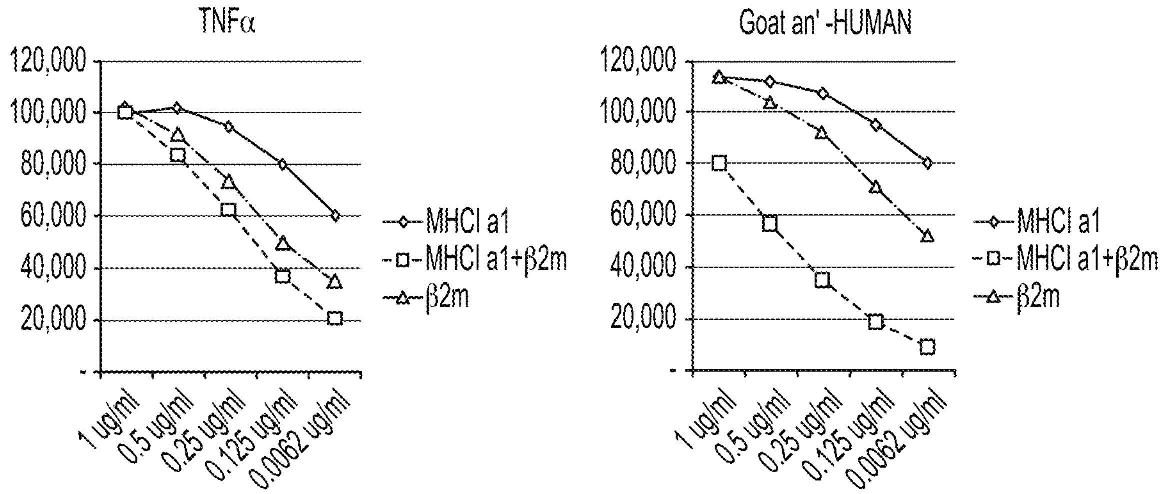
Figure 26C:
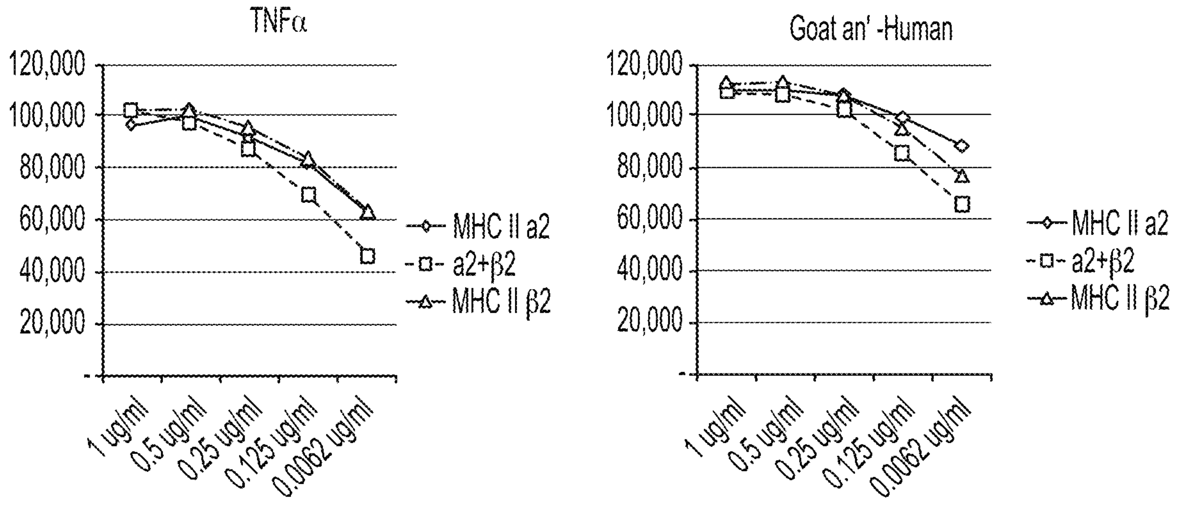
Figure 26D:
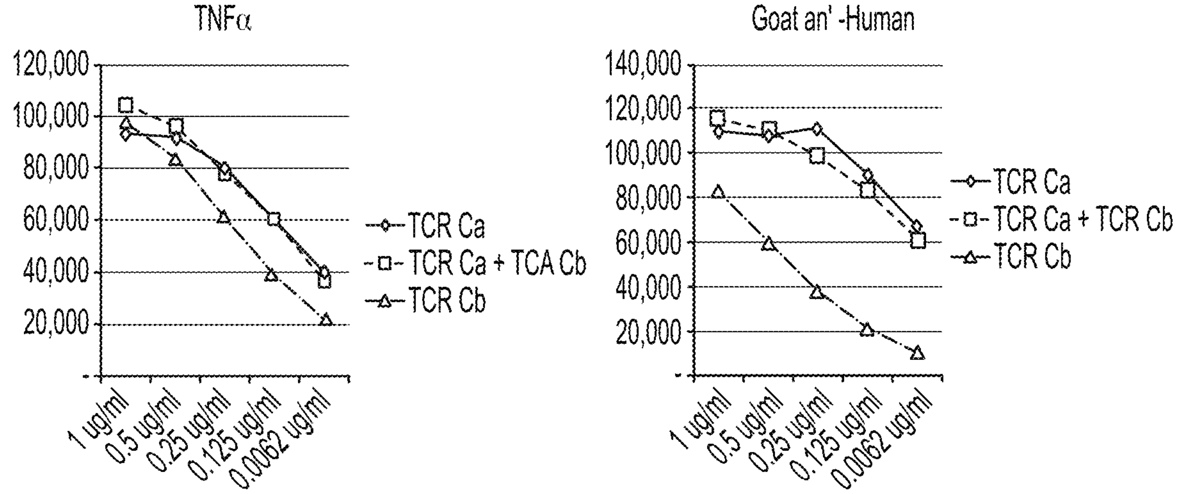
Figure 26E:
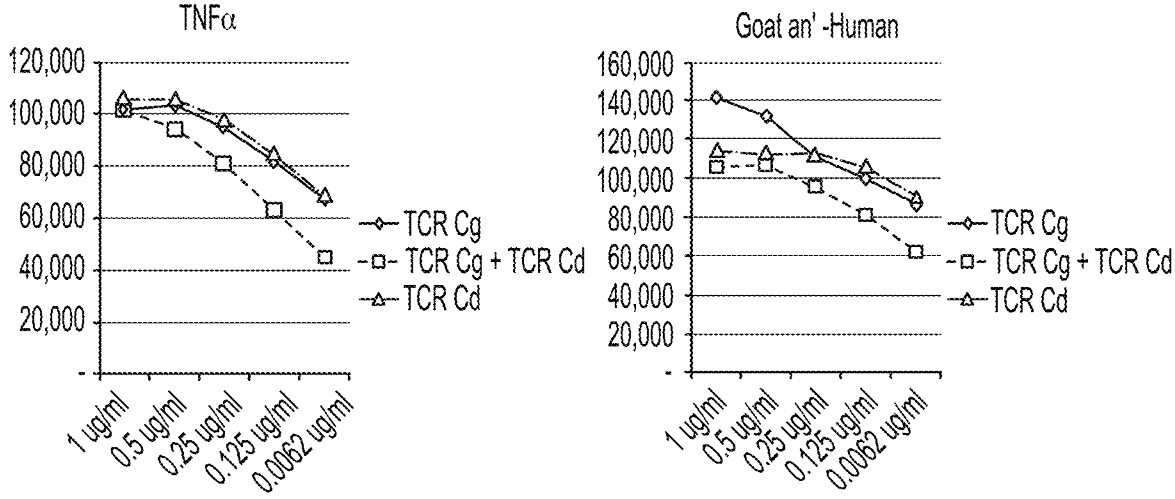
Figure 26F:
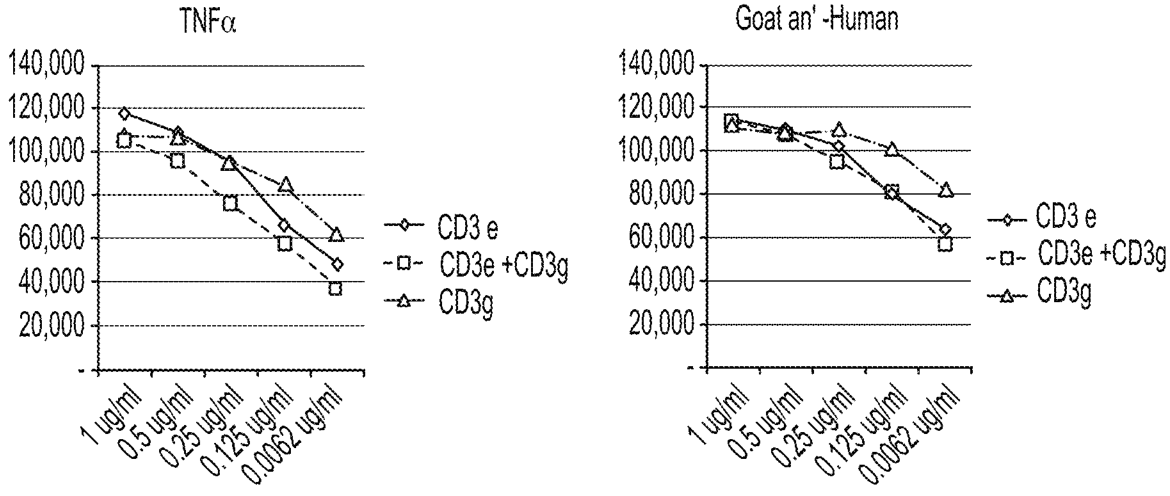
Figure 26G:
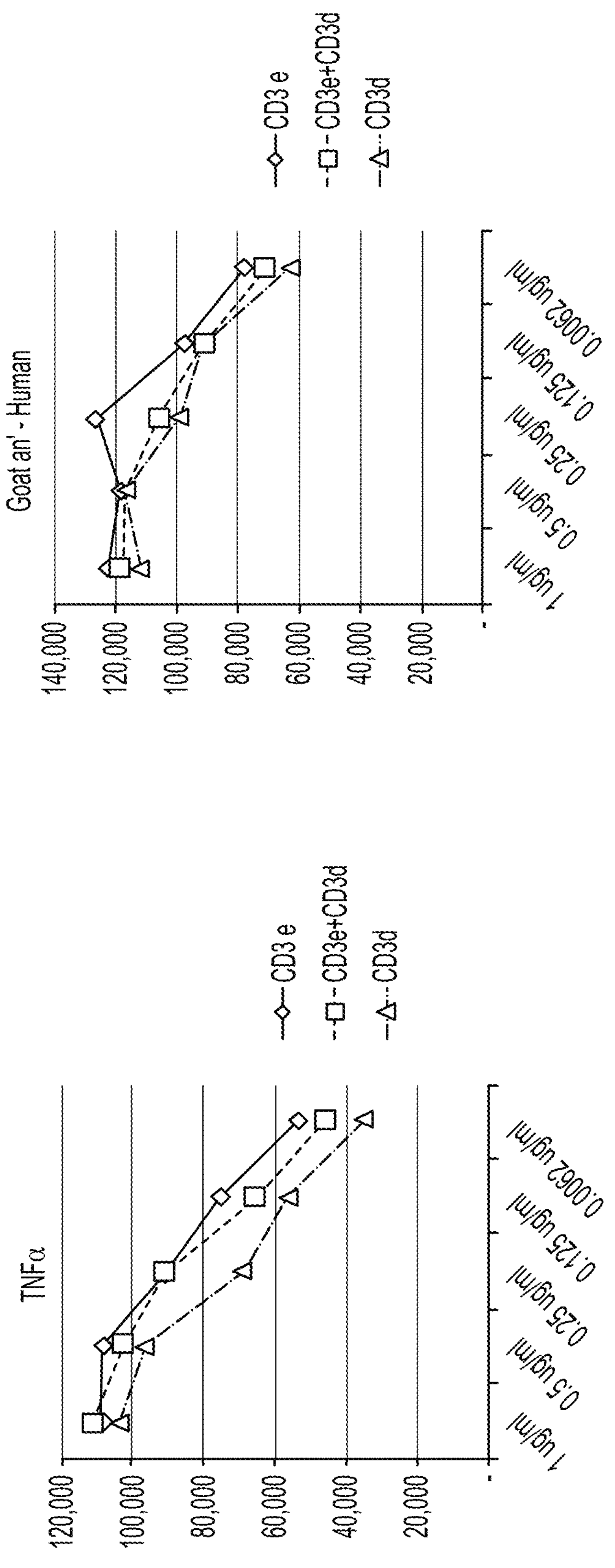
FIG. 26G CD3 ε and CD3 δ as homodimers (diamond and triangle symbols, respectively) or heterodimer (square symbol).

Coomassie blue stained images of non-reducing gels are shown in FIGS. 25A & B, and reducing gels are shown in FIG. 25C.

Functional binding of the recombinant antibodies as either heavy chain homodimers, or heavy chain heterodimers was confirmed by antigen recognition in an ELISA format. The antigen, TNFα was immobilized on plates followed by incubation with equal concentrations of conditioned media from cells co-transfected with adalimumab light chain plus either hybrid heavy chain monomers (homodimers), or paired hybrid heavy chains (heterodimers), as indicated in Table 16. For confirming binding of samples to immobilized antigen, all samples were diluted to a nominal starting 1 μg/ml, and 2λ serial dilutions were applied to the antigen coated plates. In parallel, the samples were also assayed for actual concentration in the assay by capture on Goat anti-Human antibody coated plates, and the concentration was determined relative to a control human antibody of known concentration as a reference standard. The results, shown in FIGS. 26A-F confirm function of the recombinant proteins for binding to immobilized TNFα antigen.

The invention claimed is:

1. A heterodimeric bispecific antibody comprising a. a first antigen recognizing moiety (C); and b. a second antigen recognizing moiety (D) wherein:

C comprises a first light chain variable region (VL1) fused to a first heavy chain variable region (VH1), wherein the VL1 or the VH1 is fused through a first hinge region ($H_1$), to a first heavy chain pairing partner (X);

D comprises a second light chain variable region (VL2) fused to a second heavy chain variable region (VH2), wherein the VL2 or the VH2 is fused through a second hinge region ($H_2$), to a second heavy chain pairing partner (Y); and X and Y are a binding pair derived from MHC class I molecules (MHC I), MHC class II molecules (MHC II) or T-cell receptor complex of molecules (TCR), wherein the X and Y binding pair is MHC II α2 domain and MHC II 2 domain; the X and Y binding pair is TCR CD3 ε chain and TCR CD3 γ chain; the X and Y binding pair is TCR CD3 ε chain and TCR CD3 δ chain; the X and Y binding pair is TCR AgR Cα domain and TCR AgR Co domain; the X and Y binding pair is MHC I α3 domain and beta-2 microglobulin (β2M); or the X and Y binding pair is TCR AgR Cγ domain and TCR AgR Cδ domain, wherein the heterodimeric bispecific antibody was produced by expression and assembly of C and D in the same cell.

2. The heterodimeric bispecific antibody of claim 1, wherein VH1 or VL1 is fused to X through the $H_1$ and a first heavy chain constant reqion CH2 ($CH2_1$); and VH2 or VL2 is fused to Y through the $H_2$ and a second heavy chain constant reqion CH2 ($CH2_2$).

3. The heterodimeric bispecific antibody of claim 2, wherein one or more of $H_1$, $H_2$, $CH2_1$ and $CH2_2$ are from human IgG isotypes 1, 2, 3 or 4.

4. The heterodimeric bispecific antibody of claim 3, wherein $H_1$, $H_2$, $CH2_1$ and $CH2_2$ are from human IgG1.

5. The heterodimeric bispecific antibody of claim 1, wherein at least one of C and D is derived from abagoavomab, abciximab, abituzumab, abrilumab, actoxumab, adalimumab, adecatumumab, aducanumab, afasevikumab, afelimomab, afutuzumab, alacixumab pegol, alemtuzumab, alirocumab, altumomab pentetate, amatuximab, anatumomab mafeatox, anetumab ravtansine, anifrolumab, anrukinzumab, apolizumab, arcitumomab, ascrinvacumab, aselizumab, atezolizumab, atinumab, atizumab, atorolimumab, avelumab, bapeineuzumab, natalizumab, basiliximab, bavituximab, bectumomab, begelomab, belimumab, benralizumab, bertilimumab, besilesomab, bevacizumab, bezlotoxumab, biciromab, bimagrumab, bimekizumab, bivatuzumab mertansine, bleselumab, blinatumomab, blontuvetmab, blosozumab, bococizumab, brazikumab, brentuximab vedotin, briakinumab, brodalumab, brolucizumab, brontictuzumab, burosumab, cabiralizumab, canakinumab, cantuzumab metansine, cantuzumab ravtansine, caplacizumab, capromab pendetide, carlumab, carotuximab, cedelizumab, cergutuzumab amunaeleukin, certolizumab pegol, cetuximab, cituximab bogatox, cixutumumab, clazakizumab, clenoliximab, clivatuzumab tetraxetan, codrituzumab, coltuximab ravtansine, conatumumabe, concizumab, crenezumab, coredumab, dacetuzumab, daclizumab, dalotuzumab, dapirolizumab pegol, daratumumab, dectrekumab, demcizumab, denosumab, depatuxizumab, derlotuximab, detumomab, dinutuxidmab, diridavumab, domogrozumab, dorimomab, drozitumab, duligotumab, dupilumab, durvalumab, dusigitumab, ecromeximab, eculizumab, edobabcomab, edrecolomab, efalizumab, efungumab, eldelumab, elgemtumab, elotuzumab, elsilimomab, emactuzumab, emibetuzumab, emicizumab, enavatuzumab, enlimomab, enoblituzumab, enokizumab, enoticumab, ensituximab, eptitumomab, epratuzumab, erenumab, erlizumab, ertumaxomab, etaracizumab, etrolizumab, evinacumab, evolocumab, exbivirumab, fanolesomab, farlimomab, farletuzumab, fasinumab, felvizumab, fezakinumab, figitumumab, firivumab, flanvotumab, fletikumab, fontolizumab, foralumab, foravirumab, fresolimumab, fluranumab, futuximab, glacanezumab, galiximab, ganitumab, gantenerumab, gavilimomab, gemtuzumab, gevokizumab, girentuximab, glembatumumab, golimumab, gomiliximab, guselkumab, ibalizumab, ibritumomab, icrucumab, idarucizumab, igovomab, imalumab, imciromab, imgatuzumab, inclacumab, indatuximab, indusatumab, inebilizumab, infliximab, intetumumab, inolimomab, inotuzumoab, ipilimumab, iratmumab, isatuximab, itolizumab, ixekizumab, keliximab, labetuzumab, lampalizumab, landelumab, landogrozumab, laprituximab, lebrikizumab, lemalesomab, lendalizumab, lenzilumab, lerdelimumab, lexatumumab, libivirumab, lifastuzumab, ligelizumab, lilotomab, lintuzumab, lirilumab, lodelcizumab, likivetmab, lorvotuzumab, lucatumumab, lulizumab, lumiliximab, lumretuzumab, mapatumumab, margetuximab, maslimomab, mavrilimumab, matuzumab, mepolizumab, metelimumab, milatuzumab, minretumomab, mirvetuximab, mitumomab, mogamulizumab, monalizaumab, morolimumab, motavizumab, moxetumomab, muromonab, nacolomab, namilumab, naptumomab, natatuximab, narnatumab, natalizumab, navicixizumab, navivumab, nebacumab, necitumumab, nemolizumab, nerelimomab, nesvacumab, nimotuzumab, nivolumab, nofetumomab, obiltoxaximab, obinutuzumab, ocaratuzumab, ocrelizumab, odulimomab, ofatumumab, olaratumab, olokizumab, oalizumab, onartuzumab, ontuxizumab, opicinumab, opotruzumab, oregovomab, orticumab, otelixizumab, otlertuzumab, oxelumab, ozanezumab, ozoralizumab, pagibximab, palivizumab, pamrevlumab, pankomab, panobacumab, parsatuzumab, pascolizumab, pateclizumab, patritumab, pembrolizumab, pemtumomab, perakizumab, pertuzumab, pexelizumab, pidilizumab, pinatuzumab, pintumomab, placulumab, plozalizumab, polatuzumab, ponezumab, prezalizumab, priliximab, pritoxaximab, pritumumab, quilizumab, racotumomab, radretumab, rafivirumab, ralpancizumab, ramucirumab, ranibizumab, ranibizumab, raxibacumab, refanezumab, regavirumab, reslizumab, rilotmumab, rinucumab, risankizumab, rituximab, rivabazumab, robatumumab, roledumab, romosozumab, rontalizumab, rovalpituzumab, rovelizumab, ruplizumab, sacituzumab, samalizumab, sapelizumab, sarilumab, satumomab, secukinumab, seribantumab, setoxaximab, sevirumab, sibrotuzumab, sifalimumab, siltuximab, simtuzumab, siplizumab, sirukumab, sofituzumab, solanezumab, solitomab, sonepcizumab, sontuzumab, stamulumab, sulesomab, suvizumab, tabalumab, tacatuzumab, tadocizumab, talizumab, tamtuetmab, tanezumab, tefibazumab, telimomab, tenatumomab, teneliximab, teplizumab, teprotumumab, tesidolumab, tetlomab, tezepelumab, ticilimumab, tildrakizumab, tigatuzumab, timolumab, tisotumab, tocilizumab, tosatoxumab, tositumomab, tovetumab, tralokinumab, trastuzumab, tregalizumab, tremelimumab, trevogrumab, tocutuzumab, tuvirumab, ulituximab, ulocuplumab, urelumab, urtoxazumab, ustekinumab, utomilumab, vadastuximab, vandortuzumab, vantictumab, vanucizumab, vapaliximab, varlillumab, vatelizumab, vedolizumab, veltuzumab, vepalimomab, vesencumab, visilizumab, vobarilizumab, volociximab, vorsetuzumab, votumumab, xentuzumab, zalutumumab, zanolimumab, zatuximab, ziralimumab or zolimomab.

6. The heterodimeric bispecific antibody of claim 5, wherein C or D, but not both, is derived from adalimumab.

7. The heterodimeric bispecific antibody of claim 6, wherein VH1, and VL1 are from adalimumab, X is MHC I $\alpha 3$ domain and Y is beta-2 microglobulin ($\beta 2M$).

8. The heterodimeric bispecific antibody of claim 6, wherein VH1 and VL1, are from adalimumab, X is beta-2 microglobulin ($\beta 2M$) and Y is MHC I $\alpha 3$ domain.

9. A pharmaceutical composition comprising the heterodimeric bispecific antibody of claim 1.

10. The heterodimeric bispecific antibody of claim 1, wherein the VL1 is fused to the VH1 via intervening amino acids and the VL2 is fused to the VH2 via intervening amino acids.

* * * * *

UNITED STATES PATENT AND TRADEMARK OFFICE

CERTIFICATE OF CORRECTION

PATENT NO. : 12,195,529 B2
APPLICATION NO. : 16/625628
DATED : January 14, 2025
INVENTOR(S) : Guriqbal S. Basi It is certified that error appears in the above-identified patent and that said Letters Patent is hereby corrected as shown below:

In the Claims

At Column 167, Line 29, Claim 1, delete "MHC II 2 domain" and insert -- MHC II β2 domain --, therefor.

At Column 167, Line 33, Claim 1, delete "Co domain" and insert -- Cβ domain --, therefor.

At Column 167, Line 36, Claim 1, delete "domain," and insert -- domain; --, therefor.

At Column 167, Line 42, Claim 2, delete "reqion" and insert -- region --, therefor.

At Column 167, Line 44, Claim 2, delete "reqion" and insert -- region --, therefor.

Signed and Sealed this
Eighth Day of July, 2025

Coke Morgan Stewart
*Acting Director of the United States Patent and Trademark Office*